United States Patent
Ombrato et al.

(10) Patent No.: US 10,369,130 B2
(45) Date of Patent: *Aug. 6, 2019

(54) ANTIBACTERIAL COMPOUNDS

(71) Applicant: AZIENDE CHIMICHE RIUNITE ANGELINI FRANCESCO A.C.R.A.F. S.p.A., Rome (IT)

(72) Inventors: Rosella Ombrato, Rome (IT); Barbara Garofalo, Rome (IT); Giorgina Mangano, Rome (IT); Alessandra Capezzone De Joannon, Rome (IT); Gaia Corso, Rome (IT); Gabriele Magaro', Ariccia (IT); Guido Furlotti, Rome (IT); Tommaso Iacoangeli, Rome (IT)

(73) Assignee: AZIEN DE CHIMICHE RIUNITE ANGELINI FRANCESCO A.C.R.A.F. S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/534,874

(22) PCT Filed: Dec. 11, 2015

(86) PCT No.: PCT/EP2015/079352
§ 371 (c)(1),
(2) Date: Jun. 9, 2017

(87) PCT Pub. No.: WO2016/096631
PCT Pub. Date: Jun. 23, 2016

(65) Prior Publication Data
US 2017/0368017 A1    Dec. 28, 2017

(30) Foreign Application Priority Data
Dec. 17, 2014  (EP) ..................... 14198412

(51) Int. Cl.
| | | |
|---|---|---|
| *A61K 31/4725* | (2006.01) | |
| *A61P 31/04* | (2006.01) | |
| *C07D 401/04* | (2006.01) | |
| *C07D 401/12* | (2006.01) | |
| *C07D 401/14* | (2006.01) | |
| *A61K 31/33* | (2006.01) | |
| *C07D 405/14* | (2006.01) | |
| *C07D 413/14* | (2006.01) | |
| *C07D 405/12* | (2006.01) | |
| *C07D 407/14* | (2006.01) | |
| *C07D 409/14* | (2006.01) | |

(52) U.S. Cl.
CPC ............ *A61K 31/33* (2013.01); *C07D 401/04* (2013.01); *C07D 401/14* (2013.01); *C07D 405/12* (2013.01); *C07D 405/14* (2013.01); *C07D 407/14* (2013.01); *C07D 409/14* (2013.01); *C07D 413/14* (2013.01)

(58) Field of Classification Search
CPC .............. A61K 31/4725; C07D 401/04; C07D 401/12; C07D 401/14
See application file for complete search history.

(56) References Cited

U.S. PATENT DOCUMENTS

| | | | |
|---|---|---|---|
| 5,143,916 A | 9/1992 | Lavielle et al. | |
| 6,127,357 A * | 10/2000 | Cliffe ................... | C07D 213/75 514/210.2 |
| 7,799,775 B2 * | 9/2010 | Sato ..................... | A61K 31/496 514/222.2 |
| 7,919,494 B2 * | 4/2011 | Ishii ....................... | A61K 31/44 514/253.01 |
| 8,334,290 B2 * | 12/2012 | Ali ....................... | C07D 235/18 514/253.1 |
| 8,623,872 B2 * | 1/2014 | Guillemont .......... | C07D 401/12 514/252.16 |
| 2008/0125463 A1 | 5/2008 | Braeuer et al. | |
| 2009/0258862 A1 | 10/2009 | Colletti et al. | |
| 2012/0040957 A1 | 2/2012 | Gaucher et al. | |
| 2014/0221348 A1 | 8/2014 | Gaucher et al. | |
| 2015/0080373 A1 | 3/2015 | Gaucher et al. | |
| 2017/0369450 A1 * | 12/2017 | Ombrato .............. | C07D 241/04 |

FOREIGN PATENT DOCUMENTS

| | | |
|---|---|---|
| EP | 1 903 038 A1 | 3/2008 |
| EP | 2 924 032 A1 | 9/2015 |
| WO | WO 98/10568 A1 | 4/1996 |
| WO | 00/41697 A1 | 7/2000 |
| WO | WO 02/072572 A1 | 9/2002 |
| WO | 2004/087145 A2 | 10/2004 |
| WO | WO 2006/021448 A1 | 3/2006 |
| WO | WO 2006/046552 A1 | 5/2006 |
| WO | 2006/081289 A2 | 8/2006 |

(Continued)

OTHER PUBLICATIONS

Modi et al., Understanding the Structural Requirements of Hybrid (S)-6-((2-(4-phenylpiperazin-1-yl)-ethyl)(propyl)amino)-4,5,6,7,8,-tetrahydronaphthalen-1-ol and its Analogs as D2/D3 Receptor Ligands: a 3D QSAR Investigation, Med. Chem. Comm., vol. 5, No. 9, pp. 1384-1399 (Year: 2014).*

Ghosh et al., Development of (S)-N6-(2-(4-(Isoquinolin-1-yl)piperazin-1-yl)ethyl)-N6-propyl-4,5,6,7-tetrahydrobenzo[d]-thiazole-2,6-diamine and Its Analogue as a D3 Recept. Preferring Agonist: Potent in Vivo Act. in Parkinson's Disease Animal Models, J. of Med. Chem., vol. 53, No. 3, pp. 1023-1037 (Year: 2010).*

Leopoldo et al., Design, Synthesis, and Binding Affinities of Potential Positron Emission Tomography (PET) Ligands for Visualization of Brain Dopamine D3 Receptors, Journal of Medicinal Chemistry, vol. 49, No. 1, pp. 358-365 (Year: 2006).*

(Continued)

*Primary Examiner* — Brenda L Coleman
(74) *Attorney, Agent, or Firm* — Oblon, McClelland, Maier & Neustadt, L.L.P.

(57) ABSTRACT

The present invention relates to novel antibacterial compounds, pharmaceutical compositions containing them and their use as antimicrobials.

13 Claims, No Drawings

(56) References Cited

FOREIGN PATENT DOCUMENTS

| WO | WO 2006/090272 | * | 8/2006 | ........... C07D 471/04 |
|---|---|---|---|---|
| WO | WO 2007/027532 A2 | | 3/2007 | |
| WO | WO 2008/028690 A1 | | 3/2008 | |
| WO | 2008/126034 A2 | | 10/2008 | |
| WO | WO 2008/139286 A2 | | 11/2008 | |
| WO | WO 2010/081874 A1 | | 7/2010 | |
| WO | WO 2010/084152 A1 | | 7/2010 | |
| WO | WO 2011/057110 A1 | | 5/2011 | |
| WO | WO 2012/003418 A2 | | 1/2012 | |
| WO | WO 2013/068948 A1 | | 5/2013 | |
| WO | WO 2013/080156 A1 | | 6/2013 | |

OTHER PUBLICATIONS

Leopoldo et al., Structure-Affinity Relationship Study on N-[4-(4-Arylpiperazin-1-yl)butyl]arylcarboxamides as Potent and Selective Dopamine D3 Receptor Ligands, Journal of Medicinal Chemistry, vol. 45, No. 26, pp. 5727-5735 (Year: 2002).*

International Search Report dated Jan. 29, 2016 in PCT/EP2015/079352.

Thien-Duc Tran et al., "Design and optimisation of potent gp120-CD4 inhibitors", Bioorganic & Medicinal Chemistry Letters, vol. 19. No. 17, XP026456602. 2009. pp. 5250-5255.

Staven M. Bromidge et al., "6-[2-(4-Aryl-1-piperazinyl)ethyl]-2H-1,4-benzoxazin-3(4H)-ones: Dual-acting 5-HT$_1$ receptor antagonists and serotonin reuptake inhibitors", Bioorganic & Medicinal Chemistry Letters, vol. 18, No. 20, XP025562128, 2008. pp. 5653-5656.

Rahul P. Modh et al., "Design, Synthesis, Biological Evaluation, and Molecular Modeling of Coumarin-Piperazine Derivatives as Acetylcholinesterase Inhibitors", Arch. Pharm. Chem. Life Sci., vol. 346, No. 11, 2013, pp. 793-804.

George A. Jacoby, Clinical Infectious Diseases 2005;41:S120-6 (Suppl 2), 2005, pp. S120-S126.

Francis Blanche et al., "Differential Behaviors of *Staphylococcus aureus* and *Escherichia coli* Type II DNA Topoisomerases", Antimicrobial Agents and Chemotherapy, vol. 40, No. 12, 1996, pp. 2714-2720.

Office Action dated Feb. 26, 2019 issued in corresponding European patent application No. 15 808 202.4 citing documents AA and AO-AS therein.

* cited by examiner

ANTIBACTERIAL COMPOUNDS

CROSS REFERENCE TO RELATED APPLICATIONS

This application is a 371 of International Patent Application No. PCT/EP2015/079352, filed on Dec. 11, 2015, and claims priority to European Patent Application No. 14198412.0, filed on Dec. 17, 2014, both of which are incorporated herein by reference in their entireties.

FIELD OF THE INVENTION

The present invention relates to novel antibacterial compounds, pharmaceutical compositions containing them and their use as antimicrobials.

BACKGROUND OF THE INVENTION

DNA topoisomerases are enzymes involved in the modification of the DNA-supercoiling during replication or transcription. These enzymes bind to single-stranded or double-stranded DNA and cut the phosphate backbone of the DNA such that the DNA strand is untangled or unwound. At the end of the replication or transcription processes, the enzymes themselves reseal the DNA backbone.

DNA topoisomerases are classified as type I when cut a single strand of a DNA double helix and as type II when cut both strands of a DNA double helix.

Bacterial type II topoisomerases comprise DNA gyrase and topoisomerase IV (TopoIV), which are heterotetrameric enzymes concurrently present in almost all the prokaryotic cells. Both the enzymes are necessary for DNA replication and, hence, for bacterial cell growth and division.

Bacterial type II topoisomerases are a proven antibacterial target, in particular of compounds belonging to fluoroquinolone class.

Fluoroquinolones are broad-spectrum antibacterial drugs that play an important role in treatment of bacterial infections, especially hospital-acquired infections and infections in which resistance to other antibacterial classes is suspected. Fluoroquinolones act by inhibiting the DNA gyrase in Gram negative bacteria and the topoisomerase IV in Gram positive bacteria.

However, resistance to fluoroquinolones emerged in recent years due to mutations that altered either the active site of the drug targets DNA gyrase and topoisomerase IV or the drug accumulation. In addition, resistance to quinolones can be mediated by plasmids that produce the Qnr protein, which protects the quinolone targets from inhibition (G. A. Jacoby, CID, 2005:41, Suppl. 2, SD120-S126).

According to the World Health Organization, the antimicrobial resistance (AMR) is the resistance of a microorganism to an antimicrobial drug to which it was originally sensitive. Resistant bacteria are able to withstand attack by antibiotics and antibacterial drugs, so that standard treatments become ineffective and infections persist increasing risk of spread to others.

WO 02/072572, WO 2006/021448, WO 2008/139288, WO 2010/081874, WO 2010/084152, WO 2013/068948 and WO 2013/080156 disclose heterocyclic compounds endowed with antimicrobial activity.

WO 96/10568 and WO 2012/003418 disclose heterocyclic compounds endowed with other therapeutic activity.

SUMMARY OF THE INVENTION

The Applicant recognized that there is a strong and continuous need for antibacterial drugs that overcome the problem of resistant bacteria.

Thus, the Applicant faced the problem to develop new antibacterial compounds.

In particular, the Applicant faced the problem to develop new antibacterial compounds having broad spectrum of activity, i.e. useful against Gram positive and/or Gram negative bacteria.

Thus, in a first embodiment, the present invention relates to a compound of formula (I):

A-L$_1$-B-L$_2$-Y-L$_3$-C     (I)

wherein
A is a 10-membered fused bicyclic ring;
L$_1$ is σ bond, —O— or —N(R')—, wherein R' is H or (C$_{1-3}$)alkyl;
B is a divalent residue of a piperazine or piperidine ring;
L$_2$ is σ bond, —CH$_2$—, —O—, or —N(R')—, wherein R' is H or (C$_{1-3}$)alkyl;
Y is a (C$_{1-6}$)alkylenyl, (C$_{2-6}$)alkenylenyl, (C$_{2-6}$)alkynylenyl, or (C$_{3-6}$)cycloalkylenyl group, said group being optionally substituted with one or more groups selected from —OH, (C$_{1-3}$)alkyl, (C$_{3-6}$)cycloalkyl, 3- to 5-membered oxacycloalkyl, —COOR', —NR'R" wherein R' and R", identical or different each other, are hydrogen atom or (C$_{1-3}$)alkyl;
L$_3$ is —O—, —(CH$_2$)$_2$—, —N(R')—, —N(R')—C(=O)—, —N(R')—C(=S)—, —N(F)—(C$_{1-6}$)alkylenyl-, —C(=O)—N(R')—, —C(=O)—N(F)—(C$_{1-6}$)alkylenyl-, —SO$_2$—N(R')—, —N(F)—SO$_2$—, wherein R' is hydrogen atom or (C$_{1-3}$)alkyl;
C is a group having a 5- or 6-membered saturated or unsaturated ring, or a 9- or 10-membered fused bicyclic ring;
and pharmaceutically acceptable salts, enantiomers, N-oxides and quaternary ammonium salts thereof.

In a second embodiment, the present invention relates to a pharmaceutical composition comprising at least one compound of formula (I).

In a third embodiment, the present invention relates to the compounds of formula (I) for use in medicine.

In a fourth embodiment, the present invention relates to the compounds of formula (I) for use in the treatment of bacterial infections.

In a fifth embodiment, the present invention relates to a method for treating a bacterial infection, comprising the administration of a compound of formula (I) to a patient in need thereof.

According to a preferred aspect of the present invention, A is a fused bicyclic ring having the following formula (II):

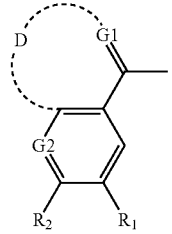

(II)

wherein
G1 and G2, identical or different each other, are CH or N;
R$_1$ is H, halogen atom, CN or CF$_3$;
R$_2$ is H, halogen atom, OH, CN, CF$_3$, (C$_{1-6}$)alkyl or (C$_{1-6}$)alkoxy;

D is a divalent group selected from

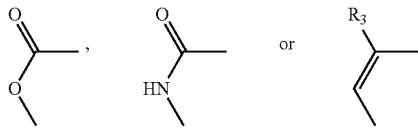

wherein $R_3$ is H, $(C_{1-6})$alkyl or $(C_{1-6})$alkoxy.

According to a preferred aspect of the present invention, A is a fused bicyclic ring having one of the following formulas:

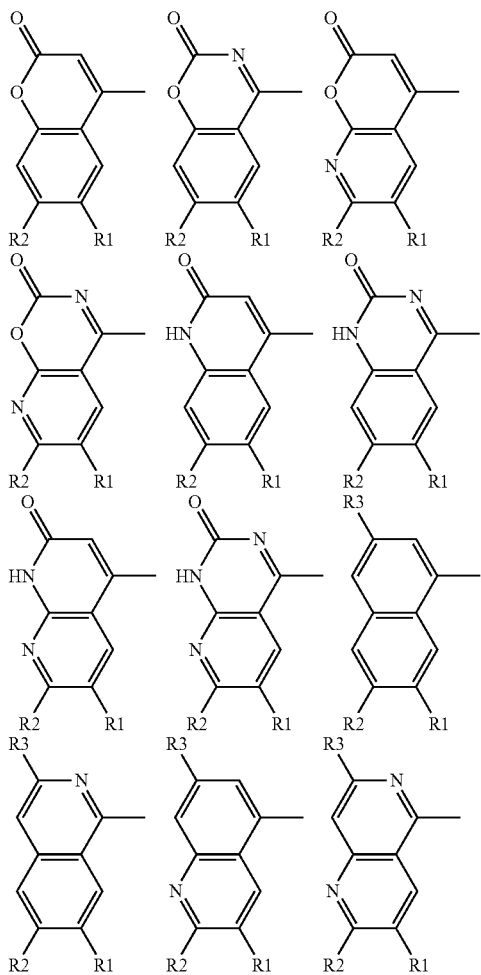

Preferably, $R_1$ is H or halogen atom. More preferably, $R_1$ is H or F.

Preferably, $R_2$ is H, halogen atom, OH, $(C_{1-3})$alkyl or $(C_{1-3})$alkoxy. More preferably, $R_2$ is H, F, Cl, OH, $CH_3$ or $OCH_3$.

Preferably, $R_3$ is H, $(C_{1-3})$alkyl or $(C_{1-3})$alkoxy. More preferably, $R_3$ is H, $CH_3$ or $OCH_3$.

Preferably, $L_1$ is a σ bond or —N(R')— wherein R' is H or methyl. More preferably, $L_1$ is a σ bond or —NH—.

According to a preferred aspect of the present invention, B is a group having the following formula (III)

(III)

wherein
G3 and G4, identical or different each other, are $C(R_4)$ or N, provided that at least one of G3 and G4 is N,
$R_4$ is hydrogen atom, —OH, —CN, —COOH, —NR'R" wherein R' and R", identical or different each other, are hydrogen atom or $(C_{1-3})$alkyl;
G5 is C(=O) or C(H)($R_5$);
$R_5$ is hydrogen atom, $CF_3$, —$(C_{1-3})$alkyl-$CF_3$, —COOR' and —CONR'R", wherein R' and R", identical or different each other, are hydrogen atom or $(C_{1-3})$alkyl.

Preferably, $R_4$ is hydrogen atom.
Preferably, $R_5$ is H, —$CH_2CF_3$, —COOR' or —CONR'R", where R' and R" are H or $CH_3$.

According to a preferred aspect of the present invention, B is a ring residue having one of the following formulas:

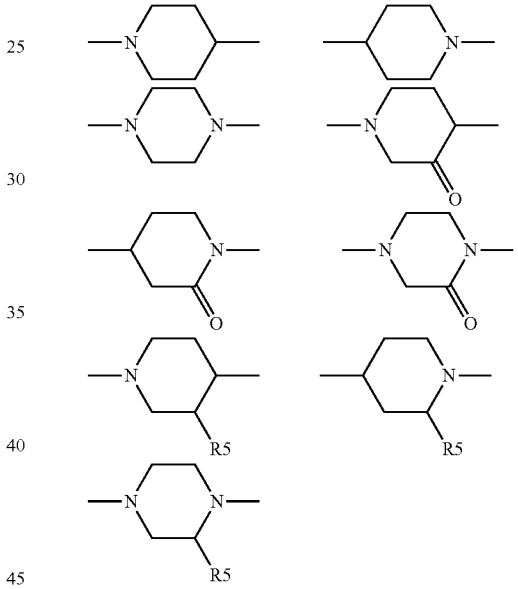

Preferably, $L_2$ is σ bond, or —NH—.
More preferably, $L_2$ is σ bond.
Preferably, Y is a $(C_{1-4})$alkylenyl, $(C_{2-4})$alkynylenyl, or $(C_{5-6})$cycloalkylenyl group, said group being optionally substituted with one or more groups selected from —OH, methyl, $(C_{3-4})$cycloalkyl, 3- or 4-membered oxacycloalkyl, —COOH, —NR'R" wherein R' and R", identical or different each other, are hydrogen atom or methyl.

More preferably, Y is a $(C_{1-4})$alkylenyl, $(C_{2-4})$alkynylenyl or cyclohexylenyl group, said group being optionally substituted with one or more hydroxy groups.

Preferably, $L_3$ is —O—, —$(CH_2)_2$—, —N(R')— wherein R' is H or $(C_{1-3})$alkyl, —NH—C(=O)—, —NH—$(C_{1-3})$alkylenyl-, —C(=O)—NH— or —C(=O)—NH—$(C_{1-3})$alkylenyl-.

More preferably, $L_3$ is —O—, —$(CH_2)_2$—, —N(R')— wherein R' is H or methyl, —NH—C(=O)—, —NH—$CH_2$—, —C(=O)—NH—, —C(=O)—NH—$CH_2$—.

According to a preferred aspect of the present invention, C is a group having one of the following formulae (IV), (V), (VI), (VII) or (VIII):

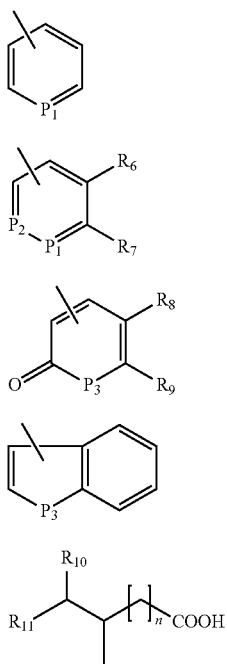

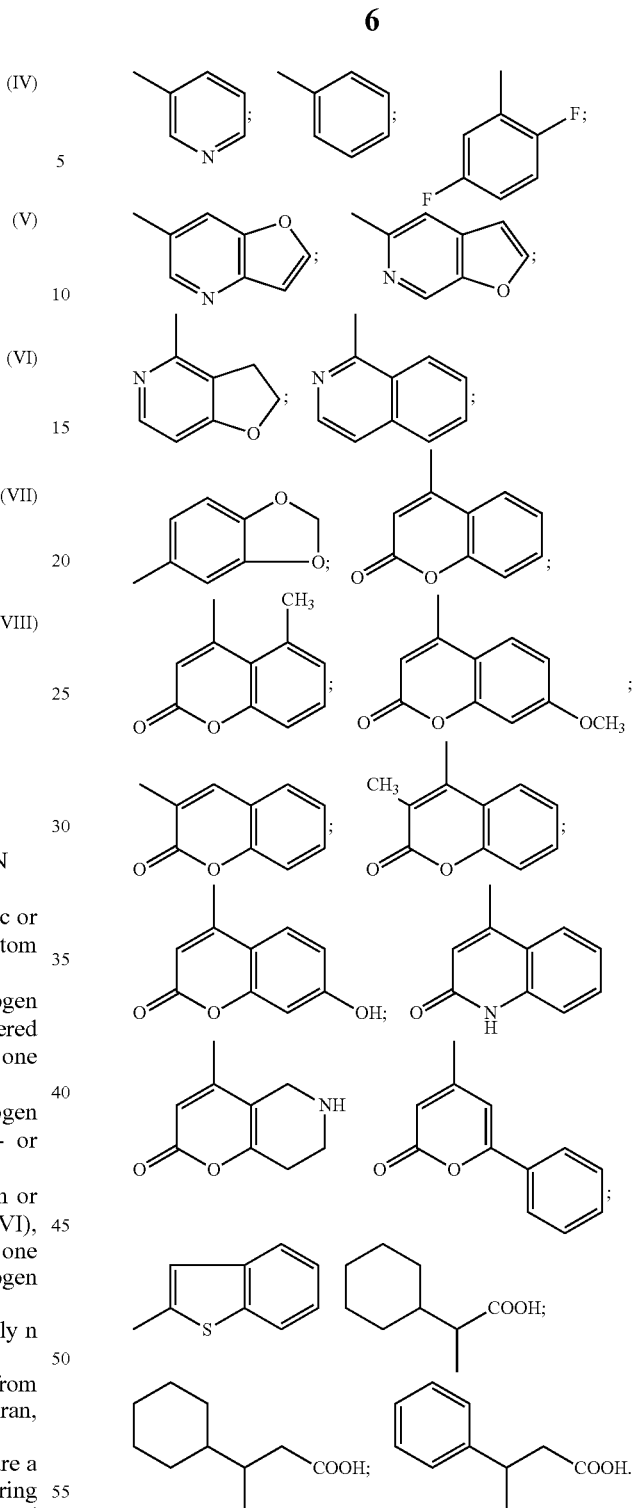

wherein n is an integer from 0 to 3

$P_1$ and $P_2$, equal or different each other, are CH or N $P_3$ is O, S or NH;

$R_6$ and $R_7$ together form a 5- or 6-membered aliphatic or aromatic ring, optionally comprising at least one heteroatom selected from N and O, $R_8$ and $R_9$, equal or different each other, are a hydrogen atom or an aryl group, or together form a 5- or 6-membered aliphatic or aromatic ring, optionally comprising at least one heteroatom selected from N and O, $R_{10}$ and $R_{11}$, equal or different each other, are a hydrogen atom, or a $(C_{1-3})$alkyl group, or together form a 5- or 6-membered aliphatic or aromatic ring, and wherein each hydrogen atom linked to a carbon or nitrogen atom forming a ring of formulae (IV), (V), (VI), (VII) or (VIII) is optionally substituted with at least one substituent selected from the group consisting of halogen atom, OH, $(C_{1-3})$alkyl or $(C_{1-3})$alkoxy.

Preferably, n is an integer from 0 to 2, more preferably n is 0 or 1.

Preferably, $R_6$ and $R_7$ together form a ring selected from the group consisting of benzene, furan, tetrahydrofuran, dioxolane, piperidine and piperazine.

Preferably, $R_8$ and $R_9$, equal or different each other, are a hydrogen atom or an aryl group, or together form a ring selected from the group consisting of benzene, pyridine, and piperidine.

Preferably, $R_{10}$ and $R_{11}$, equal or different each other, are a hydrogen atom, or a $(C_{1-3})$alkyl group, or together form a cyclohexane or an aryl ring.

Preferably, each hydrogen atom linked to a carbon or nitrogen atom forming the ring of formulae (IV), (V), (VI), (VII) or (VIII) is optionally substituted with at least one substituent selected from the group consisting of chlorine atom, fluorine atom, OH, methyl or methoxy.

According to a preferred aspect of the present invention, C is a group having one of the following formulas:

In the present description and in the following claims, the term "$(C_{1-6})$alkyl" means a linear or branched alkyl chain comprising from 1 to 6 carbon atoms, such as for example methyl, ethyl, propyl, isopropyl, n-butyl, isobutyl, sec-butyl, tert-butyl, n-pentyl, isopentyl, neopentyl, tert-pentyl, sec-pentyl, 3-pentyl, n-hexyl, isohexyl, neo-hexyl, 3-methyl-pentyl, 2,3-dimethylbutyl.

In the present description and in the following claims, the term "$(C_{1-3})$alkyl" means a linear or branched alkyl chain comprising from 1 to 3 carbon atoms, such as for example methyl, ethyl, propyl, isopropyl.

In the present description and in the following claims, the term "$(C_{1-6})$alkoxy" means a linear or branched alkoxy chain comprising from 1 to 6 carbon atoms, such as for example methoxy, ethoxy, propoxy, isopropoxy, n-butoxy, isobutoxy, sec-butoxy, tert-butoxy, n-pentoxy, isopentoxy, neopentoxy, tert-pentoxy, sec-pentoxy, 3-pentoxy, n-hexoxy, isohexoxy, neo-hexoxy, 3-methyl-pentoxy, 2,3-dimethy-lbutoxy.

In the present description and in the following claims, the term "$(C_{1-3})$alkoxy" means a linear or branched alkoxy chain comprising from 1 to 3 carbon atoms, such as for example methoxy, ethoxy, propoxy, isopropoxy.

In the present description and in the following claims, the term "$(C_{1-6})$alkylenyl" means a divalent linear or branched alkyl chain comprising from 1 to 6 carbon atoms, such as for example methylenyl (—$CH_2$—), ethylenyl (—$CH_2CH_2$—), propylenyl (—$CH_2CH_2CH_2$—), butylenyl (—$CH_2CH_2CH_2CH_2$—), pentylenyl (—$CH_2CH_2CH_2CH_2CH_2$—) or hexylenyl (—$CH_2CH_2CH_2CH_2CH_2CH_2$—).

In the present description and in the following claims, the term "$(C_{1-4})$alkylenyl" means a divalent linear or branched alkyl chain comprising from 1 to 4 carbon atoms, such as for example methylenyl (—$CH_2$—), ethylenyl (—$CH_2CH_2$—), propylenyl (—$CH_2CH_2CH_2$—), butylenyl (—$CH_2CH_2CH_2CH_2$—).

In the present description and in the following claims, the term "$(C_{2-6})$alkenylenyl" means a divalent linear or branched alkylen chain comprising from 2 to 6 carbon atoms, such as for example ethenylenyl (—CH=CH—), propenylenyl (—CH=CH—$CH_2$— or —C($CH_3$)=CH—) or butenylenyl (—CH=CH—$CH_2CH_2$— or —$CH_2$CH=CH—$CH_2$— or —C($CH_3$)=CH—$CH_2$—).

In the present description and in the following claims, the term ($C_{2-6}$)alkynylenyl means a divalent linear or branched alkynyl chain comprising from 2 to 6 carbon atoms, such as for example ethynylenyl (—C≡C—), propynylenyl (—C≡C—$CH_2$— or —$CH_2$—C≡C—), butynylenyl (—C≡C—$CH_2CH_2$— or —$CH_2$—C≡C—$CH_2$— or —C($CH_3$)—C≡C—), pentynylenyl (—C≡C—$CH_2CH_2CH_2$— or —$CH_2CH_2$—C≡C—$CH_2$— or —C($CH_2CH_3$)—C≡C—), or hexynylenyl (—C≡C—$CH_2CH_2CH_2CH_2$— or —$CH_2CH_2$C≡C—$CH_2CH_2$— or —$CH_2CH_2$C($CH_3$)—C≡C—).

In the present description and in the following claims, the term ($C_{2-4}$)alkynylenyl means a divalent linear or branched alkynyl chain comprising from 2 to 4 carbon atoms, such as for example ethynylenyl (—C≡C—), propynylenyl (—C≡C—$CH_2$— or —$CH_2$—C≡C—), butynylenyl (—C≡C—$CH_2CH_2$— or —$CH_2$—C≡C—$CH_2$— or —C($CH_3$)—C≡C—).

In the present description and in the following claims, the term "$(C_{3-6})$cycloalkylenyl" means a divalent cycloalkyl group comprising from 3 to 6 carbon atoms, such as cyclopropylenyl, cyclobutylenyl, cyclopentylenyl and cyclohexylenyl In the present description and in the following claims, the term "$(C_{5-6})$cycloalkylenyl" means a divalent cycloalkyl group comprising from 4 to 6 carbon atoms, such as cyclopentylenyl and cyclohexylenyl.

In the present description and in the following claims, the term "$(C_{3-6})$cycloalkyl" means a cycloalkyl group comprising from 3 to 6 carbon atoms, such as cyclopropyl, cyclobutyl, cyclopentyl and cyclohexyl.

In the present description and in the following claims, the term "$(C_{3-4})$cycloalkyl" means a cycloalkyl group comprising 3 or 4 carbon atoms, such as cyclopropyl and cyclobutyl.

In the present description and in the following claims, the expression "3- to 5-membered oxacycloalkyl" means a cycloalkyl group comprising at least one O atom and from 2 to 4 carbon atoms.

In the present description and in the following claims, the expression "3- or 4-membered oxacycloalkyl" means a cycloalkyl group comprising at least one O atom and from 2 to 3 carbon atoms.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Thus, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereomers by crystallization followed by liberation of the optically active bases from these salts. A different process for separation of optical isomers involves the use of a chiral chromatography column optimally chosen to maximize the separation of the enantiomers. Still another method involves synthesis of covalent diastereomers by reacting compounds of the invention with an optically pure acid in an activated form or an optically pure isocyanate. The synthesized diastereomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

The compounds of this invention can exist in radiolabeled form, i.e., said compounds may contain one or more atoms containing an atomic mass or mass number different from the atomic mass or mass number ordinarily found in nature. Radioisotopes of hydrogen, carbon, phosphorous, fluorine and chlorine include $^3H$, $^{14}C$, $^{32}P$, $^{35}S$, $^{18}F$ and $^{36}Cl$ respectively. Compounds of this invention which contain those radioisotopes and/or other radioisotopes of other atoms are within the scope of this invention. Tritiated, i.e., $^3H$, and carbon-14, i.e., $^{14}C$, radioisotopes are particularly preferred for their ease of preparation and detectability.

Radiolabeled compounds of this invention can generally be prepared by methods well known to those skilled in the art. Conveniently, such radiolabeled compounds can be prepared by carrying out the procedures disclosed herein except substituting a readily available radiolabeled reagent for a non-radiolabelled reagent.

In a second embodiment, the present invention relates to a pharmaceutical composition comprising at least one compound of formula (I) as described above, a salt thereof with a pharmaceutically acceptable organic or inorganic acid or base, or an enantiomer thereof, or a quaternary ammonium salt thereof, or a N-oxide thereof, and at least one inert pharmaceutically acceptable excipient.

Preferably, the pharmaceutical composition of the present invention is prepared in suitable dosage forms.

Examples of suitable dosage forms are tablets, capsules, coated tablets, granules, solutions and syrups for oral administration; solutions, pomade and ointment for topical administration; medicated patches for transdermal administration; suppositories for rectal administration and injectable sterile solutions. Other suitable dosage forms are those with sustained release and those based on liposomes for oral, injectable or transdermal administration. The pharmaceutical compositions of this invention may also be administered by nasal aerosol or inhalation or delivered by implantation (e.g., surgically), such as with an implantable or indwelling device like a stent.

Other suitable dosage forms are those with sustained release and those based on liposomes for oral, injectable or transdermal administration.

The dosage forms of the pharmaceutical composition of the present invention can be prepared by techniques that are familiar to a pharmaceutical chemist, and comprise mixing, granulation, compression, dissolution, sterilization and the like.

Typically, the amount of compound of formula (I) or of the pharmaceutically acceptable quaternary ammonium salt, N-oxide and salt thereof in the pharmaceutical composition of the present invention will be between 0.01 mg to 1,500 mg, preferably between 0.1 mg and 500 mg and more preferably between 1 mg and 200 mg.

Typically, the amount of compound of formula (I) in the pharmaceutical composition of the present invention will be such to ensure a level of administration from 0.001 to 20 mg/kg/day. Preferably, the level of administration is from 0.01 to 7.5 mg/kg/day, more preferably from 0.1 to 5 mg/kg/day, and most preferably from 0.5 to 2.5 mg/kg/day.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, and the patient's disposition to the disease and the judgment of the treating physician.

The pharmaceutical compositions of this invention may be administered orally, parenterally, by inhalation spray, topically, rectally, nasally, buccally, vaginally or via an implanted reservoir. The term parenteral as used herein includes subcutaneous, intracutaneous, intravenous, intramuscular, intra-articular, intrasynovial, intrasternal, intrathecal, intralesional and intracranial injection or infusion techniques.

As mentioned above, depending on the nature of the substituents, the compound of formula (I) may form addition salts with a pharmaceutically acceptable organic or inorganic acid or base.

Typical examples of suitable physiologically acceptable inorganic acids are hydrochloric acid, hydrobromic acid, sulfuric acid, phosphoric acid and nitric acid.

Typical examples of suitable physiologically acceptable organic acids are acetic acid, ascorbic acid, benzoic acid, citric acid, fumaric acid, lactic acid, maleic acid, methanesulfonic acid, oxalic acid, para-toluenesulfonic acid, benzenesulfonic acid, succinic acid, tannic acid and tartaric acid.

Typical examples of suitable physiologically acceptable inorganic bases are hydroxides, carbonates and hydrogen carbonates of ammonium, calcium, magnesium, sodium and potassium, for instance ammonium hydroxide, calcium hydroxide, magnesium carbonate, sodium hydrogen carbonate and potassium hydrogen carbonate.

Typical examples of suitable physiologically acceptable organic bases are: arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, N-methylglucamine, glucamine, glucosamine, histidine, N-(2-hydroxyethyl)-piperidine, N-(2-hydroxyethyl)pyrrolidine, isopropylamine, lysine, methylglucamine, morpholine, piperazine, piperidine, theobromine, triethylamine, trimethylamine, tripropylamine and tromethamine.

As described herein, the pharmaceutical composition of the present invention comprises a compound of the invention together with a pharmaceutically acceptable excipient, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired.

Some examples of materials which can serve as pharmaceutically acceptable excipient include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, other non-toxic compatible lubricants such as sodium lauryl sulfate and magnesium stearate, coloring agents, releasing agents, coating agents, sweetening, flavoring and perfuming agents, preservatives and antioxidants.

The terms "pharmaceutically acceptable" and "physiologically acceptable" are intended to define, without any particular limitation, any material suitable for preparing a pharmaceutical composition to be administered to a living being.

In a third embodiment, the present invention relates to the compounds of formula (I) for use in medicine.

In a fourth embodiment, the present invention relates to the compounds of formula (I) for use in the treatment of bacterial infections.

In a fifth embodiment, the present invention relates to a method for treating a bacterial infection, comprising the administration of a compound of formula (I) to a patient in need thereof.

Preferably, said bacterial infection is a skin infection, a mucosal infection, a gynaecological infection, a respiratory tract infection (RTI), a CNS infections, a gastro-intestinal infection, a bone infection, a cardiovascular infection, a sexually transmitted infection, or a urinary tract infection.

More in particular, said bacterial infection is a acute exacerbation of chronic bronchitis (ACEB), an acute otitis media, an acute sinusitis, an infection caused by drug resistant bacteria, a catheter-related sepsis, a chancroid, a *chlamydia*, a community-acquired pneumonia (CAP), a complicated skin and skin structure infection, an uncomplicated skin and skin structure infection, an endocarditis, a febrile neutropenia, a gonococcal cervicitis, a gonococcal urethritis, a hospital-acquired pneumonia (HAP), a osteomyelitis, a sepsis, a syphilis, a ventilator-associated pneumonia, an intraabdominal infections, a gonorrhoeae, a meningitis, a tetanus, or a tuberculosis.

Even more, said bacterial infection can be an atherosclerosis or cardiovascular disease related to infection by *Helicobacter pylori* or *Chlamydia* pneumonia; a blood and tissue infections, including endocarditis and osteomyelitis, caused by *S. aureus*, *S. haemolyticus*, *E. faecalis*, *E. faecium*, *E. durans*, including strains resistant to known antibacterials such as, but not limited to, beta-lactams, vancomycin, aminoglycosides, quinolones, chloramphenicol, tetracyclines and macrolides; bronchitis; catheter-related sepsis; chancroid; *chlamydia*; community-acquired pneumonia; disseminated *Mycobacterium avium* complex (MAC) disease related to infection by *Mycobacterium avium*, or *Mycobacterium intracellulare*; endocarditis; febrile neutropenia; gas gangrene related to infection by *Clostridium perfringens* or *Bacteroides* spp; gastroenteritis infection; glomerulonephritis related to infection by *Streptococcus pyogenes*, Groups C and G streptococci, *Corynebacterium diphtheriae*, or *Actinobacillus haemolyticum*; gonococcal cervicitis; gonococcal urethritis; gynaecological infection; hospital-acquired pneumonia (HAP); infection caused by drug resistant bacteria; infections caused by *Mycobacterium tuberculosis*, *M. leprae*, *M. paratuberculosis*, *M. kansasii*, or *M. chelonei*; intestinal protozoa related to infection by *Cryptosporidium* spp; Lyme disease related to infection by *Borrelia burgdorferi*; conjunctivitis, keratitis, and dacrocystitis related to infection by *Chlamydia trachomatis*, *Neisseria gonorrhoeae*, *S. aureus*, *S. pneumoniae*, *S. pyogenes*, *H. injluenzae*, or *Listeria* spp.; mastoiditis related to infection by *Streptococcus pneumoniae*, *Haemophilus injluenzae*, *Moraxella catarrhalis*, *Staphylococcus aureus*, *Enterococcus faecalis*, *E. faecium*, *E. casseliflavus*, *S. epidermidis*, *S. haemolyticus*, or *Peptostreptococcus* spp; odontogenic infection related to infection by viridans streptococci; osteomyelitis; otitis media; persistent cough related to infection by *Bordetella pertussis*; pharyngitis; puerperal fever related to infection by *Staphylococcus aureus*, coagulase-negative staphylococci *Streptococcus pyogenes*, *Streptococcus agalactiae*, Streptococcal groups C-F (minute colony streptococci), viridans streptococci *Corynebacterium minutissimum*, *Clostridium* spp., or *Bartonella henselae*; respiratory tract infections related to infection by *Mycoplasma pneumoniae*, *Legionella pneumophila*, *Streptococcus pneumoniae*, *Haemophilus injluenzae*, or *Chlamydia pneumoniae*; rheumatic fever; sepsis; sexually transmitted diseases related to infection by *Chlamydia trachomatis*, *Haemophilus ducreyi*, *Treponema pallidum*, *Ureaplasma urealyticum*, or *Neiseria gonorrhoeae*; sinusitis; syphilis; systemic febrile syndromes related to infection by *Borrelia recurrentis*; tonsillitis; toxin diseases related to infection by *S. aureus* (food poisoning and toxic shock syndrome), or Groups A, B, and C streptococci; ulcers related to infection by *Helicobacter pylori*; uncomplicated acute urinary tract infections related to infection by *Staphylococcus aureus* coagulase-negative staphylococcal species, or *Enterococcus* spp.; uncomplicated skin and soft tissue infections and abscesses; urethritis and cervicitis; urinary tract infection; central nervous system infections; device related infections caused by staphylococci; muscoleskeletal infection caused by staphylococci; Shiga toxin-producing *E. coli*; *Haemophilus influenzae* (invasive disease); legionellosis; psittacosis/ornithosis clamydia psittaci; salmonellosis caused by *salmonella* spp.; shigellosis by *shigella* spp.; streptococcal toxic shock syndrome; staphylococcal toxic shock syndrome; and typhoid fever caused by *Salmonella typhi*.

The bacterial infection can be an infection caused by *Acinetobacter* spp, *Bacteroides* spp, *Burkholderia* spp, *Campylobacter* spp, *Chlamydia* spp, *Chlamydophila* spp, *Clostridium* spp, *Enterobacter* spp, *Enterococcus* spp, *Escherichia* spp, *Gardnerella* spp, *Haemophilus* spp, *Helicobacter* spp, *Klebsiella* spp, *Legionella* spp, *Moraxella* spp, *Morganella* spp, *Mycoplasma* spp, *Neisseria* spp, *Peptostreptococcus* spp, *Proteus* spp, *Pseudomonas* spp, *Salmonella* spp, *Serratia* spp, *Staphylococcus* spp, *Streptococcus* spp, *Stenotrophomonas* spp, *Ureaplasma* spp, aerobes, obligate anaerobes, facultative anaerobes, gram-positive bacteria, gram-negative bacteria, gram-variable bacteria, and atypical respiratory pathogens.

More in particular, the bacterial infection can be an infection caused by *Acinetobacter baumanii*, *Acinetobacter haemolyticus*, *Acinetobacter junii*, *Acinetobacter johnsonii*, *Acinetobacter lwoffi*, *Bacteroides bivius*, *Bacteroides fragilis*, *Burkholderia cepacia*, *Campylobacter jejuni*, *Chlamydia pneumoniae*, *Chlamydia urealyticus*, *Chlamydophila pneumoniae*, *Clostridium difficile*, *Enterobacter aerogenes*, *Enterobacter cloacae*, *Enterococcus faecalis*, *Enterococcus faecium*, *Escherichia coli*, *Gardnerella vaginalis*, *Haemophilus parainfluenzae*, *Haemophilus influenzae*, *Helicobacter pylori*, *Klebsiella pneumoniae*, *Legionella pneumophila*, Methicillin-resistant *Staphylococcus aureus*, Methicillin-susceptible *Staphylococcus aureus*, *Moraxella catarrhalis*, *Morganella morganii*, *Mycoplasma pneumoniae*, *Neisseria gonorrhoeae*, Penicillin-resistant *Streptococcus pneumoniae*, Penicillin-susceptible *Streptococcus pneumoniae*, *Peptostreptococcus magnus*, *Peptostreptococcus micros*, *Peptostreptococcus anaerobius*, *Peptostreptococcus asaccharolyticus*, *Peptostreptococcus prevotii*, *Peptostreptococcus tetradius*, *Peptostreptococcus vaginalis*, *Proteus mirabilis*, *Pseudomonas aeruginosa*, Quinolone-Resistant *Staphylococcus aureus*, Quinolone-Resistant *Staphylococcus epidermis*, *Salmonella typhi*, *Salmonella paratyphi*, *Salmonella enteritidis*, *Salmonella typhimurium*, *Serratia marcescens*, *Staphylococcus aureus*, *Staphylococcus epidermidis*, *Staphylococcus saprophyticus*, *Streptococcus agalactiae*, *Streptococcus pneumoniae*, *Streptococcus pyogenes*, *Stenotrophomonas maltophilia*, *Ureaplasma urealyticum*, Vancomycin-Resistant *Enterococcus faecium*, Vancomycin-Resistant *Enterococcus faecalis*, Vancomycin-Resistant *Staphylococcus aureus*, and Vancomycin-Resistant *Staphylococcus epidermis*.

Examples of compounds according to the present invention are provided in the following Table 1.

TABLE 1

| No. | A | L$_1$ | B | L$_2$ | Y | L$_3$ | C |
|---|---|---|---|---|---|---|---|
| 2 | 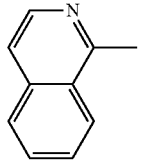 | σ bond | 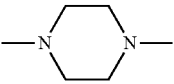 | σ bond | —(CH$_2$)$_3$— | 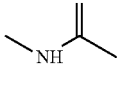 | 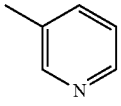 |

TABLE 1-continued
| No. | A | L₁ | B | L₂ | Y | L₃ | C |
|---|---|---|---|---|---|---|---|
| 3 | 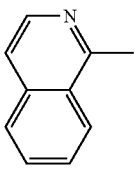 | σ bond | 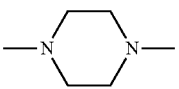 | σ bond | —(CH₂)₃— | 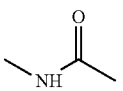 | 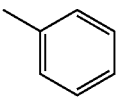 |
| 4 | 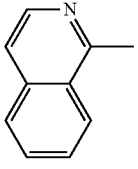 | σ bond |  | σ bond | —(CH₂)₃— | 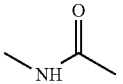 | 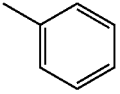 |
| 14 | 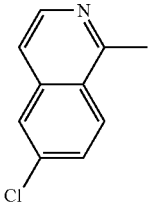 | σ bond |  | σ bond | —(CH₂)₃— | 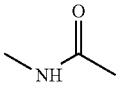 | 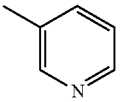 |
| 21 | 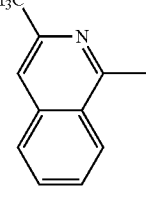 | σ bond |  | σ bond | —(CH₂)₃— | 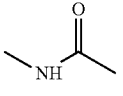 | 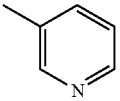 |
| 31 | 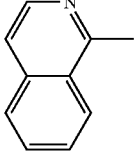 | σ bond |  | σ bond | —(CH₂)₃— | 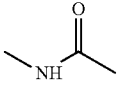 | 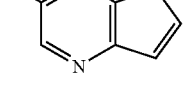 |
| 35 | 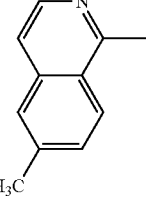 | σ bond |  | σ bond | —(CH₂)₃— | 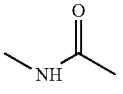 | 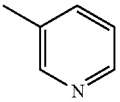 |
| 36 | 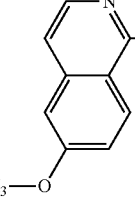 | σ bond |  | σ bond | —(CH₂)₃— | 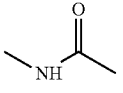 | 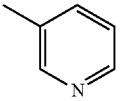 |
| 38 | 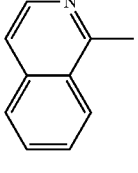 | σ bond |  | σ bond | —(CH₂)₃— | —NH—CH₂— | 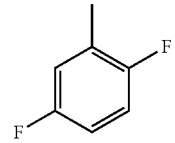 |

TABLE 1-continued
| No. | A | L₁ | B | L₂ | Y | L₃ | C |
|---|---|---|---|---|---|---|---|
| 39 | 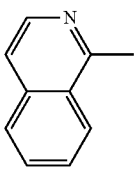 | σ bond | 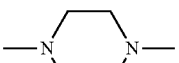 | σ bond | —(CH₂)₃— | 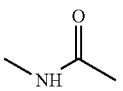 | 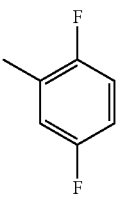 |
| 42 | 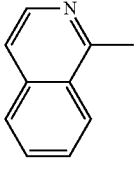 | σ bond |  | σ bond | —(CH₂)₃— | 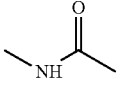 | 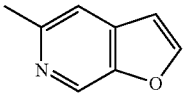 |
| 43 | 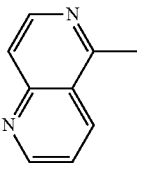 | σ bond | 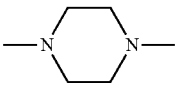 | σ bond | —(CH₂)₃— | 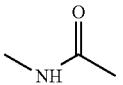 | 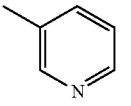 |
| 45 | 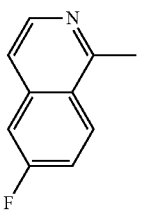 | σ bond | 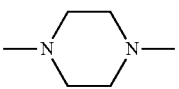 | σ bond | —(CH₂)₃— | 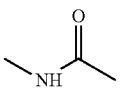 | 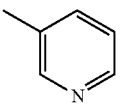 |
| 50 | 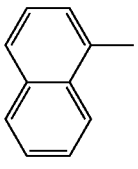 | σ bond |  | σ bond | —(CH₂)₃— | —NH— | 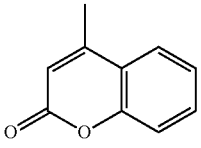 |
| 53 | 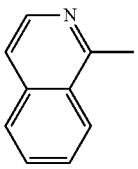 | σ bond | 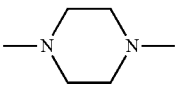 | σ bond | —(CH₂)₃— | —N(CH₃)— | 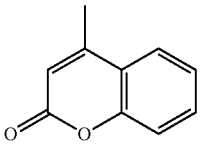 |
| 58 | 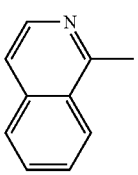 | σ bond | 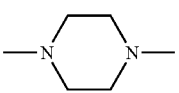 | σ bond | —(CH₂)₃— | —NH— | 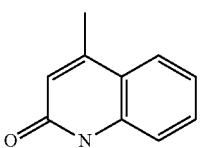 |
| 60 | 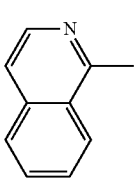 | σ bond | 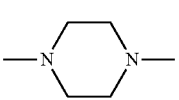 | σ bond | —(CH₂)₃— | —NH— | 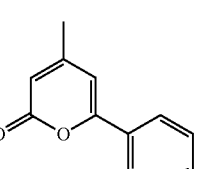 |

TABLE 1-continued
| No. | A | L₁ | B | L₂ | Y | L₃ | C |
|---|---|---|---|---|---|---|---|
| 68 | 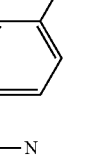 | σ bond |  | σ bond | —(CH₂)₃— | —NH— | 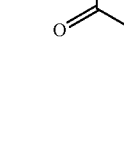 |
| 70 | 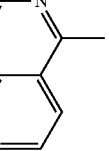 | σ bond | 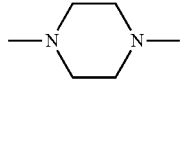 | σ bond | —(CH₂)₃— | —O— | 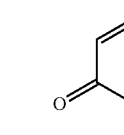 |
| 71 | 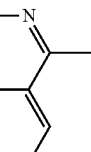 | σ bond | 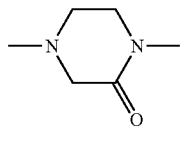 | σ bond | —(CH₂)₃— | —NH— | 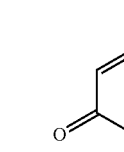 |
| 74 | 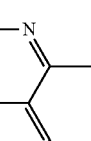 | σ bond | 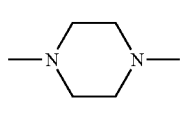 | σ bond | 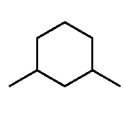 | —NH— | 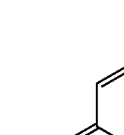 |
| 75 | 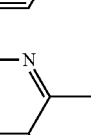 | σ bond | 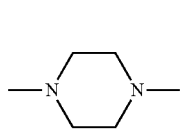 | σ bond | —(CH₂)₂— | 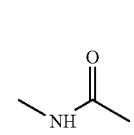 | 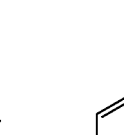 |
| 81 | 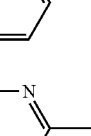 | σ bond | 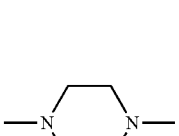 | σ bond | —(CH₂)₃— | —NH— |  |
| 82 | 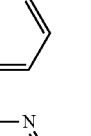 | σ bond | 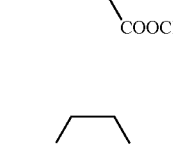 | σ bond | —(CH₂)₃— | —NH— | 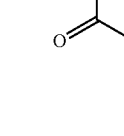 |
| 83 | 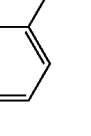 | σ bond | 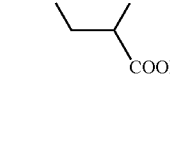 | σ bond | —(CH₂)₃— | —NH— | 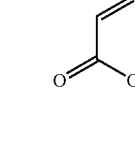 |

TABLE 1-continued

| No. | A | L₁ | B | L₂ | Y | L₃ | C |
|---|---|---|---|---|---|---|---|
| 85 | 1-methylisoquinoline | σ bond | piperazine | σ bond | —(CH₂)₃— | —NH— | 4-methyl-7-methoxy-2H-chromen-2-one |
| 87 | 1-methylisoquinoline | σ bond | piperazine | σ bond | —(CH₂)₃— | —NH— | 3-methyl-2H-chromen-2-one |
| 96 | 7-fluoro-1-methylisoquinoline | σ bond | piperazine | σ bond | —(CH₂)₃— | —NH— | 4,5-dimethyl-2H-chromen-2-one |
| 97 | 7-fluoro-1-methylisoquinoline | σ bond | piperazine | σ bond | —(CH₂)₃— | —NH— | 3,4-dimethyl-2H-chromen-2-one |
| 101 | 7-fluoro-1-methylisoquinoline | σ bond | piperazine | σ bond | —(CH₂)₂— | —NHC(O)— | 4-methyl-2H-chromen-2-one |
| 107 | 7-fluoro-1-methylisoquinoline | σ bond | piperazine | σ bond | —(CH₂)₃— | —NH— | 4-methyl-7-hydroxy-2H-chromen-2-one |
| 117 | 4-methyl-2H-chromen-2-one | —NH— | piperidine | σ bond | —CH₂— | —NHC(O)— | 1-methylisoquinoline |

TABLE 1-continued
| No. | A | L₁ | B | L₂ | Y | L₃ | C |
|---|---|---|---|---|---|---|---|
| 118 | 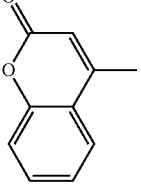 | —NH— | 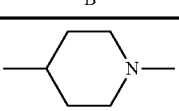 | σ bond | —CH₂— | 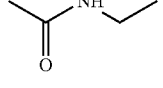 | 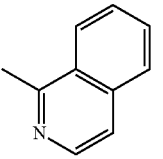 |
| 119 | 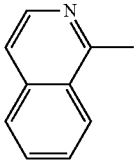 | σ bond | 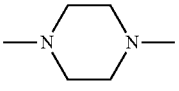 | σ bond | —(CH₂)₃— | —NH—CH₂— | 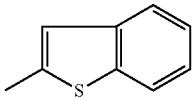 |
| 120 | 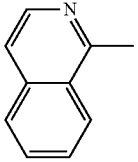 | σ bond |  | σ bond | —(CH₂)₃— | —NH—CH₂— | 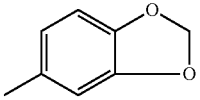 |
| 122 | 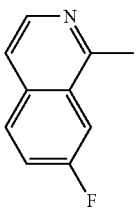 | σ bond |  | σ bond | —(CH₂)₃— | —NH— | 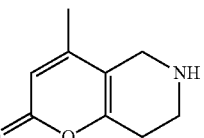 |
| 123 | 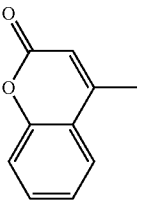 | —NH— | 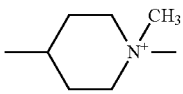 | σ bond | —(CH₂)— | —(CH₂)₂— | 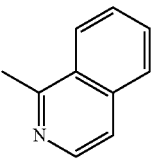 |
| 128 | 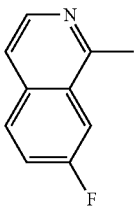 | σ bond | 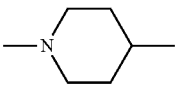 | σ bond | 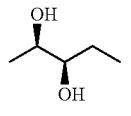 | —NH— | 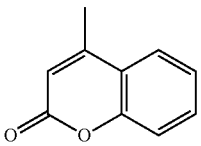 |
| 129 | 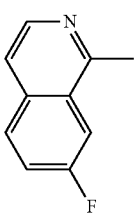 | σ bond |  | σ bond | 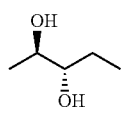 | —NH— | 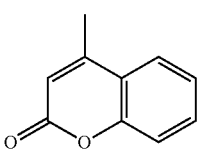 |
| 130 | 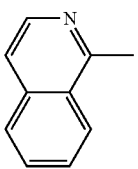 | σ bond |  | σ bond | —(CH₂)₂— | —NH—CH₂— | 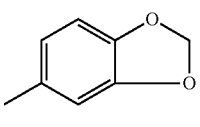 |

TABLE 1-continued
| No. | A | L₁ | B | L₂ | Y | L₃ | C |
|---|---|---|---|---|---|---|---|
| 132 | 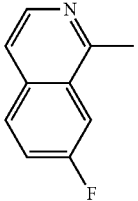 | σ bond |  | σ bond | 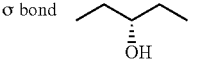 | —NH— | 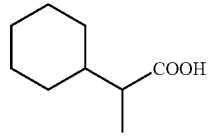 |
| 133 | 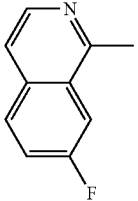 | σ bond | 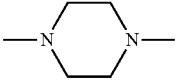 | σ bond | 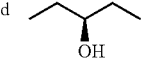 | —NH— | 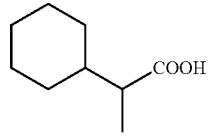 |
| 136 | 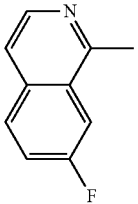 | σ bond | 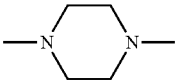 | σ bond | 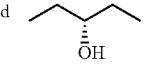 | —NH— | 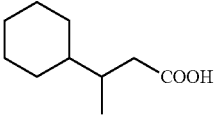 |
| 137 | 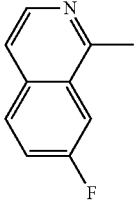 | σ bond | 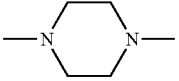 | σ bond | 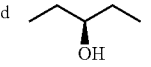 | —NH— | 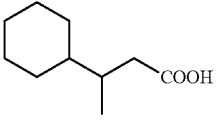 |
| 138 | 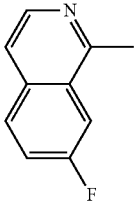 | σ bond | 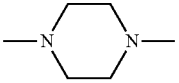 | σ bond | 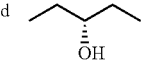 | —NH— | 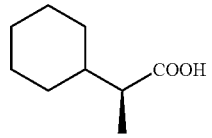 |
| 139 | 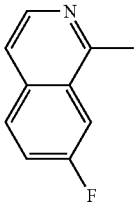 | σ bond | 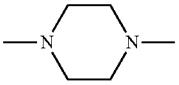 | σ bond | 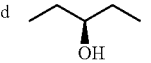 | —NH— | 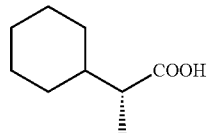 |
| 140 | 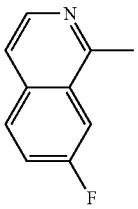 | σ bond |  | σ bond | 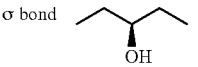 | —NH— | 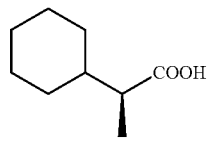 |

TABLE 1-continued

| No. | A | $L_1$ | B | $L_2$ | Y | $L_3$ | C |
|---|---|---|---|---|---|---|---|
| 141 | 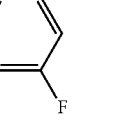 | σ bond |  | σ bond |  | —NH— |  |
| 142 | 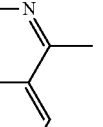 | σ bond | 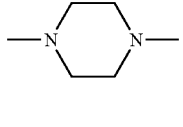 | σ bond | 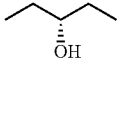 | —NH— | 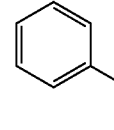 |
| 167 | 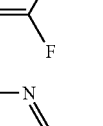 | σ bond | 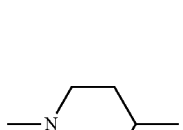 | —NH— | —(CH$_2$)$_2$— | —NH— | 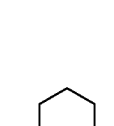 |
| 189 | 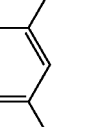 | σ bond | 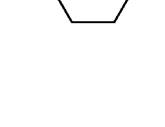 | —NH— | —(CH$_2$)$_2$— | —NH— | 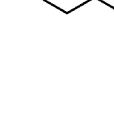 |
| 190 | 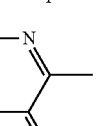 | σ bond | 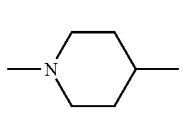 | —NH— | —(CH$_2$)$_2$— | —NH— | 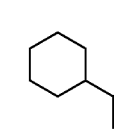 |
| 191 | 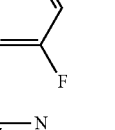 | σ bond | 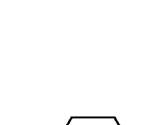 | —NH— | —(CH$_2$)$_2$— | —NH— |  |

The above compounds can be prepared as explained in the synthetic examples below.

The man skilled in the art has a well-established literature of heterocyclic and other relevant chemical transformations, recovery and purification technologies to draw upon, in combination with the information contained in the examples which follow, for guidance on synthetic strategies, protecting groups, and other materials and methods useful for the synthesis, recovery and characterization of the compounds of this invention, including compounds containing the various choices for A L$_1$, B, L$_2$, Y, L$_3$ and C.

Various synthetic approaches may be used to produce the compounds described herein, including those approaches depicted schematically below. The man skilled in the art will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art.

Also, one may chose reagents enriched for a desired isotope, e.g. tritium in place of hydrogen, to create compounds of this invention containing such isotope(s). Compounds containing tritium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

The compounds of the this invention can be synthesized using the methods described below, together with synthetic methods known in the art of synthetic organic chemistry, or by a variation thereon as appreciated by those skilled in the art. Preferred methods include, but are not limited to those described below. The reactions are performed in a solvent appropriate to the reagents and materials employed and suitable for the transformation being effected. It will be understood by those skilled in the art of organic synthesis that the functionality present on the molecule should be consistent the transformations proposed. This will sometimes require some judgment to modify the order of the synthetic steps or to select one particular process scheme over another in order to obtain a desired compound of the invention.

A compound of the present invention could be prepared as outlined in the synthetic pathways described hereinafter and via standard methods known to those skilled in the art.

EXAMPLES

List of the abbreviations used in the synthetic pathways described hereinafter:
Boc—tert-butyl carbamate
cHex—cyclohexane
CV—column volume
DCM—dichloromethane
DIPEA—N,N-diisopropylethylamine
DMA—N,N-dimethylacetamide
DMF—N,N-dimethylformamide
DMSO—dimethyl sulfoxide
Et$_2$O—diethyl ether
EtOAc—ethylacetate
EtOH—ethanol
HATU—1-[bis(dimethylamino)methylene]-1H-1,2,3-triazolo[4,5-b]pyridinium 3-oxid hexafluorophosphate
HBTU—N,N,N',N'-tetramethyl-O-(1H-benzotriazol-1-yl)uronium hexafluorophosphate
LC—liquid chromatography
MeCN—acetonitrile
MeOH—methanol
MS—mass spectroscopy
TEA—triethylamine
TFA—trifluoroacetic acid
THF—tetrahydrofuran
Pd/C—palladium on activated charcoal
Pd(dba)$_2$—bis(dibenzylideneacetone)palladium(0)
Pd(OAc)$_2$—palladium(II) acetate
UPLC—ultra high performance liquid chromatography Preparation of compound 2: N-{3-[4-(isoquinolin-1-yl)piperazin-1-yl]propyl}pyridine-3-carboxamide hydrochloride Compound 2 was prepared as described hereinbelow.

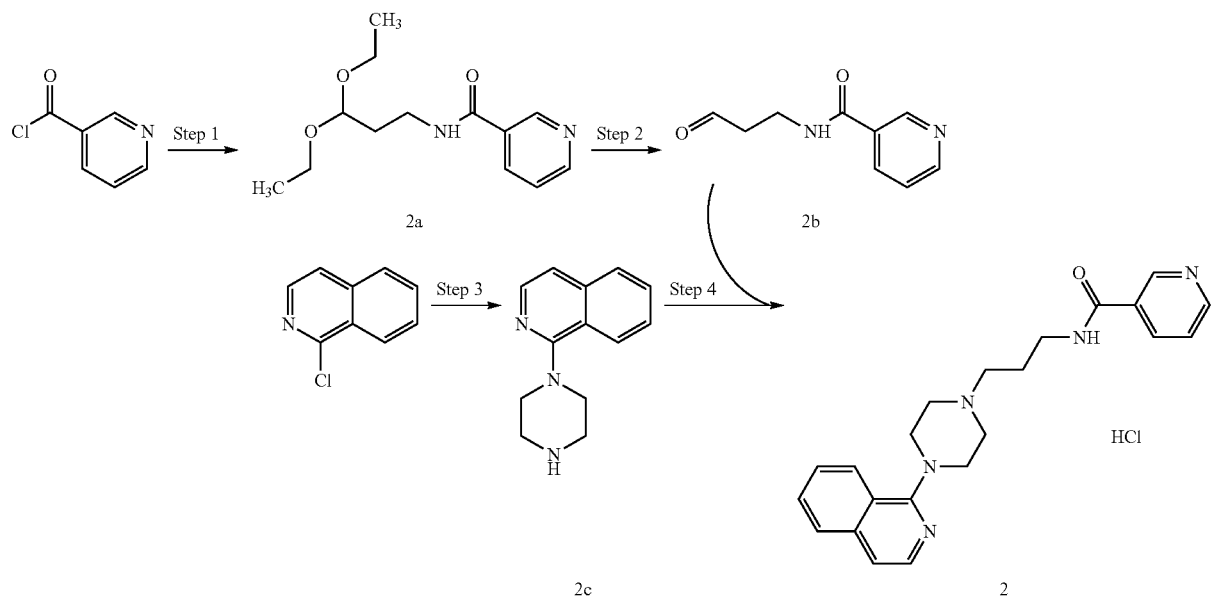

Step 1: N-(3,3-diethoxypropyl)pyridine-3-carboxamide (2a)

Pyridine-3-carbonyl chloride (10 g, 56.2 mmoles, 1 eq.) was dissolved in DMF (50 mL) and CH$_3$CN (200 mL) with TEA (19.5 mL, 140.4 mmoles, 2.5 eq.). 3,3-diethoxypropan-1-amine (10.35 g, 70.2 mmoles, 1.25 eq.) in CH$_3$CN (20 mL) was added at 0° C. The solution was stirred overnight then was concentrated, diluted with DCM and washed with sat. NaHCO$_3$ and brine. The organic phase was then separated, dried over sodium sulphate and evaporated in vacuum to obtain N-(3,3-diethoxypropyl)pyridine-3-carboxamide 2a (6.8 g, Y=45%). LC-MS (M-H+): 253.0.

Step 2: N-(3-oxopropyl)pyridine-3-carboxamide (2b)

Intermediate 2a (500 mg, 1.98 mmoles, 1 eq.) was dissolved in DCM (5 mL). TFA (2 mL) was added, and after 3 h the solution was concentrated and washed several times with toluene, diethyl ether and ethyl acetate to afford 900 mg of N-(3-oxopropyl)pyridine-3-carboxamide 2b (Y=quant.). LC-MS (M-H$^+$): 179.0.

Step 3: 1-(piperazin-1-yl)isoquinoline (2c)

1-Chloroisoquinoline (3 g, 18.3 mmoles, 1 eq.) was dissolved in CH$_3$CN (150 mL) with piperazine (23.7 g, 274.5 mmoles, 15 eq.) and potassium carbonate (3.8 g, 27.5 mmoles, 1.5 eq). The solution was heated to reflux for 48 h then was concentrated, diluted with DCM (250 mL) and washed with sat. NaHCO$_3$ and brine. The organic phase was separated, dried over sodium sulfate and evaporated in vacuum to obtain 1-(piperazin-1-yl)isoquinoline 2c (3.9 g, Y=94%). LC-MS (M-H$^+$): 214.1.

Step 4: N-{3-[4-(isoquinolin-1-yl)piperazin-1-yl]propyl}pyridine-3-carboxamide hydrochloride (2)

Intermediate 2b (150 mg, 0.51 mmoles, 1 eq.) was dissolved in DCM (5 mL). DIPEA (0.078 mL, 0.45 mmoles, 0.9 eq.), acetic acid (one drop) and intermediate 2c (87 mg, 0.41 mmoles, 0.8 eq.) were added subsequently at room temperature. After ten minutes sodium triacetoxyborohydride (141 mg, 0.66 mmoles, 1.3 eq.) was added and the solution was left stirring overnight. The mixture was diluted with DCM, washed with sat. NaHCO$_3$ and sat. NaCl, dried over sodium sulphate, filtered and evaporated in vacuum. The crude material was purified with a NH-Column eluting with ethyl acetate to obtain the desired amine (78 mg, 0.21 mmoles). The product was dissolved in DCM (5 mL) and 1M HCl in Et$_2$O (0.84 mL, 4 eq.) was added dropwise at 0° C. The solution was left stirring for 2 h then concentrated in vacuum and triturated with diethyl ether to obtain title compound N-{3-[4-(isoquinolin-1-yl)piperazin-1-yl]propyl}pyridine-3-carboxamide hydrochloride 2 (79 mg, Y=39%). LC-MS (M-H$^+$): 376.2.

$^1$H NMR (300 MHz, DMSO-d$_6$) δ=11.37 (br. s., 1H), 9.29-9.14 (m, 2H), 8.88 (dd, J=1.5, 5.5 Hz, 1H), 8.60 (td, J=1.8, 8.1 Hz, 1H), 8.21 (d, J=8.4 Hz, 1H), 8.06 (d, J=6.2 Hz, 1H), 8.02 (d, J=7.7 Hz, 1H), 7.93-7.78 (m, 2H), 7.72 (ddd, J=1.4, 7.0, 8.3 Hz, 1H), 7.59 (d, J=6.2 Hz, 1H), 6.71 (br. s., 2H), 4.06 (d, J=13.5 Hz, 2H), 3.88-3.56 (m, 4H), 3.44 (q, J=6.5 Hz, 4H), 3.34-3.20 (m, 2H), 2.09 (quin, J=6.7 Hz, 2H).

Preparation of compound 3: N-{3-[4-(isoquinolin-1-yl)piperazin-1-yl]propyl}benzamide hydrochloride Compound 3 was prepared according to the procedure described for compound 2, using in step 1 benzoyl chloride. LC-MS (M-H$^+$): 375.2.

$^1$H NMR (300 MHz, DMSO-d$_6$) δ=11.68 (br. s., 1H), 8.79 (t, J=5.4 Hz, 1H), 8.25 (d, J=8.6 Hz, 1H), 8.06 (d, J=8.6 Hz, 1H), 8.02 (dd, J=1.0, 6.3 Hz, 1H), 7.98-7.86 (m, 3H), 7.75 (ddd, J=1.1, 7.0, 8.5 Hz, 1H), 7.63 (d, J=6.3 Hz, 1H), 7.58-7.41 (m, 3H), 4.16 (d, J=13.5 Hz, 2H), 3.90 (t, J=12.4 Hz, 2H), 3.66 (d, J=13.1 Hz, 2H), 3.56-3.34 (m, 4H), 3.25 (quin, J=5.0 Hz, 2H), 2.08 (quin, J=7.2 Hz, 2H).

Preparation of compound 4: N-{2-[4-(isoquinolin-1-yl)piperazin-1-yl]ethyl}benzamide hydrochloride Compound 4 was prepared according to the procedure described for compound 2, using in step 1 benzoyl chloride and 2,2-diethoxyethanamine. LC-MS (M-H$^+$): 361.2.

$^1$H NMR (300 MHz, DMSO-d$_6$) δ=8.71 (t, J=5.5 Hz, 1H), 8.15 (d, J=5.7 Hz, 1H), 8.14 (d, J=8.6 Hz, 1H), 7.93 (d, J=7.5 Hz, 1H), 7.91-7.87 (m, 2H), 7.75 (ddd, J=1.5, 7.0, 8.3 Hz, 1H), 7.64 (ddd, J=1.7, 7.0, 8.3 Hz, 1H), 7.61-7.45 (m, 4H), 6.06 (s, 2H), 3.68 (q, J=6.2 Hz, 2H), 3.63-3.19 (m, 10H).

Preparation of Compound 14

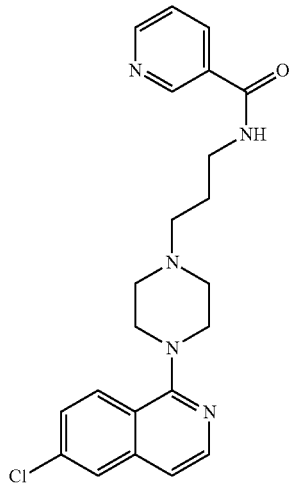 [SMILES: O=C(NCCCN1CCN(c2nccc3cc(Cl)ccc23)CC1)c1cccnc1]

Compound 14 was prepared according to the procedure described for the synthesis of compound 2, using 1,6-dichloroisoquinoline in step 3 (Y=78%). LC-MS (M-H$^+$)=410.2

$^1$H NMR (300 MHz, DMSO-d$_6$) δ=11.36 (br. s., 1H), 9.30 (t, J=5.3 Hz, 1H), 9.25 (d, J=1.7 Hz, 1H), 8.90 (dd, J=1.3, 5.3 Hz, 1H), 8.67 (d, J=7.9 Hz, 1H), 8.19 (d, J=8.9 Hz, 1H), 8.14 (d, J=3.3 Hz, 1H), 8.13 (s, 1H), 7.88 (dd, J=5.4, 8.1 Hz, 1H), 7.67 (dd, J=2.1, 9.1 Hz, 1H), 7.51 (d, J=5.9 Hz, 1H), 3.96 (d, J=13.9 Hz, 2H), 3.76-3.54 (m, 4H), 3.50-3.34 (m, 4H), 3.32-3.19 (m, J=4.6 Hz, 2H), 2.19-1.99 (m, 2H).

Preparation of compound 21: N-{3-[4-(3-methylisoquinolin-1-yl)piperazin-1-yl]propyl}pyridine-3-carboxamide hydrochloride Compound 21 was prepared according to the procedure described for compound 2, using in step 3 1-chloro-3-methylisoquinoline. LC-MS (M-H$^+$): 390.2.

¹H NMR (400 MHz, DMSO-d₆) δ=11.37 (br. s., 1H), 9.30 (t, J=5.4 Hz, 1H), 9.25 (d, J=1.5 Hz, 1H), 8.90 (dd, J=1.4, 5.1 Hz, 1H), 8.65 (d, J=8.0 Hz, 1H), 8.12 (d, J=8.5 Hz, 1H), 7.92-7.83 (m, 2H), 7.78 (t, J=7.5 Hz, 1H), 7.60 (t, J=7.5 Hz, 1H), 7.37 (s, 1H), 7.30-5.98 (m, 3H), 5.76 (s, 1H), 3.98 (d, J=13.3 Hz, 2H), 3.78-3.54 (m, 4H), 3.51-3.34 (m, 4H), 3.27 (td, J=4.6, 9.6 Hz, 2H), 2.54 (s, 3H), 2.19-1.99 (m, 1H)

Preparation of compound 28: 4-({1-[3-(isoquinolin-1-yl)prop-2-yn-1-yl]piperidin-4-yl}amino)-2H-chromen-2-one Compound 28 was prepared as described hereinbelow.

Step 2: tert-butyl 4-[(2-oxo-2H-chromen-4-yl)amino]piperidine-1-carboxylate (28b)

Triethylamine (1 mL, 7.2 mmoles, 1.2 eq.) in acetonitrile (2 mL) was added dropwise to a stirred solution of intermediate 28a (1.76 g, 5.99 mmoles, 1 eq.) and 1-Boc-4-aminopiperidine (1.2 g, 5.99 mmoles, 1 eq.) in dry acetonitrile (20 mL). The mixture was heated at reflux for 2 h then was cooled to room temperature, diluted with DCM (100 mL) and washed with saturated NaHCO₃ (50 mL) and water (50 mL). The organic phase was separated, dried over sodium sulfate and evaporated in vacuum. The crude material was purified by trituration with methanol to obtain

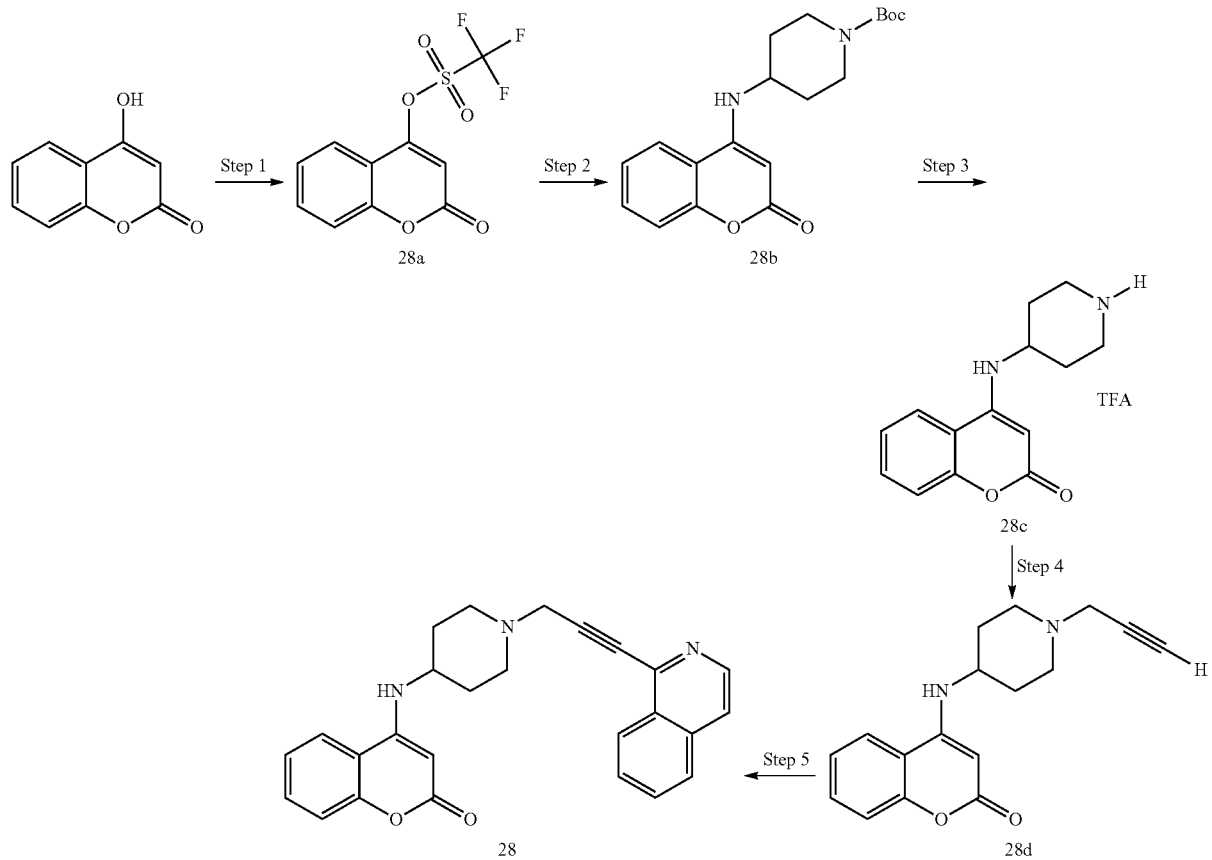

Step 1: 2-oxo-2H-chromen-4-yl trifluoromethanesulfonate (28a)

4-Hydroxycoumarine (1 g, 6.17 mmoles, 1 eq.) was dissolved in DCM (30 mL), triethylamine (1.72 mL, 12.34 mmoles, 2 eq.) was added and the resulting mixture was cooled to −10° C. Trifluoromethanesulfonic anhydride (1.25 mL, 7.4 mmoles, 1.2 eq.) in DCM (5 mL) was added dropwise and the solution was left stirring at −10° C. for 2 h. The resulting reddish brown solution was warmed to room temperature, diluted with cHex/Et₂O 1/1 (50 mL) and filtered through a pad of silica gel using cHex/Et₂O 1/1 as eluent. The solvent was removed in vacuum to obtain 2-oxo-2H-chromen-4-yl trifluoromethanesulfonate 28a (1.76 g, Y=97%). LC-MS (M-H⁺): 295.0.

tert-butyl 4-[(2-oxo-2H-chromen-4-yl)amino]piperidine-1-carboxylate 28b (1.51 g, Y=73%). LC-MS (M-H⁺): 345.2.

Step 3: 4-(piperidin-4-ylamino)-2H-chromen-2-one trifluoroacetic acid salt (28c)

Intermediate 28b (1 g, 2.90 mmoles, 1 eq.) was dissolved in DCM (10 ml) and TFA (3 mL) was added dropwise at 0° C. The solution was left stirring for 2 h then was concentrated in vacuum and washed with toluene (25 ml) and diethyl ether (25 ml) to obtain 4-(piperidin-4-ylamino)-2H-chromen-2-one trifluoroacetic acid salt 28c, which was used without any further purification (1.22 g, Y=quant.). LC-MS (M-H⁺): 245.1.

Step 4: 4-{[1-(prop-2-yn-1-yl)piperidin-4-yl]amino}-2H-chromen-2-one (28d)

To a solution of intermediate 28c (50 mg, 0.14 mmoles, 1 eq.) and potassium carbonate (38.7 mg, 0.28 mmoles, 2 eq.) in DMF (2 mL) 3-bromo-1-propyne (20.8 mg, 0.14 mmoles, 1 eq.) was added at room temperature. The reaction was left stirring overnight then was filtered and the filtrate concentrated. The residue was purified by Si-column eluting with eluting with EtOAc to EtOAc/Methanol 8:2 to give 4-{[1-(prop-2-yn-1-yl)piperidin-4-yl]amino}-2H-chromen-2-one 28d (25.6 mg, Y=64%). LC-MS (M-H$^+$): 283.1.

Step 5: 4-({1-[3-(isoquinolin-1-yl)prop-2-yn-1-yl]piperidin-4-yl}amino)-2H-chromen-2-one (28)

Intermediate 28d (186 mg, 0.66 mmoles, 1 eq.), 1-chloroisoquinoline (120 mg, 0.72 mmoles, 1.1 eq.) and CuI (12 mg, 0.066 mmoles, 0.1 eq.) were dissolved in dry DMF (3.6 ml). DIPEA (0.473 ml, 2.64 mmoles, 4 eq.) was added. The mixture was degassed by alternatively applying vacuum and nitrogen, then bis(triphenylphosphine)palladium(II) dichloride (45 mg, 0.066 mmoles, 0.1 eq.) was added and the mixture was heated at 60° C. After 3 h water (10 mL) was added and the mixture was extracted with ethyl acetate (3×10 mL). The organic phase was washed with brine, dried over Na$_2$SO$_4$, filtered and concentrated in vacuum to give 283 mg of crude material. After purification by Si-column eluting with EtOAc to EtOAc/MeOH 8:2 compound 4-({1-[3-(isoquinolin-1-yl)prop-2-yn-1-yl]piperidin-4-yl}amino)-2H-chromen-2-one 28 (87 mg, Y=32%) was obtained. LC-MS (M-H+): 410.2.

$^1$H NMR (400 MHz, METHANOL-d$_4$) δ=8.42-8.34 (m, 2H), 7.97-7.93 (m, 1H), 7.89 (d, J=7.8 Hz, 1H), 7.79-7.66 (m, 3H), 7.58-7.49 (m, 1H), 7.28-7.20 (m, 2H), 5.30 (s, 1H), 3.78 (s, 2H), 3.60-3.47 (m, 1H), 3.13 (d, J=12.0 Hz, 2H), 2.59 (dt, J=1.8, 11.8 Hz, 2H), 2.11 (d, J=11.3 Hz, 2H), 1.79 (dq, J=3.0, 12.0 Hz, 2H).

Preparation of compound 31: N-{3-[4-(isoquinolin-1-yl)piperazin-1-yl]propyl}furo[3,2-b]pyridine-6-carboxamide hydrochloride Compound 31 was prepared as described hereinbelow.

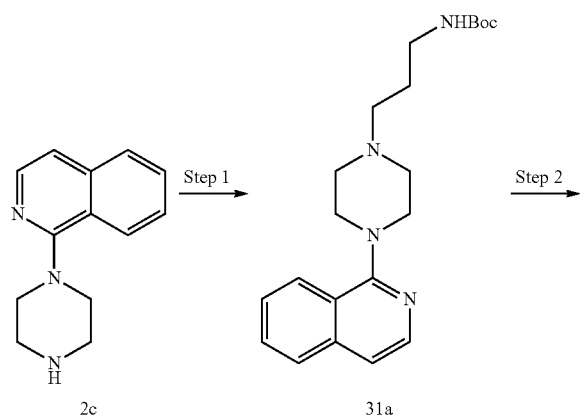

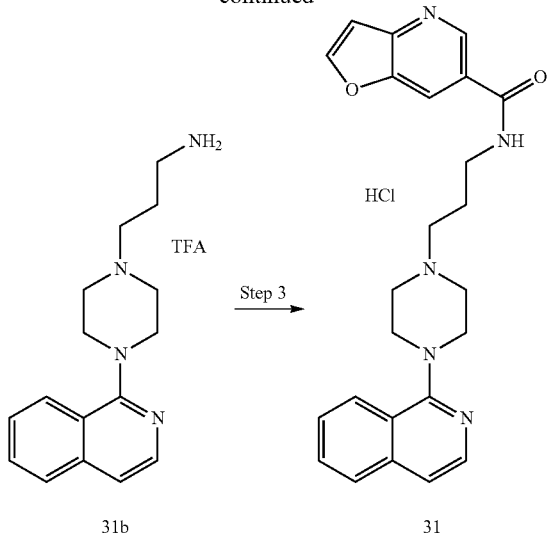

Step 1: tert-butyl {3-[4-(isoquinolin-1-yl)piperazin-1-yl]propyl}carbamate (31a)

A mixture of 1-(piperazin-1-yl)isoquinoline 2c (1.40 g, 6.54 mmoles. 1 eq.), tert-butyl N-(3-bromopropyl)carbamate (1.48 g, 6.22 mmoles, 0.95 eq.), potassium iodide (0.54 g, 3.27 mmoles, 0.50 eq.) and potassium carbonate (1.81 g, 13.1 mmoles, 2 eq.) in DMF (20 mL) was stirred at room temperature for 2 days. The reaction was partitioned between EtOAc (200 mL) and brine (250 mL). The organic phase was separated then was washed with brine (3×200 mL), dried over sodium sulfate and evaporated under reduced pressure. The residue was chromatographed on silica gel (SNAP 100) eluting with a gradient of 20-100% of A in cyclohexane, where A is MeOH/EtOAc (5:95), to give 2.10 g (Y=87%) of tert-butyl {3-[4-(isoquinolin-1-yl)piperazin-1-yl]propyl}carbamate 31a. LC-MS (M-H+)=371.2.

Step 2: 3-[4-(isoquinolin-1-yl)piperazin-1-yl]propan-1-amine TFA salt (31b)

Intermediate 31a (6.35 g, 8.74 mmoles) was dissolved in DCM (25 mL) and TFA (1 mL) was added dropwise at 0° C. The solution was stirred for 2 h then was concentrated in vacuum, washed with toluene and diethyl ether to obtain 3-[4-(isoquinolin-1-yl)piperazin-1-yl]propan-1-amine TFA salt 31b (6.35 g, Y=93%). LC-MS (M-H$^+$)=271.2.

Step 3: N-{3-[4-(isoquinolin-1-yl)piperazin-1-yl]propyl}furo[3,2-b]pyridine-6-carboxamide hydrochloride (31)

Intermediate 31b (250 mg, 0.34 mmoles, 1 eq.) and commercially available furo[3,2-b]pyridine-6-carboxylic acid (56 mg, 0.34 mmoles, 1 eq.) were dissolved in dry DMF (2 mL). TEA (0.25 mL, 1.7 mmoles, 5 eq.) was added, the mixture was cooled to 0° C. and HATU (136 mg, 0.36 mmoles, 1.05 eq.) was added. After stirring at room temperature for 2 h DCM was added, the organic phase was washed with sat. NaHCO$_3$ and brine and evaporated in vacuum. The crude material was purified by Si column eluting with EtOAc to EtOAc/MeOH 8:2 to obtain 100 mg of the desired compound. The product was dissolved in DCM (5 mL) and HCl (1M solution in diethyl ether, 0.70 mL, 4 eq.) was added dropwise at 0° C. The solution was left stirring for 30 min then concentrated in vacuum and triturated with diethyl ether to obtain N-{3-[4-(isoquinolin-1-yl)piperazin-1-yl]propyl}furo[3,2-b]pyridine-6-carboxamide hydrochloride 31 (120 mg, 0.23 mmoles, Y=68%). LC-MS (M-H$^+$)=416.2.

$^1$H NMR (300 MHz, DMSO-d$_6$) δ=11.42 (br. s., 1H), 9.09 (d, J=1.7 Hz, 1H), 9.05 (t, J=5.6 Hz, 1H), 8.57 (s, 1H), 8.51 (d, J=2.4 Hz, 1H), 8.23 (d, J=8.7 Hz, 1H), 8.10-8.00 (m, 2H), 7.91 (t, J=7.5 Hz, 1H), 7.74 (ddd, J=1.0, 7.0, 8.4 Hz, 1H), 7.61 (d, J=6.3 Hz, 1H), 7.25 (dd, J=1.0, 2.4 Hz, 1H), 4.11 (d, J=13.2 Hz, 2H), 3.81 (t, J=12.7 Hz, 2H), 3.67 (d, J=11.5 Hz, 2H), 3.55-3.36 (m, 4H), 3.35-3.20 (m, 2H), 2.11 (quin, J=7.0 Hz, 2H).

Preparation of compound 35: N-{3-[4-(6-methylisoquinolin-1-yl)piperazin-1-yl]propyl}pyridine-3-carboxamide Compound 35 was prepared according to the procedure described for compound 2, using in step 3, 1-chloro-6-methylisoquinoline. LC-MS (M-H$^+$): 390.2.

$^1$H NMR (400 MHz, DMSO-d$_6$) δ=11.44 (br. s., 1H), 9.26 (br. s., 1H), 9.22 (s, 1H), 8.88 (d, J=4.8 Hz, 1H), 8.59 (br. s., 1H), 8.14 (d, J=8.5 Hz, 1H), 7.98 (d, J=6.3 Hz, 1H), 7.84 (s, 2H), 7.59 (d, J=8.5 Hz, 1H), 7.53 (d, J=6.3 Hz, 1H), 4.12 (d, J=14.3 Hz, 2H), 3.82 (t, J=11.7 Hz, 2H), 3.66 (d, J=12.3 Hz, 2H), 3.50-3.35 (m, 4H), 3.32-3.21 (m, 2H), 2.54 (s, 3H), 2.08 (quin, J=7.3 Hz, 2H)

Preparation of compound 36: N-{3-[4-(6-methoxyisoquinolin-1-yl)piperazin-1-yl]propyl}pyridine-3-carboxamide hydrochloride Compound 36 was prepared according to the procedure described for compound 2, using in step 3 1-chloro-6-methoxyisoquinoline. LC-MS (M-H$^+$): 406.2.

$^1$H NMR (400 MHz, DMSO-d$_6$) δ=11.03 (br. s., 1H), 9.13 (d, J=1.3 Hz, 1H), 9.07 (t, J=5.0 Hz, 1H), 8.80 (dd, J=1.0, 5.0 Hz, 1H), 8.40 (d, J=7.5 Hz, 1H), 8.14 (d, J=9.3 Hz, 1H), 7.98 (d, J=6.3 Hz, 1H), 7.72-7.64 (m, 1H), 7.52 (d, J=6.5 Hz, 1H), 7.48 (s, 1H), 7.32 (dd, J=2.3, 9.3 Hz, 1H), 4.39-3.53 (m, 8H), 3.49-3.33 (m, 4H), 3.31-3.19 (m, 2H), 2.16-1.95 (m, 2H)

Preparation of compound 38: N-(2,5-difluorobenzyl)-3-[4-(isoquinolin-1-yl)piperazin-1-yl]propan-1-amine hydrochloride Intermediate 31b (0.21 mmoles, 1 eq.) was dissolved in dry DCE (3 mL) and 2,5-difluorobenzaldehyde (32.8 mg, 0.23 mmoles, 1.1 eq), DIPEA (0.146 mL, 0.84, 4 eq.) and acetic acid (one drop) were added subsequently at room temperature. The mixture was stirred for 4 h at 60° C. Sodium borohydride (12 mg, 0.315 mmoles, 1.5 eq.) was added. The mixture was stirred at room temperature for 12 h then DCM was added and the mixture was washed with sat. NaHCO$_3$. The collected organic phases were evaporated in vacuum and the crude material was purified by Si-column eluting with ethyl acetate to ethyl acetate/MeOH 6:4 to afford the desired compound as free base. The product was dissolved in DCM then HCl (1M solution in diethyl ether, 0.156 mL, 3 eq.) was added dropwise at 0° C. The solution was left stirring for 2 h then was concentrated in vacuum and triturated with diethyl ether to obtain N-(2,5-difluorobenzyl)-3-[4-(isoquinolin-1-yl)piperazin-1-yl]propan-1-amine hydrochloride 38 (26.6 mg, Y=24%). LC-MS (M-H+): 397.2.

$^1$H NMR (400 MHz, DMSO-d$_6$) δ=11.00 (br. s., 1H), 9.47 (br. s., 2H), 8.21-8.08 (m, 2H), 7.95 (d, J=8.0 Hz, 1H), 7.77 (t, J=7.0 Hz, 1H), 7.70-7.59 (m, 2H), 7.51 (d, J=5.8 Hz, 1H), 7.45-7.32 (m, 2H), 5.75 (s, 1H), 4.23 (t, J=5.4 Hz, 2H), 3.90 (d, J=12.8 Hz, 2H), 3.58 (br. s., 4H), 3.43-3.22 (m, 4H), 3.18-3.07 (m, 2H), 2.22 (quin, J=7.4 Hz, 2H)

Preparation of compound 39: 2,5-difluoro-N-{3-[4-(isoquinolin-1-yl)piperazin-1-yl]propyl}benzamide hydrochloride Compound 39 was prepared according to the procedure described for compound 31, using in step 3, 2,5-difluorobenzoic acid. LC-MS (M-H$^+$): 411.2.

$^1$H NMR (400 MHz, DMSO-d$_6$) δ=10.04 (br. s., 1H), 8.63-8.53 (m, 1H), 8.15 (d, J=5.8 Hz, 2H), 7.95 (d, J=8.0 Hz, 1H), 7.76 (t, J=7.0 Hz, 1H), 7.69-7.60 (m, 1H), 7.55-7.45 (m, 2H), 7.44-7.32 (m, 2H), 3.88 (d, J=10.0 Hz, 2H), 3.63 (br. s., 3H), 3.46-3.32 (m, 6H), 3.26 (td, J=5.3, 10.7 Hz, 2H), 2.00 (quin, J=7.2 Hz, 2H)

Preparation of compound 42: N-{3-[4-(isoquinolin-1-yl)piperazin-1-yl]propyl}furo[2,3-c]pyridine-5-carboxamide hydrochloride The compound was prepared according to the procedure described for compound 31, using in step 3 furo[2,3-c]pyridine-5-carboxylic acid. LC-MS (M-H$^+$): 489.2.

$^1$H NMR (400 MHz, DMSO-d$_6$) δ=10.24 (br. s., 1H), 9.07 (t, J=5.9 Hz, 1H), 9.03 (s, 1H), 8.43 (d, J=0.8 Hz, 1H), 8.36 (d, J=2.3 Hz, 1H), 8.15 (d, J=8.3 Hz, 1H), 8.12 (d, J=5.8 Hz, 1H), 7.96 (d, J=8.3 Hz, 1H), 7.79 (t, J=7.4 Hz, 1H), 7.66 (t, J=7.4 Hz, 1H), 7.52 (d, J=5.8 Hz, 1H), 7.23 (d, J=1.5 Hz, 1H), 3.91 (d, J=11.5 Hz, 2H), 3.60 (br. s., 4H), 3.50-3.33 (m, 5H), 3.31-3.16 (m, 2H), 2.16-1.95 (m, 2H)

Preparation of compound 43: N-{3-[4-(1,6-naphthyridin-5-yl)piperazin-1-yl]propyl}pyridine-3-carboxamide hydrochloride Compound 43 was prepared according to the procedure described for compound 2, using in step 3 5-chloro-1,6-naphthyridine. LC-MS (M-H$^+$): 377.2.

$^1$H NMR (400 MHz, DMSO-d$_6$) δ=(CHLOROFORM-d) 9.04 (d, J=2.0 Hz, 1H), 9.00 (dd, J=1.6, 4.1 Hz, 1H), 8.71 (dd, J=1.8, 4.8 Hz, 1H), 8.39-8.33 (m, 2H), 8.22 (br. s., 1H), 8.17 (td, J=1.9, 8.0 Hz, 1H), 7.52 (d, J=5.8 Hz, 1H), 7.43 (dd, J=4.3, 8.5 Hz, 1H), 7.39 (dd, J=4.9, 7.9 Hz, 1H), 3.65 (q, J=5.8 Hz, 2H), 3.56-3.41 (m, 4H), 2.81 (br. s., 4H), 2.73 (t, J=5.8 Hz, 2H), 1.91 (quin, J=6.0 Hz, 2H)

Preparation of compound 45: N-{3-[4-(6-fluoroisoquinolin-1-yl)piperazin-1-yl]propyl}pyridine-3-carboxamide hydrochloride Compound 45 was prepared according to the procedure described for compound 2, using in step 3 1-chloro-6-fluoroisoquinoline. LC-MS (M-H$^+$): 394.2.

$^1$H NMR (300 MHz, DMSO-d$_6$) δ=9.40-9.32 (m, 1H), 9.28 (s, 1H), 8.93 (d, J=5.3 Hz, 1H), 8.72 (d, J=7.6 Hz, 1H), 8.30 (dd, J=5.6, 9.1 Hz, 1H), 8.09 (d, J=6.1 Hz, 1H), 7.99-7.89 (m, 1H), 7.84 (dd, J=2.2, 9.5 Hz, 1H), 7.63-7.52 (m, 2H), 4.02 (d, J=13.4 Hz, 2H), 3.75 (t, J=12.6 Hz, 2H), 3.64 (d, J=12.0 Hz, 2H), 3.43 (ddd, J=5.7, 5.8, 11.8 Hz, 4H), 3.34-3.20 (m, 2H), 2.20-1.97 (m, 2H).

Preparation of Compound 50

Compound 50 was prepared as described herein below.

Step 1—Synthesis of tert-butyl N-{3-[4-(naphthalen-1-yl)piperazin-1-yl]propyl}carbamate

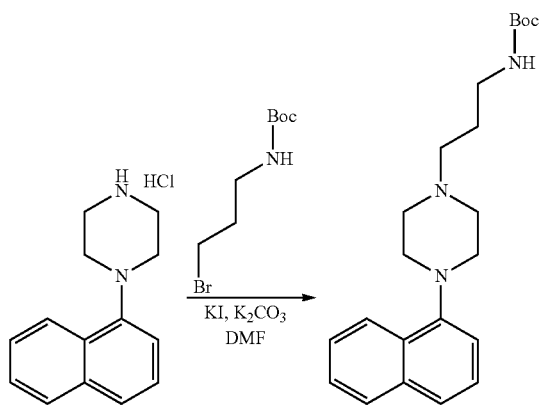

A mixture of commercial 1-(naphthalen-1-yl)piperazine hydrochloride (200 mg, 0.80 mmol), tert-butyl N-(3-bromopropyl)carbamate (182 mg, 0.76 mmol), potassium iodide (66 mg, 016 mmol) and potassium carbonate (221 mg, 1.6 mmol) in DMF (3 mL) was stirred 18 h at room temperature. The reaction mixture was partitioned between EtOAc (50 mL) and brine (50 mL), the organic phase was washed with brine (50 mL), dried over sodium sulfate and evaporated under reduced pressure. The residue was chromatographed on silica gel (SNAP 25) eluting with a gradient of 30-100% EtOAc in cyclohexane to give 263 mg (0.71 mmol, 94% yield) of the title compound. LC-MS (M-H$^+$)=370.4

Step 2—Synthesis of 3-[4-(naphthalen-1-yl)piperazin-1-yl]propan-1-amine

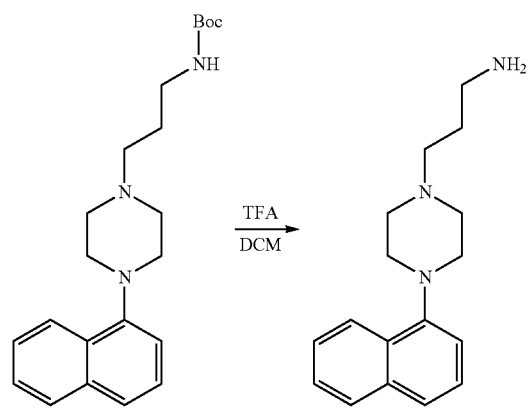 [SMILES: CC(C)(C)OC(=O)NCCCN1CCN(c2cccc3ccccc23)CC1 ; NCCCN1CCN(c2cccc3ccccc23)CC1]

TFA (2 mL) was added to a solution of tert-butyl N-{3-[4-(naphthalen-1-yl)piperazin-1-yl]propyl}carbamate (261 mg, 071 mmol) in dichloromethane (6 mL). The resulting mixture was stirred 1 h at room temperature then the volatiles were evaporated under reduced pressure. The residue was dissolved in dichloromethane (10 mL) and evaporated under reduced pressure twice. The resulting residue was dissolved in MeOH (4 mL) and loaded onto a preconditioned SCX cartridge (5 g) eluting with MeOH and with a 2M solution of ammonia in methanol. The basic fractions were dried under reduced pressure to give 193 mg (0.71 mmol, quant.) of the title compound as a white solid. LC-MS (M-H$^+$)=270.3

Step 3—Synthesis of 4-({3-[4-(naphthalen-1-yl)piperazin-1-yl]propyl}amino)-2H-chromen-2-one hydrochloride (compound 50)

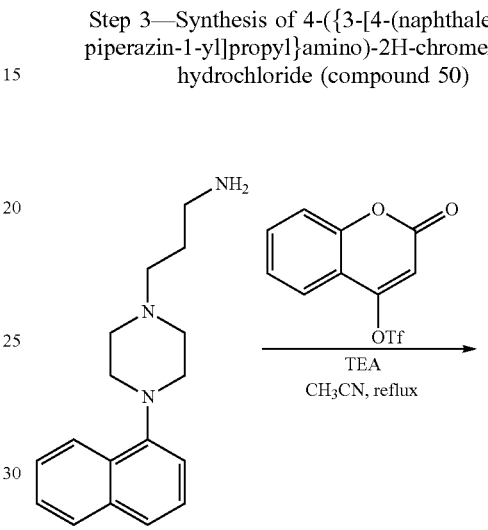

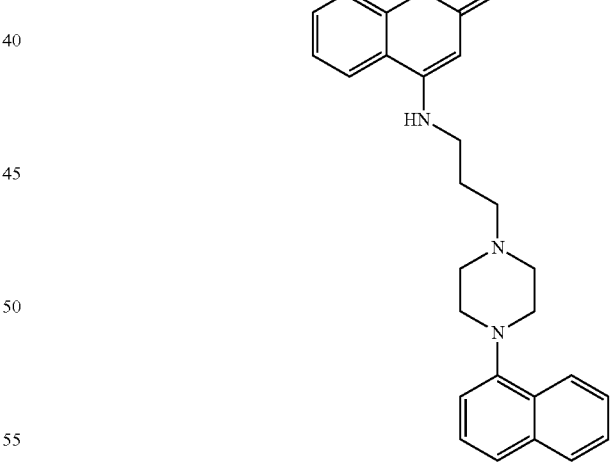

Compound 50 was prepared according to the procedure described for the synthesis of 53 (step 3, Y=21%). LC-MS (M-H+)=414.2

$^1$H NMR (400 MHz, DMSO-d$_6$) δ=10.79 (br. s., 1H), 8.19-8.08 (m, 2H), 7.98-7.87 (m, 2H), 7.67 (d, J=8.0 Hz, 1H), 7.61 (t, J=7.3 Hz, 1H), 7.57-7.50 (m, 2H), 7.46 (t, J=7.9 Hz, 1H), 7.34 (t, J=7.7 Hz, 1H), 7.32 (d, J=8.3 Hz, 1H), 7.18 (d, J=7.3 Hz, 1H), 5.28 (s, 1H), 3.64 (d, J=10.0 Hz, 2H), 3.53-3.19 (m, 10H), 2.16 (quin, J=7.0 Hz, 2H).

39

Preparation of compound 53: 4-[{3-[4-(isoquinolin-1-yl)piperazin-1-yl]propyl}(methyl)amino]-2H-chromen-2-one hydrochloride Compound 53 was prepared as described hereinbelow.

Step 1: tert-butyl {3-[4-(isoquinolin-1-yl)piperazin-1-yl]propyl} methylcarbamate (53a)

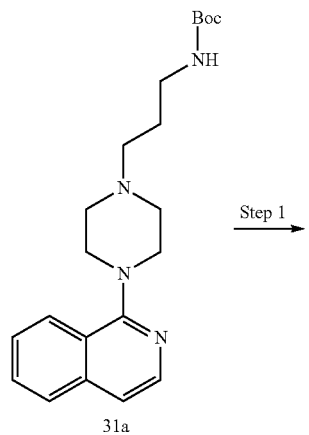

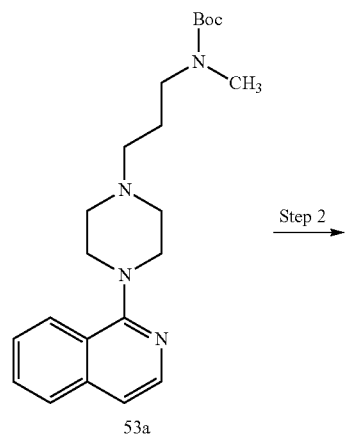

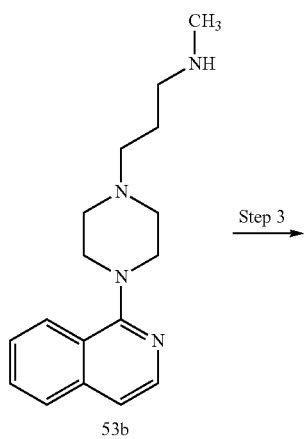

40

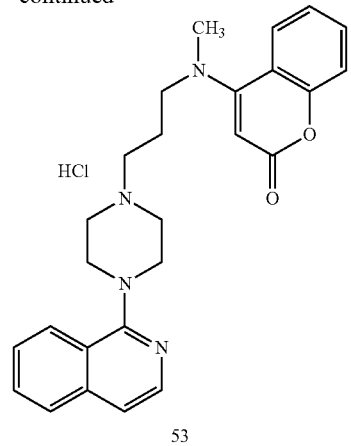

Sodium hydride (24 mg, 60% dispersion in mineral oil, 0.61 mmoles, 1.5 eq.) was added to a stirred solution of intermediate 31a (150 mg, 0.41 mmoles, 1 eq.) in DMF (2 mL) at room temperature. The mixture was stirred for 10 minutes then iodomethane (38 µL, 0.61 mmoles, 1.5 eq.) was added. Stirring was continued for 2 hours then the reaction was quenched with water (50 mL) and extracted with EtOAc (50 mL). The organic phase was washed with brine (50 mL), dried over sodium sulfate and evaporated under reduced pressure. The residue was chromatographed on NH-modified silica gel (2× SNAP 11 in series) eluting with a gradient of 10-50% EtOAc in cyclohexane to give 78 mg of tert-butyl {3-[4-(isoquinolin-1-yl)piperazin-1-yl]propyl}methyl carbamate 53a (Y=50%). LC-MS (M-H+)=385.4.

Step 2: 3-[4-(isoquinolin-1-yl)piperazin-1-yl]-N-methylpropan-1-amine (53b)

TFA (1 mL) was added to a solution of intermediate 53a (78 mg, 0.2 mmoles, 1 eq.) in dichloromethane (3 mL) at room temperature and the resulting mixture was stirred for 60 minutes. The volatiles were evaporated under reduced pressure then the residue was dissolved in MeOH (2 mL) and loaded onto a preconditioned SCX cartridge (1 g). The SCX was eluted with MeOH and then a 2M solution of ammonia in methanol. The basic fractions were evaporated under reduced pressure to give 56 mg of 3-[4-(isoquinolin-1l1)piperazin-1-yl]-N-methylpropan-1-amine 53b (Y=quant.). LC-MS (M-H+)=285.3.

Step 3: 4-[{3-[4-(isoquinolin-1-yl)piperazin-1-yl]propyl}(methyl)amino]-2H-chromen-2-one hydrochloride (53)

A solution of intermediate 53b (56 mg, 0.2 mmoles, 1.1 eq.), triethylamine (37 µL, 0.27 mmoles, 1.5 eq.) and 2-oxo-2H-chromen-4-yl trifluoromethanesulfonate 28a (53 mg, 0.18 mmoles, 1 eq.) in acetonitrile (2 mL) was heated to 70° C. for 1 hour. The reaction mixture was concentrated under reduced pressure and the residue was partitioned between dichloromethane (10 mL) and a brine/sodium bicarbonate mixture (1:1, 10 mL). The mixture was filtered through a hydrophobic frit (Phase Separator) washing with dichloromethane (10 mL). The organic phase was evaporated under reduced pressure and the residue was chromatographed on NH-modified silica gel (2×SNAP 11 in series)

eluting with a gradient of 20-100% EtOAc in cyclohexane to give 79 mg of a colorless sticky gum. The product was dissolved in dichloromethane (3 mL) and treated with 1M HCl solution in diethyl ether (0.46 mL) causing precipitation. The resulting mixture was evaporated under reduced pressure and the residue was triturated with diethyl ether. The solids were dried to give 85 mg of 4-[{3-[4-(isoquinolin-1-yl)piperazin-1-yl]propyl}(methyl)amino]-2H-chromen-2-one hydrochloride 53 as a white solid (Y=95%). LC-MS (M-H+)=429.2.

$^1$H NMR (400 MHz, DMSO-d$_6$) δ=8.19 (d, J=8.3 Hz, 1H), 8.12 (d, J=5.8 Hz, 1H), 8.00 (d, J=8.0 Hz, 1H), 7.88-7.80 (m, 1H), 7.71 (t, J=7.5 Hz, 1H), 7.63 (t, J=7.5 Hz, 1H), 7.57 (d, J=5.8 Hz, 1H), 7.43-7.34 (m, 1H), 5.66 (s, 1H), 3.98 (d, J=13.8 Hz, 2H), 3.73-3.53 (m, 4H), 3.51-3.35 (m, 4H), 3.31-3.14 (m, 2H), 3.08 (s, 3H), 2.24 (br. quin, J=6.5 Hz, 2H).

Preparation of compound 57: 4-({3-[4-(isoquinolin-1-yl)piperazin-1-yl]-3-oxopropyl}amino)-2H-chromen-2-one hydrochloride Compound 57 was prepared as described hereinbelow.

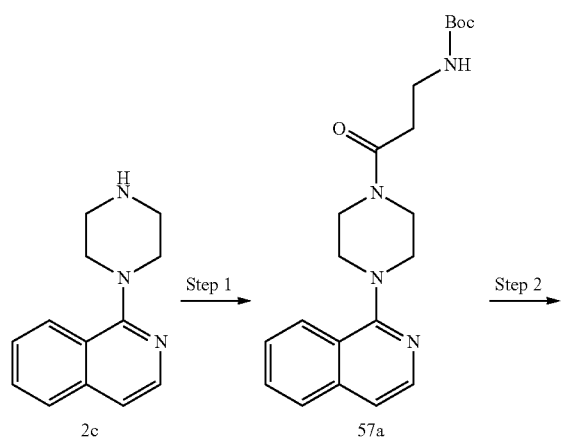

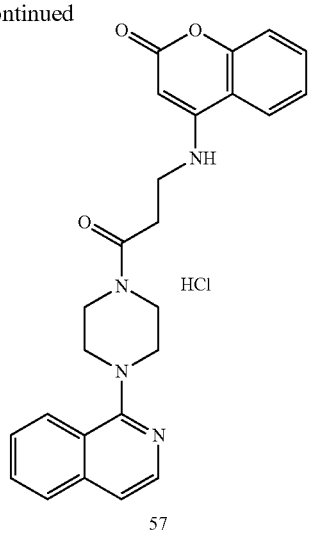

Step 1: tert-butyl {3-[4-(isoquinolin-1-yl)piperazin-1-yl]-3-oxopropyl}carbamate (57a)

1-(piperazin-1-yl)isoquinoline 2c (100 mg, 0.46 mmoles, 1 eq.) was added to a stirred solution of N-(3-dimethylaminopropyl)-N'-ethylcarbodiimide hydrochloride (104 mg, 0.54 mmoles, 1.2 eq.), 1-hydroxybenzotriazole hydrate (72 mg, 0.54 mmoles, 1.2 eq.), 3-{[(tert-butoxy)carbonyl]amino}propanoic acid (86 mg, 0.46 mmoles, 1 eq.) and TEA (190 μl, 0.138 mmoles, 3 eq.) in DCM (5 mL) at room temperature. The resulting mixture was stirred overnight then the organic phase was washed with sodium bicarbonate solution, filtered through a hydrophobic frit (Phase Separator) and evaporated under reduce pressure. The residue was chromatographed on silica gel (SNAP 10) eluting with a gradient of 10-100% EtOAc in cyclohexane to give 148 mg of tert-butyl {3-[4-(isoquinolin-1-yl)piperazin-1-yl]-3-oxopropyl} carbamate 57a (Y=85%). LC-MS (M-H+)=385.4.

Step 2: 3-amino-1-[4-(isoquinolin-1-yl)piperazin-1-yl]propan-1-one (57b)

Intermediate 57b was prepared according to the procedure described for the synthesis of intermediate 53b in the step 2 (Y=92%). LC-MS (M-H+)=285.3.

Step 3: 4-({3-[4-(isoquinolin-1-yl)piperazin-1-yl]-3-oxopropyl}amino)-2H-chromen-2-one hydrochloride (57)

Compound 57 was prepared according to the procedure described for the synthesis of 53 in step 3 (Y=87%). LC-MS (M-H+)=429.3.

$^1$H NMR (400 MHz, DMSO-d$_6$) δ=8.26 (d, J=8.5 Hz, 1H), 8.11-8.00 (m, 2H), 7.98-7.87 (m, 2H), 7.80-7.68 (m, 2H), 7.63-7.56 (m, 1H), 7.54 (d, J=6.5 Hz, 1H), 7.38-7.25 (m, 2H), 5.19 (s, 1H), 4.15 (br. s., 1H), 3.87-3.62 (m, 8H), 3.55 (q, J=6.4 Hz, 2H), 2.82 (t, J=6.8 Hz, 2H)

Preparation of compound 58: 4,4-({3-[4-(isoquinolin-1-yl)piperazin-1-yl]propyl}amino)quinolin-2(1H)-one hydrochloride Compound 58 was prepared as described hereinbelow.

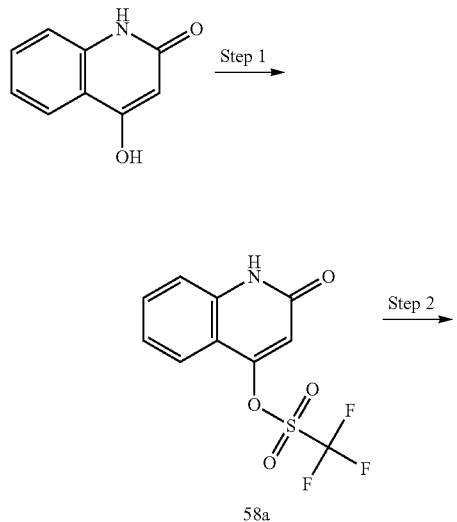

Step 1: 2-oxo-1,2-dihydroquinolin-4-yl trifluoromethanesulfonate (58a)

1,1,1-Trifluoro-N-phenyl-N-(trifluoromethane)sulfonylmethane sulfonamide (1.06 g, 2.98 mmoles, 1.2 eq.) was added to a stirred suspension of 4-hydroxy-1,2-dihydroquinolin-2-one (0.4 g, 2.48 mmoles, 1 eq.) and triethylamine (1.04 mL, 7.44 mmoles, 3 eq.) in DMF (15 mL) at room temperature. The reaction was stirred for 2 hours then was poured into water (100 mL) and extracted with EtOAc (60 mL). The organic phase was washed with brine (50 mL), dried over sodium sulphate and evaporated under reduced pressure. The residue was absorbed onto silica gel (10 g) and placed on top of a silica gel column (SNAP 50) which was eluted with 50-100% EtOAc in cyclohexane to give 537 mg (1.83 mmoles, Y=74%) of 2-oxo-1,2-dihydroquinolin-4-yl trifluoromethanesulfonate 58a as a white solid. LC-MS (M-H+)=294.1.

Step 2: 4,4-({3-[4-(isoquinolin-1-yl)piperazin-1-yl]propyl}amino) quinolin-2(1H)-one hydrochloride (58)

Compound 58 was prepared according to the procedure described for the synthesis of compound 53 (Y=28%), using in step 3 intermediates 58a and 31b. LC-MS (M-H+)=414.4.

$^1$H NMR (400 MHz, DMSO-d$_6$) δ=12.16 (br. s., 1H), 11.06 (br. s., 1H), 8.27 (br. s., 1H), 8.18 (d, J=8.3 Hz, 1H), 8.10 (d, J=5.3 Hz, 1H), 7.99 (d, J=7.8 Hz, 1H), 7.89-7.78 (m, 1H), 7.74-7.61 (m, 2H), 7.60-7.45 (m, 2H), 7.35 (d, J=5.8 Hz, 1H), 5.82 (br. s., 1H), 5.02 (br. s., 2H), 3.97 (d, J=11.5 Hz, 2H), 3.79-3.55 (m, 4H), 3.53-3.23 (m, 6H), 2.19 (br. s., 2H)

Preparation of compound 60: 4-({3-[4-(isoquinolin-1-yl)piperazin-1-yl]propyl}amino)-6-phenyl-2H-pyran-2-one hydrochloride Compound 60 was prepared as described hereinbelow.

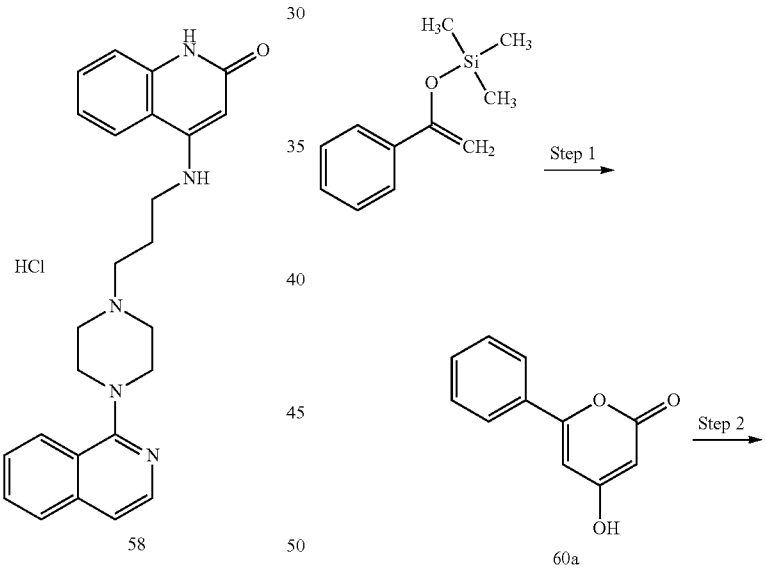

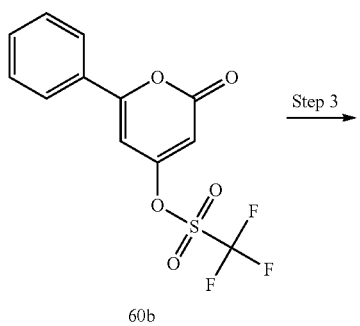

-continued

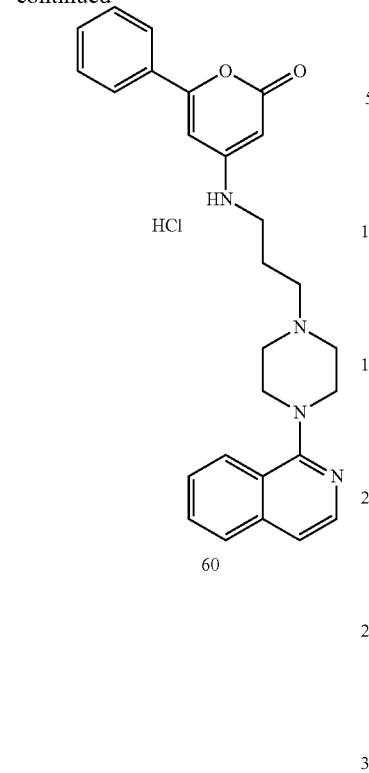

60

Step 1: 4-hydroxy-6-phenyl-2H-pyran-2-one (60a)

Malonyl dichloride (0.25 mL, 2.6 mmoles, 1 eq.) was added dropwise to a stirred solution of trimethyl[(1-phenylethenyl)oxy]silane (1.07 mL, 5.2 mmoles, 2 eq.) in diethyl ether (16 mL) at −78° C. The reaction mixture was stirred overnight allowing the reaction to gradually warm to room temperature. The precipitated solid was collected, washed with diethyl ether (20 mL) and dried under vacuum to give 0.34 g of 4-hydroxy-6-phenyl-2H-pyran-2-one 60a (1.8 mmoles, Y=70%), which was progressed without any further purification. LC-MS (M-H+)=189.1.

Step 2: 2-oxo-6-phenyl-2H-pyran-4-yl trifluoromethanesulfonate (60b)

Intermediate 60b was prepared according to the procedure described for the synthesis of 28a, using in step 1 intermediate 60a (Y=77%). LC-MS (M-H+)=321.1.

Step 3: 4-({3-[4-(isoquinolin-1-yl)piperazin-1-yl]propyl}amino)-6-phenyl-2H-pyran-2-one hydrochloride (60)

Compound 60 was prepared according to the procedure described for the synthesis of 53, using in step 3 intermediates 60b and 31b (Y=37%). LC-MS (M-H+)=441.4.

$^{1}$H NMR (400 MHz, DMSO-d$_{6}$) δ=11.05 (br. s., 1H), 8.19 (d, J=8.3 Hz, 1H), 8.10 (d, J=5.8 Hz, 1H), 7.99 (d, J=7.8 Hz, 1H), 7.83 (t, J=7.2 Hz, 1H), 7.70 (dd, J=6.7, 14.7 Hz, 4H), 7.61-7.46 (m, 4H), 6.60 (br. s., 1H), 5.62 (br. s., 1H), 5.03 (d, J=1.3 Hz, 1H), 3.98 (d, J=11.8 Hz, 2H), 3.64 (d, J=11.5 Hz, 4H), 3.49-3.35 (m, 2H), 3.28 (br. s., 4H), 2.15-2.00 (m, 2H)

Preparation of compound 68: 4-(4-{3-[(2-oxo-2H-chromen-4-yl)amino]propyl}piperazin-1-yl)quinolin-2(1H)-one hydrochloride Compound 68 was prepared as described hereinbelow.

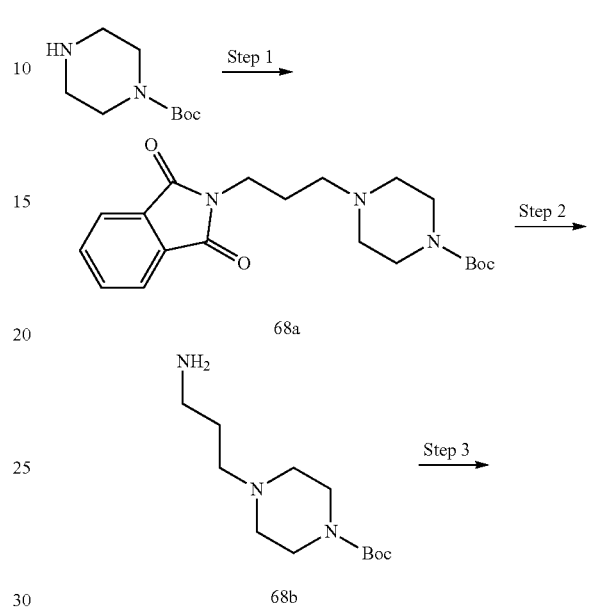

68a

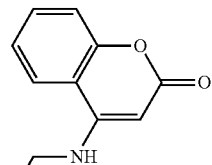

68b

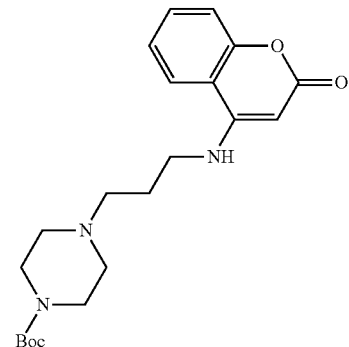

68c

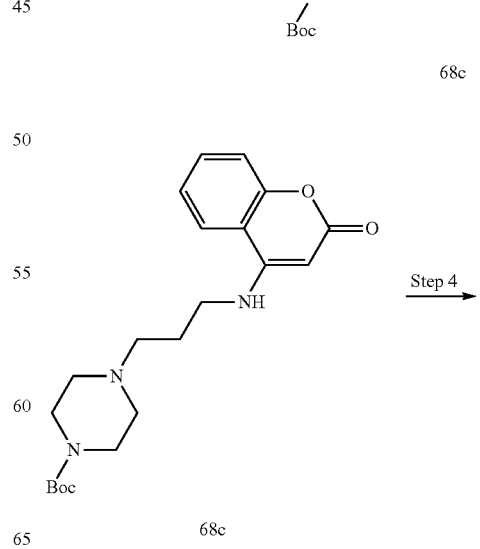

68c

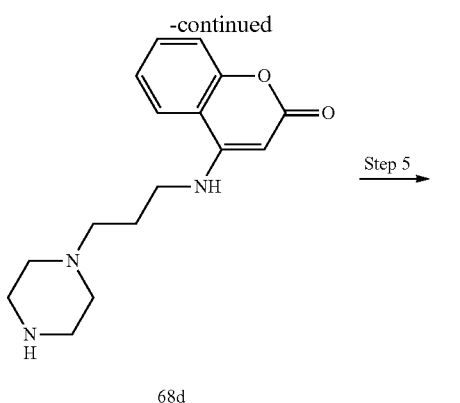

68d

68

Step 1: tert-butyl 4-[3-(1,3-dioxo-1,3-dihydro-2H-isoindol-2-yl)propyl]piperazine-1-carboxylate (68a)

N-(3-Bromopropyl)phthalimide (2.1 g, 7.66 mmoles, 1 eq.), 1-Boc-piperazine (1.5 g, 8 mmoles, 1 eq.), potassium iodide (2.54 g, 15.3 mmoles, 2 eq.) and potassium carbonate (1.76 g, 12.7 mmoles, 1.7 eq.) were dissolved in DMA (15 mL) and stirred at room temperature for 16 h. The solvent was evaporated and the residue was dissolved in DCM. The salts were removed by filtration and the filtrate, after solvent evaporation, was purified by silica column (cHex: EtOAc 8:2 to cHex: EtOAc 1:1). The desired product tert-butyl 4-[3-(1,3-dioxo-1,3-dihydro-2H-isoindol-2-yl)propyl]piperazine-1-carboxylate 68a was obtained as a pale yellow crystalline solid (2.8 g, Y=quant.). LC-MS (M-H+)=374.1.

Step 2: tert-butyl 4-(3-aminopropyl)piperazine-1-carboxylate (68b)

Intermediate 68a (1.9 g, 5.08 mmoles) was dissolved in methylamine (33% in absolute ethanol, 20 mL) and heated at 40° C. for 4 h. The solvent was evaporated, the residue was dissolved in diethyl ether and filtered and the filtrate was evaporated to give tert-butyl 4-(3-aminopropyl)piperazine-1-carboxylate (68b) as a colourless oil (1.1 g, Y=89%). LC-MS (M-H$^+$)=244.3.

Step 3: tert-butyl 4-{3-[(2-oxo-2H-chromen-4-yl)amino]propyl} piperazine-1-carboxylate (68c)

A solution of intermediate 68b (1.1 g, 4.5 mmoles, 1.1 eq.), triethylamine (0.674 mL, 4.8 mmoles, 1.2 eq.) and 2-oxochromen-4-yl trifluoromethanesulfonate 28a (1.2 g, 4.1 mmoles, 1 eq.) in acetonitrile (20 mL) was heated to 70° C. for 1 hour. The reaction mixture was concentrated under reduced pressure and the residue was partitioned between dichloromethane and a brine/sodium bicarbonate mixture (1:1). The mixture was filtered through a hydrophobic frit (Phase Separator) washing with dichloromethane. The organic phase was evaporated under reduced pressure and the residue was chromatographed on silica gel (SNAP50) eluting with a gradient of EtOAc in cyclohexane to give tert-butyl 4-{3-[(2-oxo-2H-chromen-4-yl)amino]propyl}piperazine-1-carboxylate 68c (700 mg, Y=44%). LC-MS (M-H$^+$)=388.3.

Step 4: 4-{[3-(piperazin-1-yl)propyl]amino}chromen-2-one (68d)

TFA (2 mL) was added to a solution of intermediate 68c (700 mg, 1.8 mmoles) in dichloromethane (6 mL) at room temperature and the resulting mixture stirred for 20 minutes. The residue was evaporated under reduced pressure, dissolved in MeOH and loaded onto a preconditioned SCX cartridge. The SCX was eluted with MeOH and then a 2M solution of ammonia in methanol. The basic fractions were evaporated under reduced pressure to give 4-{[3-(piperazin-1-yl)propyl]amino}chromen-2-one 68d (456 mg, Y=88%). LC-MS (M-H$^+$)=288.3.

Step 5: 4-(4-{3-[(2-oxo-2H-chromen-4-yl)amino]propyl}piperazin-1-yl)quinolin-2(1H)-one hydrochloride (68)

A solution of intermediate 68d (70 mg, 024 mmoles, 1.1 eq.), triethylamine (35 uL, 0.26 mmoles, 1.2 eq.) and intermediate 58a (71 mg, 0.22 mmoles, 1 eq.) in DMSO (5 mL) was heated to 80° C. for 1 hour. The mixture was treated with water, the resulting solid was filtered, dissolved in dichloromethane (5 mL) and treated with HCl (1 M solution in diethyl ether, 0.630 mL) causing precipitation. The resulting mixture was evaporated under reduced pressure and the residue was triturated with diethyl ether. The solid was dried to give 113 mg of 4-(4-{3-[(2-oxo-2H-chromen-4-yl)amino]propyl}piperazin-1-yl)quinolin-2(1H)-one hydrochloride 68 as a white solid (Y=quant.). LC-MS (M-H$^+$)=431.3.

$^1$H NMR (400 MHz, DMSO-d$_6$) δ=11.46 (br. s., 1H), 11.20 (br. s., 1H), 8.18 (d, J=7.5 Hz, 1H), 7.98 (br. s., 1H), 7.69 (d, J=8.0 Hz, 1H), 7.60 (t, J=7.3 Hz, 1H), 7.49 (t, J=7.4 Hz, 1H), 7.32 (d, J=7.5 Hz, 3H), 7.16 (t, J=7.3 Hz, 1H), 5.95 (s, 1H), 5.26 (s, 1H), 3.78-3.19 (m, 13H), 2.15 (br. s., 2H)

Preparation of compound 70: 4-{3-[4-(isoquinolin-1-yl)piperazin-1-yl]propoxy}-2H-chromen-2-one hydrochloride Compound 70 was prepared as described hereinbelow.

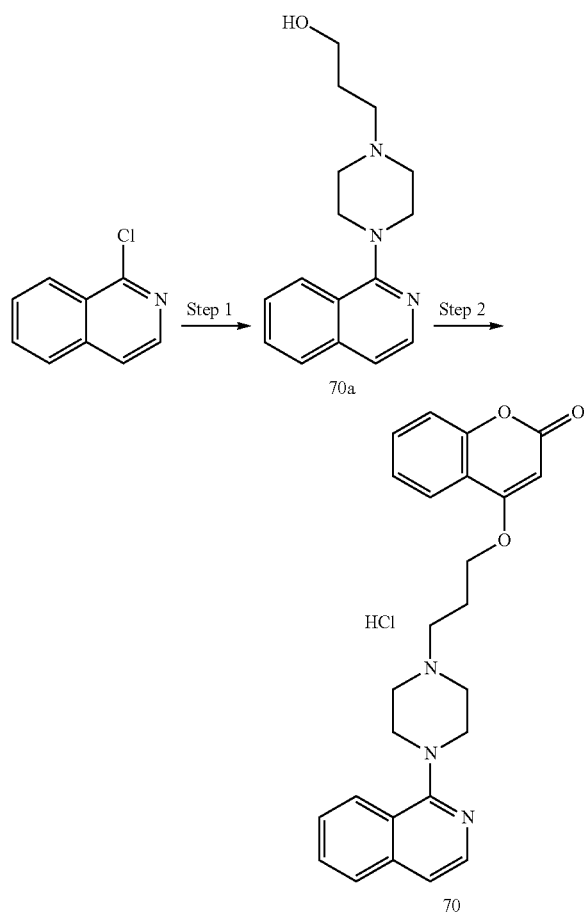

Step 1: 3-[4-(isoquinolin-1-yl)piperazin-1-yl]propan-1-ol (70a)

A mixture of potassium carbonate (634 mg, 4.6 mmoles, 1.5 eq.), 1-chloroisoquinoline (500 mg, 3.1 mmoles, 1 eq.) and 3-(piperazin-1-yl)propan-1-ol (881 mg, 6.1 mmoles, 2 eq.) in DMSO (4 mL) was heated to 120° C. under microwave irradiation for 5 hours. The reaction was allowed to cool to room temperature. The solid was filtered, washed with water then dried under reduced pressure to give 690 mg of 3-[4-(isoquinolin-1-yl)piperazin-1-yl]propan-1-ol 70a (Y=81%). LC-MS (M-H$^+$)=272.2.

Step 2: 4-{3-[4-(isoquinolin-1-yl)piperazin-1-yl]propoxy}-2H-chromen-2-one hydrochloride (70)

Methanesulfonyl chloride (57 μL, 0.74 mmoles, 2 eq.) was added to a stirred solution of intermediate 70a (100 mg, 0.37 mmoles, 1 eq.) and TEA (206 μL, 1.48 mmoles, 4 eq.) in dichloromethane (10 mL) at 0° C. The reaction was stirred for 30 minutes then was left to warm to room temperature. The reaction mixture was washed with saturated aqueous NaHCO$_3$ solution and water. The organic phase was dried over Na$_2$SO$_4$, filtered and concentrated under reduced pressure. The intermediate was used without any further purification for the following reaction.

Sodium hydride (60% dispersion in mineral oil, 15 mg, 0.37 mmoles, 1 eq.) was added to a stirred solution of 4-hydroxy-2H-chromen-2-one (60 mg, 0.37 mmoles, 1 eq.) in acetonitrile (4 mL). The suspension was stirred at room temperature for 30 minutes then was added to a solution of the previously obtained intermediate in acetonitrile (4 mL). K$_2$CO$_3$ (76 mg, 0.55 mmoles, 1.5 eq.) was added and the mixture was heated to 80° C. for 2 h. The volatiles were removed under reduced pressure, the residue was dissolved in dichloromethane and washed with water and brine. The organic phase was dried over Na$_2$SO$_4$, filtered and concentrated under reduced pressure. The residue was chromatographed on silica gel eluting with a gradient of mixture A in dichloromethane, where A is MeOH/NH$_4$OH 95/5, to give 72 mg of a white foam. The product was dissolved in dichloromethane (4 mL) and the minimum amount of MeOH then was treated with HCl (1 M solution in diethyl ether, 0.44 mL) causing precipitation. The solvents were evaporated under reduced pressure and the residue was triturated with diethyl ether. The resulting solid was dried to give 92 mg of 4-{3-[4-(isoquinolin-1-yl)piperazin-1-yl]propoxy}-2H-chromen-2-one hydrochloride 70 (Y=51%). LC-MS (M-H$^+$)=416.3.

$^1$H NMR (400 MHz, DMSO-d$_6$) δ=11.41 (br. s., 1H), 8.20 (d, J=8.5 Hz, 1H), 8.10 (d, J=6.0 Hz, 1H), 8.00 (d, J=8.3 Hz, 1H), 7.95 (dd, J=1.4, 7.9 Hz, 1H), 7.85 (t, J=7.4 Hz, 1H), 7.74-7.66 (m, 2H), 7.57 (d, J=6.0 Hz, 1H), 7.45-7.37 (m, 2H), 5.95 (s, 1H), 5.36 (br. s., 1H), 4.38 (t, J=5.6 Hz, 2H), 4.01 (d, J=13.1 Hz, 2H), 3.79-3.59 (m, 4H), 3.55-3.36 (m, 4H), 2.45-2.35 (m, 2H)

Preparation of compound 71: 4-(isoquinolin-1-yl)-1-{3-[(2-oxo-2H-chromen-4-yl)amino]propyl}piperazin-2-one hydrochloride Compound 71 was prepared as described hereinbelow.

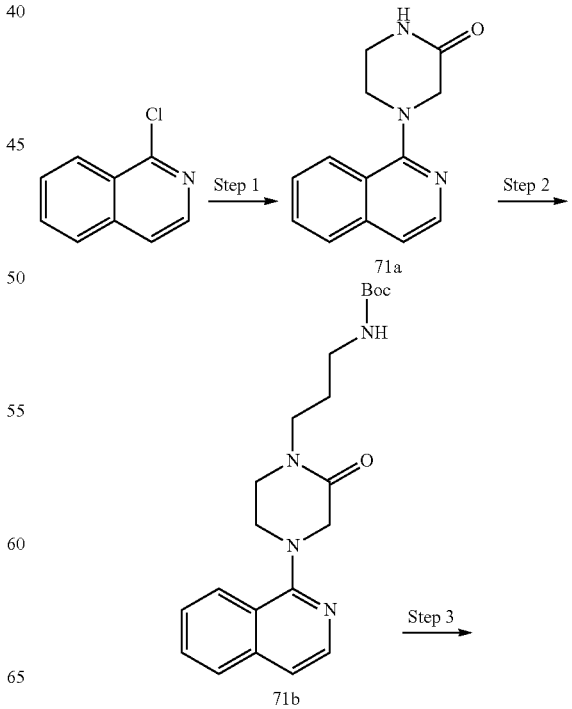

-continued

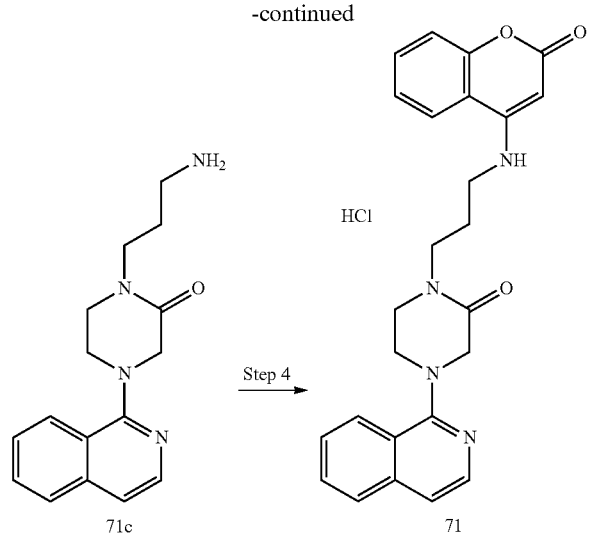

Step 1: 4-(isoquinolin-1-yl)piperazin-2-one (71a)

Intermediate 71a was prepared according to the procedure described in the step 1 of the synthesis of compound 70, using piperazin-2-one (Y=77%). LC-MS (M-H$^+$)=228.1.

Step 2: tert-butyl {3-[4-(isoquinolin-1-yl)-2-oxopiperazin-1-yl] propyl}carbamate (71b)

NaH (60% dispersion in mineral oil, 81 mg, 2 mmoles, 1.1 eq.) and tert-butyl N-(3-bromopropyl)carbamate (330 mg, 1.4 mmoles, 0.75 eq.) were added to a stirred solution of intermediate 71a (420 mg, 1.8 mmoles, 1 eq.) in anhydrous DMF (6 mL). The mixture was stirred for 4 hours then was quenched with water and extracted with ethyl acetate. The organic phase was dried over sodium sulphate and chromatographed on silica eluting with a gradient of 50-100% EtOAc in petroleum ether to give 273 mg of tert-butyl {3-[4-(isoquinolin-1-yl)-2-oxopiperazin-1-yl] propyl}carbamate 71b (Y=51%). LC-MS (M-H+)=385.2.

Step 3: 1-(3-aminopropyl)-4-(isoquinolin-1-yl)piperazin-2-one (71c)

Intermediate 71c was prepared according to the procedure described in step 2 of the synthesis of compound 53 (Y=quant.). LC-MS (M-H$^+$)=285.3.

Step 4: 4-(isoquinolin-1-yl)-1-{3-[(2-oxo-2H-chromen-4-yl)amino]propyl}piperazin-2-one hydrochloride (71)

Compound 71 was prepared according to the procedure described in step 3 of the synthesis of compound 53 (Y=80%). LC-MS (M-H$^+$)=429.3.

$^1$H NMR (400 MHz, DMSO-d$_6$) δ=8.23 (d, J=8.0 Hz, 1H), 8.05 (d, J=8.0 Hz, 1H), 8.02-7.93 (m, 2H), 7.87 (t, J=6.9 Hz, 1H), 7.76-7.63 (m, 2H), 7.61-7.53 (m, 1H), 7.50 (d, J=6.3 Hz, 1H), 7.35-7.23 (m, 2H), 5.19 (s, 1H), 5.04-4.38 (m, 1H), 4.24 (br. s., 2H), 3.92 (br. s., 2H), 3.60 (br. s., 2H), 3.51 (t, J=7.0 Hz, 2H), 3.30 (q, J=7.0 Hz, 2H), 1.93 (quin, J=7.0 Hz, 2H)

Preparation of compound 74: 4-({3-[4-(isoquinolin-1-yl)piperazin-1-yl]cyclohexyl}amino)-2H-chromen-2-one hydrochloride Compound 74 was prepared as described hereinbelow.

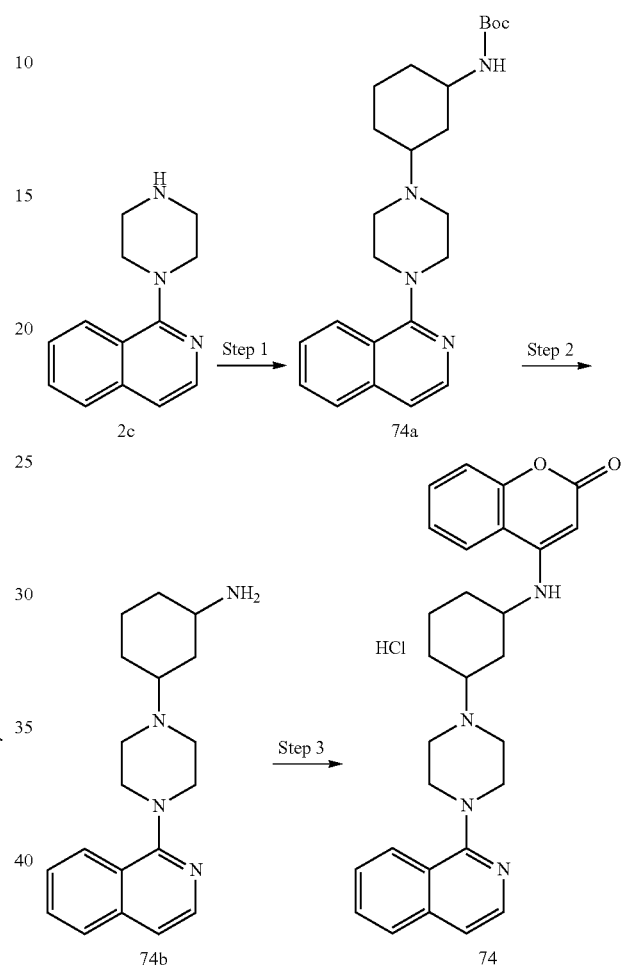

Step 1: tert-butyl {3-[4-(isoquinolin-1-yl)piperazin-1-yl]cyclohexyl} carbamate (74a)

Sodium triacetoxyborohydride (591 mg, 2.8 mmoles, 3 eq.) was added to a stirred solution of 1-(piperazin-1-yl) isoquinoline 2c (200 mg, 0.93 mmoles, 1 eq.) and tert-butyl N-(3-oxocyclohexyl)carbamate (200 mg, 0.93 mmoles, 1 eq.) in dichloromethane (5 mL). The reaction was stirred at room temperature for 2 hours then was diluted with DCM and quenched with water. The mixture was filtered through a hydrophobic frit (Phase Separator). The organic phase was washed with a mixture of brine and sodium bicarbonate solution (1:1) and filtered through a hydrophobic frit (Phase Separator). The organic phase was evaporated under reduced pressure. The residue was chromatographed on silica gel (SNAP 10) eluting with a gradient of EtOAc in cyclohexane to give 245 mg of tert-butyl {3-[4-(isoquinolin-1-yl)piperazin-1-yl]cyclohexyl}carbamate 74a (Y=63%). LC-MS (M-H+)=411.4.

Step 2: 3-[4-(isoquinolin-1-yl)piperazin-1-yl]cyclohexanamine (74b)

Intermediate 74b was prepared according to the procedure described in step 2 of the synthesis of compound 53 (Y=quant.). LC-MS (M-H⁺)=311.3.

Step 3: 4-({3-[4-(isoquinolin-1-yl)piperazin-1-yl]cyclohexyl}amino)-2H-chromen-2-one hydrochloride (74)

Compound 74 was prepared according to the procedure described in step 3 of the synthesis of compound 53 (Y=87%). LC-MS (M-H+)=455.4.

$^1$H NMR (500 MHz, DMSO-$d_6$) δ ppm 1.60-1.76 (m, 2H), 1.76-1.89 (m, 3H), 1.92-2.01 (m, 1H), 2.13-2.22 (m, 1H), 2.42 (d, J=12.72 Hz, 1H), 3.36-4.06 (m, 8H), 3.76-3.84 (m, 1H), 4.24 (br. s., 1H), 5.31 (s, 1H), 6.97 (d, J=6.36 Hz, 1H), 7.28-7.38 (m, 2H), 7.55 (d, J=5.90 Hz, 1H), 7.58-7.64 (m, 1H), 7.69 (t, J=7.58 Hz, 1H), 7.83 (t, J=7.60 Hz, 1H), 7.99 (d, J=7.60 Hz, 1H), 8.08 (d, J=5.87 Hz, 1H), 8.21 (d, J=7.60 Hz, 1H), 8.31 (d, J=7.34 Hz, 1H), 10.88 (br. s., 1H)

Preparation of compound 75: N-{2-[4-(isoquinolin-1-yl)piperazin-1-yl]ethyl}-2-oxo-2H-chromene-4-carboxamide hydrochloride Compound 75 was prepared as described hereinbelow.

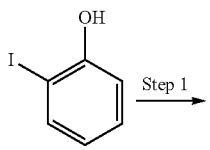

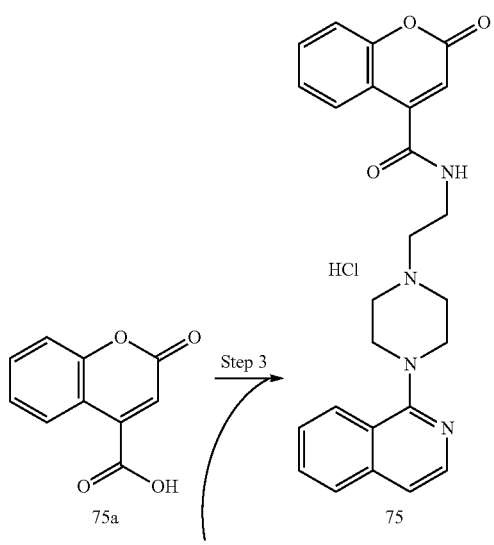

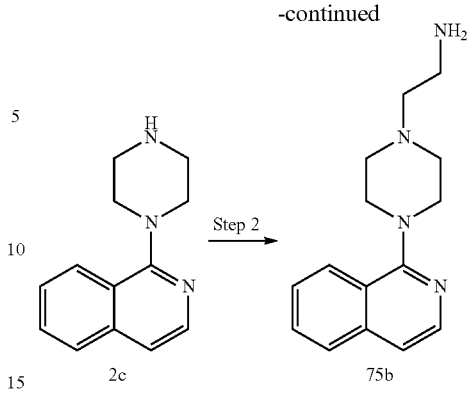

Step 1: 2-oxo-2H-chromene-4-carboxylic acid (75a)

Palladium dichloride (80 mg, 0.45 mmoles, 0.1 eq.) was added to a stirred mixture of 2-iodophenol (1 g, 4.5 mmoles, 1 eq.), dimethyl maleate (1.71 mL, 13.6 mmoles, 3 eq.) and triethylamine (1.90 mL, 13.6 mmoles, 3 eq.) in water (40 mL). The reaction mixture was heated to 85° C. for 24 hours. The reaction mixture was acidified with 1M HCl solution and extracted repeatedly with dichloromethane. The combined organic phases were filtered through a hydrophobic frit (Phase Separator) and evaporated under reduced pressure. The residue was chromatographed on RP-18 (SNAP 60) eluting with a gradient of 2-100% MeCN in water. The MeCN was removed under reduced pressure then the aqueous phase was basified with 1 M NaOH solution and washed with diethyl ether (2×50 mL). The aqueous phase was acidified with 1M HCl solution and extracted repeatedly with dichloromethane. The combined organic phases were filtered through a hydrophobic frit (Phase Separator) and evaporated under reduced pressure to give 228 mg of 2-oxo-2H-chromene-4-carboxylic acid 75a as a pale yellow solid (Y=26%). LC-MS (M-H+)=191.0.

Step 2: 2-[4-(isoquinolin-1-yl)piperazin-1-yl]ethanamine (75b)

Intermediate 75b was prepared as described in step 2 of the synthesis of compound 68 using N-(2-bromoethyl)phthalimide (Y=47%). LC-MS (M-H⁺)=257.2.

Step 3: N-{2-[4-(isoquinolin-1-yl)piperazin-1-yl]ethyl}-2-oxo-2H-chromene-4-carboxamide hydrochloride (75)

Compound 75 (59 mg, Y=35%) was prepared following the conditions described in step 1 of the synthesis of compound 57. LC-MS (M-H⁺)=429.3.

$^1$H NMR (400 MHz, DMSO-$d_6$) δ=11.25 (br. s., 1H), 9.33 (br. s., 1H), 8.20 (d, J=8.3 Hz, 1H), 8.11 (d, J=5.8 Hz, 1H), 8.00 (d, J=8.0 Hz, 1H), 7.90-7.79 (m, 2H), 7.69 (q, J=8.1 Hz, 2H), 7.56 (d, J=5.8 Hz, 1H), 7.47 (d, J=8.3 Hz, 1H), 7.39 (t, J=7.5 Hz, 1H), 6.86 (s, 1H), 4.61-3.04 (m, 13H)

55

Preparation of compound 81: N-{2-[4-(isoquinolin-1-yl)piperazin-1-yl]ethyl}-2-oxo-2H-chromene-4-carboxamide hydrochloride Compound 81 was prepared as described hereinbelow.

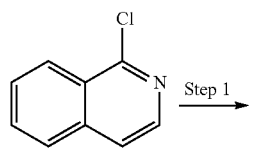

Step 1

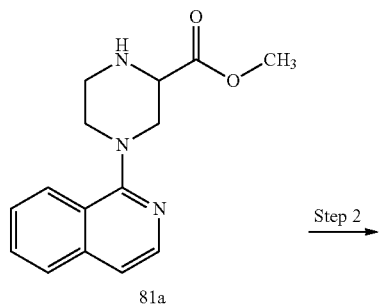

81a

Step 2

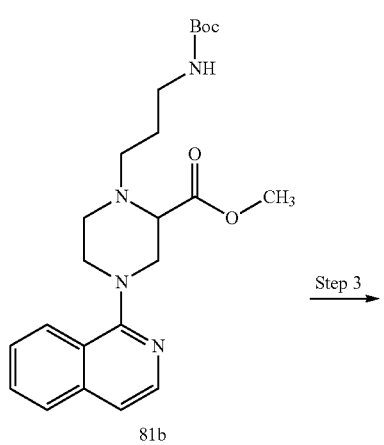

81b

Step 3

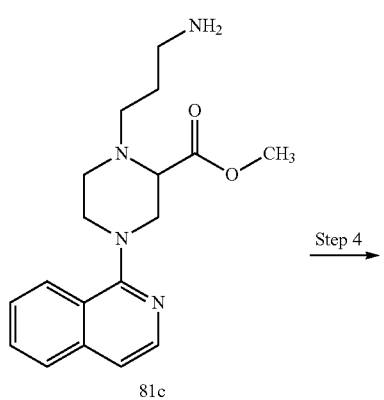

81c

Step 4

56

-continued

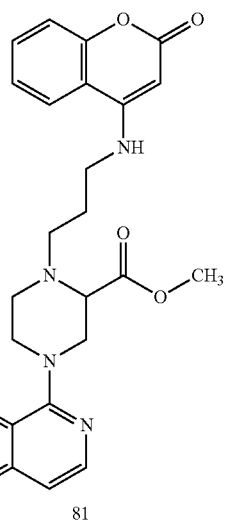

81

Compound 81 was prepared as described for compound 71 starting from methyl piperazine-2-carboxylate. LC-MS (M-H⁺)=473.3.

$^1$H NMR (400 MHz, DMSO-$d_6$) δ=8.14 (d, J=5.8 Hz, 1H), 8.08 (d, J=6.8 Hz, 2H), 7.85-7.75 (m, 2H), 7.71-7.64 (m, 1H), 7.63-7.57 (m, 1H), 7.54 (d, J=5.8 Hz, 1H), 7.38-7.28 (m, 2H), 5.27 (s, 1H), 4.64 (br. s., 7H), 4.12-3.56 (m, 6H), 3.38 (d, J=6.8 Hz, 4H), 2.24-1.92 (m, 2H)

Preparation of compound 82: 4-(isoquinolin-1-yl)-1-{3-[(2-oxo-2H-chromen-4-yl)amino]propyl}piperazine-2-carboxylic acid hydrochloride

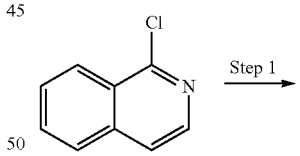

Step 1

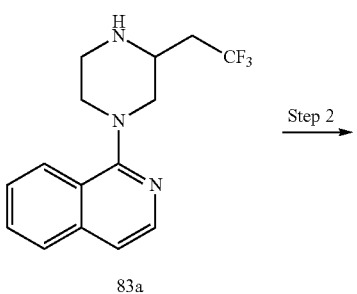

83a

Step 2

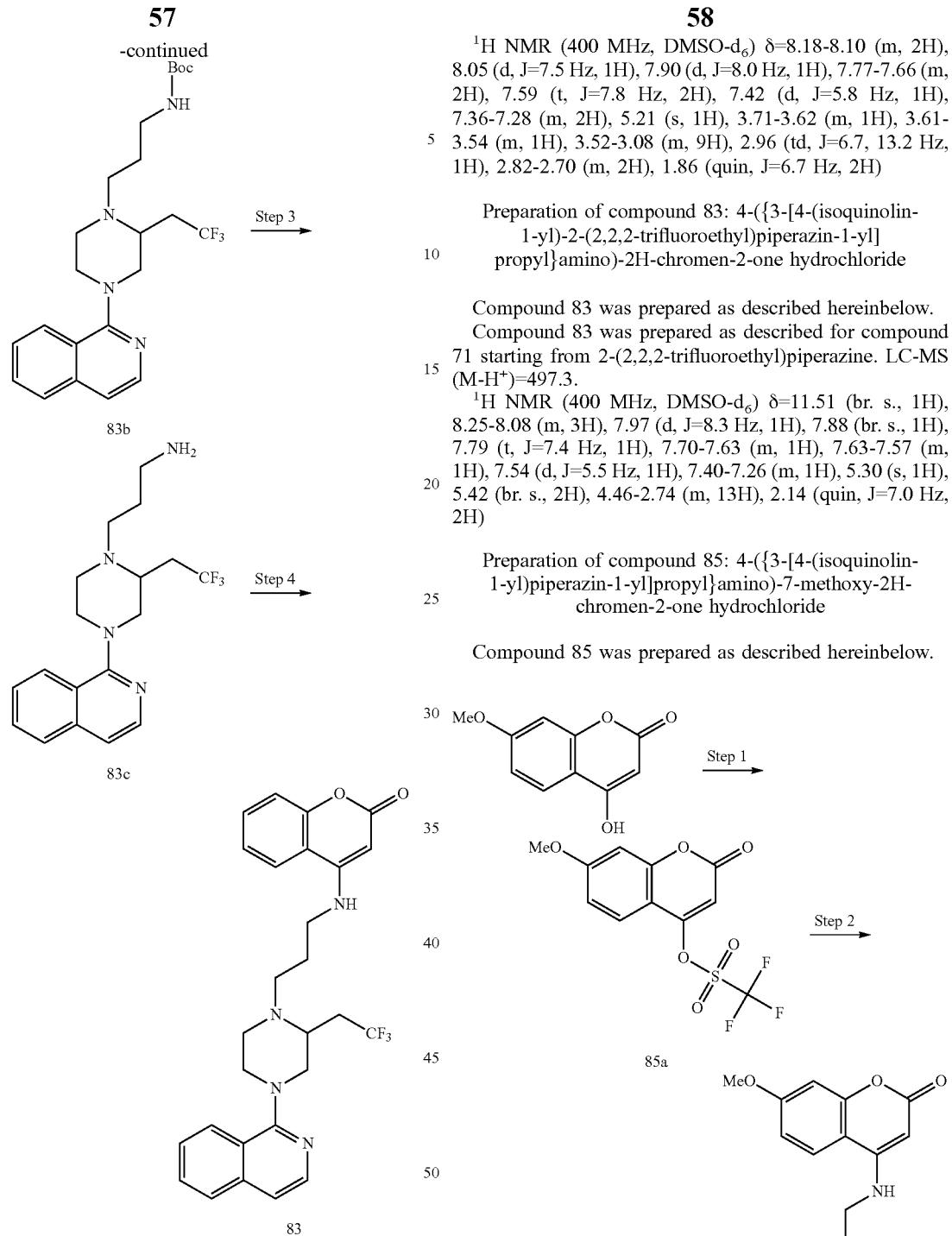

To a solution of methyl 4-(isoquinolin-1-yl)-1-{3-[(2-oxo-2H-chromen-4-yl)amino]propyl}piperazine-2-carboxylate hydrochloride 81 (40 mg, 0.085 mmoles, 1 eq.) in THF/water 9:1 (1 mL) LiOH (4 mg, 0.093 mmoles, 1.1 eq.) was added. The mixture was stirred at 60° C. for 5 hours then was concentrated under reduced pressure. The residue was dissolved in water and 1 M HCl was added (6 eq.). The solvent was evaporated and the crude product was purified by C18 reversed chromatography (acetonitrile/water from 5:95 to 100:0) to obtain 4-(isoquinolin-1-yl)-1-{3-[(2-oxo-2H-chromen-4-yl)amino]propyl}piperazine-2-carboxylic acid hydrochloride 82 (38 mg, Y=84%). LC-MS (M-H+)=459.3.

$^1$H NMR (400 MHz, DMSO-d$_6$) δ=8.18-8.10 (m, 2H), 8.05 (d, J=7.5 Hz, 1H), 7.90 (d, J=8.0 Hz, 1H), 7.77-7.66 (m, 2H), 7.59 (t, J=7.8 Hz, 2H), 7.42 (d, J=5.8 Hz, 1H), 7.36-7.28 (m, 2H), 5.21 (s, 1H), 3.71-3.62 (m, 1H), 3.61-3.54 (m, 1H), 3.52-3.08 (m, 9H), 2.96 (td, J=6.7, 13.2 Hz, 1H), 2.82-2.70 (m, 2H), 1.86 (quin, J=6.7 Hz, 2H)

Preparation of compound 83: 4-({3-[4-(isoquinolin-1-yl)-2-(2,2,2-trifluoroethyl)piperazin-1-yl]propyl}amino)-2H-chromen-2-one hydrochloride Compound 83 was prepared as described hereinbelow.
Compound 83 was prepared as described for compound 71 starting from 2-(2,2,2-trifluoroethyl)piperazine. LC-MS (M-H$^+$)=497.3.

$^1$H NMR (400 MHz, DMSO-d$_6$) δ=11.51 (br. s., 1H), 8.25-8.08 (m, 3H), 7.97 (d, J=8.3 Hz, 1H), 7.88 (br. s., 1H), 7.79 (t, J=7.4 Hz, 1H), 7.70-7.63 (m, 1H), 7.63-7.57 (m, 1H), 7.54 (d, J=5.5 Hz, 1H), 7.40-7.26 (m, 1H), 5.30 (s, 1H), 5.42 (br. s., 2H), 4.46-2.74 (m, 13H), 2.14 (quin, J=7.0 Hz, 2H)

Preparation of compound 85: 4-({3-[4-(isoquinolin-1-yl)piperazin-1-yl]propyl}amino)-7-methoxy-2H-chromen-2-one hydrochloride Compound 85 was prepared as described hereinbelow.

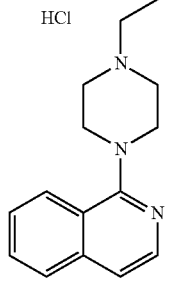

Step 1: 7-methoxy-2-oxo-2H-chromen-4-yl trifluoromethanesulfonate (85a)

Intermediate 85a was prepared as described in step 1 of the synthesis of compound 28, starting from 4-hydroxy-7-methoxy-2H-chromen-2-one (Y=quant.). LC-MS (M-H$^+$)=325.1.

Step 2: 4-({3-[4-(isoquinolin-1-yl)piperazin-1-yl]propyl}amino)-7-methoxy-2H-chromen-2-one hydrochloride (85)

Compound 85 was prepared as described in step 4 of the synthesis of compound 71, using intermediates 85a and 31b (Y=22%). LC-MS (M-H$^+$)=445.4.

$^1$H NMR (400 MHz, DMSO-d$_6$) δ=11.07 (br. s., 1H), 8.18 (d, J=8.3 Hz, 1H), 8.09 (d, J=6.0 Hz, 1H), 8.06 (d, J=8.8 Hz, 1H), 7.99 (d, J=8.0 Hz, 1H), 7.83 (t, J=7.2 Hz, 2H), 7.69 (t, J=7.5 Hz, 1H), 7.55 (d, J=6.0 Hz, 1H), 6.93 (dd, J=2.3, 8.8 Hz, 1H), 6.88 (d, J=2.5 Hz, 1H), 5.14 (s, 1H), 4.10 (br. s., 1H), 3.97 (d, J=12.5 Hz, 2H), 3.89-3.77 (m, 3H), 3.71-3.52 (m, 4H), 3.39 (d, J=5.8 Hz, 4H), 3.29 (br. s., 2H), 2.14 (quin, J=7.0 Hz, 2H)

Preparation of compound 87: 3-({3-[4-(isoquinolin-1-yl)piperazin-1-yl]propyl}amino)-2H-chromen-2-one hydrochloride

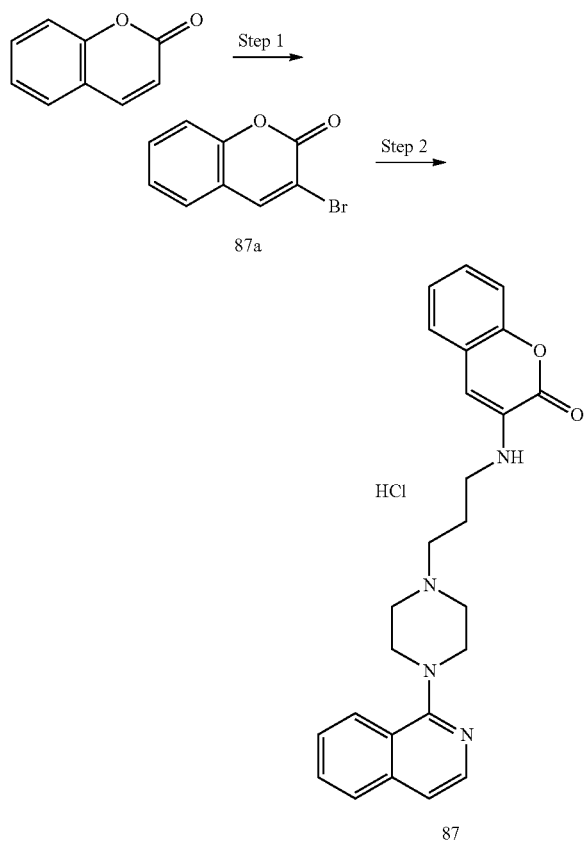

87

Compound 87 was prepared as described hereinbelow.

Step 1: 3-bromo-2H-chromen-2-one (87a)

Bromine (0.35 mL, 6.84 mmoles, 1 eq.) was added dropwise to a stirred solution of coumarin (1 g, 6.84 mmoles, 1 eq.) in chloroform (10 mL) at 0° C. The reaction mixture was allowed to gradually warm to room temperature overnight. Triethylamine (2 mL) was added and the reaction mixture was washed with water (2×10 mL). The organic phase was dried over Na$_2$SO$_4$ and evaporated under reduced pressure. The residue was chromatographed on silica gel (SNAP 50) eluting with 5% EtOAc in petroleum ether to give 504 mg of 3-bromo-2H-chromen-2-one 87a as a white solid (Y=33%). LC-MS (M-H+)=225.0.

Step 2: 3-({3-[4-(isoquinolin-1-yl)piperazin-1-yl]propyl}amino)-2H-chromen-2-one hydrochloride (87)

A mixture of intermediates 31b (50 mg, 0.185 mmoles, 1 eq.) and 87a (50 mg, 0.222 mmoles, 1.2 eq.), Pd(OAc)$_2$ (5 mg, 0.019 mmoles, 0.1 eq.), Xantphos (11 mg, 0.019 mmoles, 0.1 eq.) and Cs$_2$CO$_3$ (90 mg, 0.28 mmoles, 1.5 eq.) in 1,4-dioxane (2.5 mL) was heated to 130° C. in a sealed tube under microwave irradiation for 2 hours. The reaction mixture was concentrated under reduced pressure and the residue was chromatographed on silica gel (SNAP25) eluting with a gradient of 0-2% mixture A in dichloromethane, where mixture A is MeOH/NH$_4$OH 10:1. The partially pure product was further purified by preparative LC-MS to give 20 mg of a yellow gum. The product was dissolved in dichloromethane (4 mL) and treated with 1M HCl solution in diethyl ether (0.16 mL) causing precipitation. The resulting mixture was evaporated under reduced pressure and the residue was triturated with diethyl ether. The solids were dried to give 24 mg of 3-({3-[4-(isoquinolin-1-yl)piperazin-1-yl]propyl}amino)-2H-chromen-2-one hydrochloride 87 (Y=27%). LC-MS (M-H+)=415.3.

$^1$H NMR (400 MHz, DMSO-d$_6$) δ=11.16 (br. s., 1H), 8.19 (d, J=7.5 Hz, 1H), 8.08 (d, J=5.8 Hz, 1H), 8.00 (d, J=7.5 Hz, 1H), 7.85 (t, J=6.5 Hz, 1H), 7.70 (t, J=7.3 Hz, 1H), 7.57 (d, J=5.3 Hz, 1H), 7.47 (br. s., 1H), 7.37-7.10 (m, 3H), 6.68 (s, 1H), 6.27 (br. s., 1H), 4.00 (d, J=12.3 Hz, 2H), 4.37-3.81 (m, 1H), 3.64 (d, J=11.0 Hz, 4H), 3.40 (d, J=9.3 Hz, 2H), 3.28 (d, J=5.8 Hz, 4H), 2.11 (br. quin, J=7.0 Hz, 2H)

Preparation of compound 96: 4-({3-[4-(7-fluoroisoquinolin-1-yl)piperazin-1-yl]propyl}amino)-5-methyl-2H-chromen-2-one hydrochloride Compound 96 was prepared as described hereinbelow.

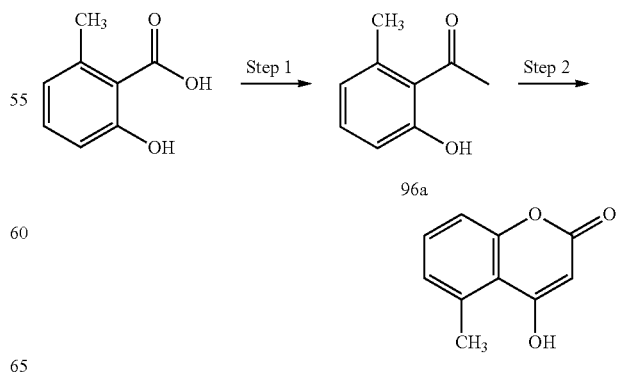

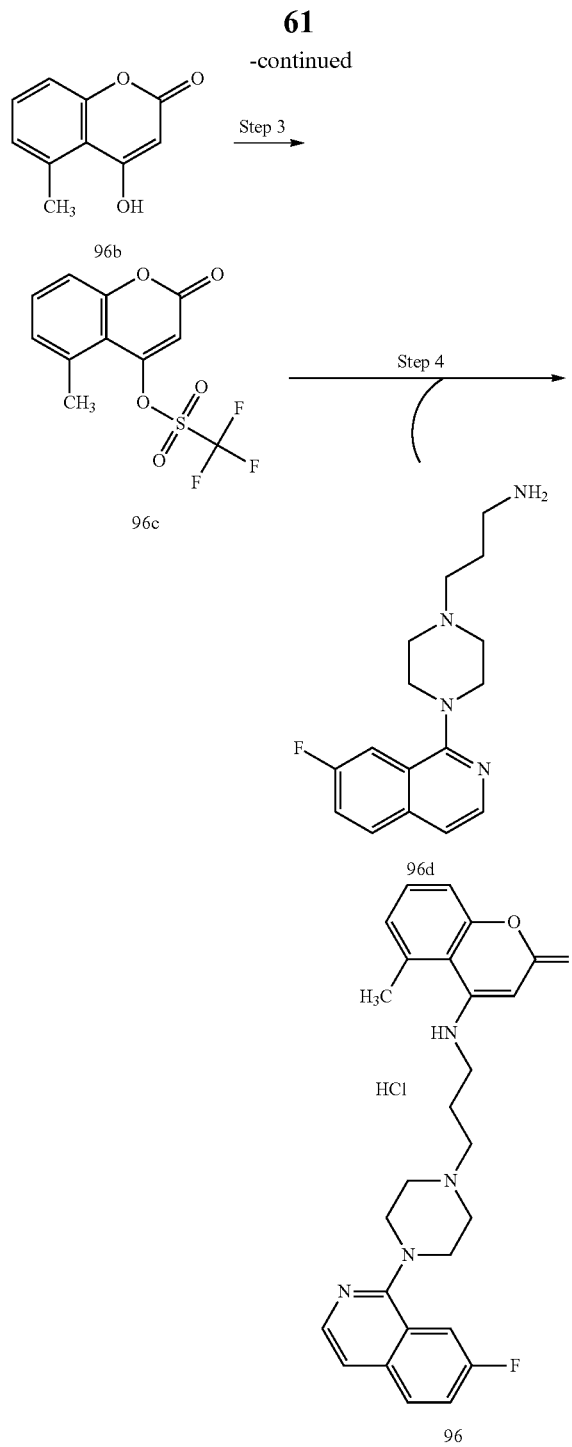

cHex/ethyl acetate 7:3 to obtain 980 mg of 1-(2-hydroxy-6-methylphenyl)ethanone 96a (Y=51%). LC-MS (M-H+)=151.0.

Step 2: 4-hydroxy-5-methyl-2H-chromen-2-one (96b)

A solution of intermediate 96a (0.98 g, 6.5 mmoles, 1 eq.) in toluene (10 mL) was added dropwise to a stirred suspension of NaH (60% dispersion in mineral oil, 0.784 g, 19.6 mmoles, 3.0) in toluene (20 mL) at room temperature. Stirring was continued for 10 minutes, then a solution of diethyl carbonate (1.58 mL, 13.1 mmoles, 2 eq.) in toluene (10 mL) was added dropwise and the mixture was heated to 115° C. for 48 h. The solvent was evaporated under reduced pressure, the solid residue was added portion-wise to ice-cold water (100 mL) to give a turbid solution. The aqueous phase was washed with diethyl ether (50 mL) then acidified with 1M HCl solution (60 mL) causing precipitation of a white solid. The solid was collected by filtration and washed with water. The wet filter cake was suspended in dichloromethane (100 mL) and evaporated under reduced pressure to give 949 mg of 4-hydroxy-5-methyl-2H-chromen-2-one 96b (Y=82%). LC-MS (M-H+)=177.0.

Step 3: 5-methyl-2-oxo-2H-chromen-4-yl trifluoromethanesulfonate (96c)

Intermediate 96c was prepared as described in step 1 of the synthesis of compound 28, using intermediate 96b (Y=58%). LC-MS (M-H$^+$)=309.0.

Step 4: 4-({3-[4-(7-fluoroisoquinolin-1-yl)piperazin-1-yl]propyl}amino)-5-methyl-2H-chromen-2-one hydrochloride (96)

Compound 96 was prepared as described in step 4 of the synthesis of compound 71, using intermediate 96d. Intermediate 96d was prepared according to the procedure described in step 2 of the synthesis of compound 31, starting from 1-chloro-7-fluoroisoquinoline (Y=31%). LC-MS (M-H$^+$)=447.3.

$^1$H NMR (400 MHz, DMSO-d$_6$) δ=11.17 (br. s., 1H), 8.13 (d, J=5.8 Hz, 1H), 8.09 (dd, J=5.5, 8.8 Hz, 1H), 7.87 (d, J=9.8 Hz, 1H), 7.74 (t, J=8.5 Hz, 1H), 7.59 (d, J=5.8 Hz, 1H), 7.44 (t, J=7.9 Hz, 1H), 7.16 (d, J=8.0 Hz, 1H), 7.12 (d, J=7.5 Hz, 1H), 6.65 (br. s., 1H), 5.59 (br. s., 1H), 5.27 (s, 1H), 3.87 (d, J=12.8 Hz, 2H), 3.63 (d, J=11.3 Hz, 2H), 3.55 (t, J=12.8 Hz, 2H), 3.44 (d, J=5.5 Hz, 4H), 3.28 (br. s., 2H), 2.84 (s, 3H), 2.27-2.06 (m, 2H)

Preparation of compound 97: 4-({3-[4-(7-fluoroisoquinolin-1-yl)piperazin-1-yl]propyl}amino)-3-methyl-2H-chromen-2-one hydrochloride Compound 97 was prepared as described hereinbelow.

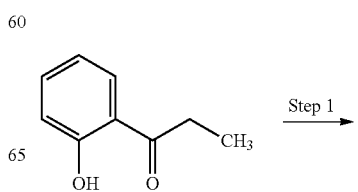

Step 1: 1-(2-hydroxy-6-methylphenyl)ethanone (96a)

A solution of 2-hydroxy-6-methylbenzoic acid (2 g, 12.7 mmoles, 1 eq.) in THF (13 mL) was cooled to −78° C. MeLi (1.6 M in Et$_2$O, 38.1 mmoles, 3 eq.) was added dropwise. The mixture was stirred at room temperature overnight then was cooled to 0° C. and quenched with sat. NH$_4$Cl. Ethyl acetate was added and the organic phase was washed with brine. The solvent was removed in vacuum and the crude material was purified by Si-column eluting with cHex to

Step 1: 4-hydroxy-3-methyl-2H-chromen-2-one (97a)

Intermediate 97a was prepared according to the procedure described in step 2 of the synthesis of compound 96, using 1-(2-hydroxyphenyl)propan-1-one (2.1 g, Y=20%). LC-MS (M-H$^+$)=177.0.

Step 2: 3-methyl-2-oxo-2H-chromen-4-yl trifluoromethanesulfonate (97b)

Intermediate 97b was prepared according to the procedure described in step 1 of the synthesis of compound 28, using intermediate 97a (Y=58%). LC-MS (M-H$^+$)=309.0.

Step 3: 4-({3-[4-(7-fluoroisoquinolin-1-yl)piperazin-1-yl]propyl}amino)-3-methyl-2H-chromen-2-one hydrochloride (97)

Compound 97 was prepared as described in step 4 of the synthesis of compound 71, using intermediate 96d. Intermediate 96d was prepared according to the procedure described in step 2 of the synthesis of compound 31, starting from 1-chloro-7-fluoroisoquinoline (Y=38%). LC-MS (M-H$^+$)=447.3.

$^1$H NMR (400 MHz, DMSO-d$_6$) δ=10.84 (br. s., 1H), 8.20-8.11 (m, 2H), 8.07 (dd, J=5.5, 9.0 Hz, 1H), 7.84 (dd, J=2.4, 10.2 Hz, 1H), 7.71 (dt, J=2.5, 8.8 Hz, 1H), 7.61-7.48 (m, 2H), 7.38-7.24 (m, 2H), 6.72 (br. s., 1H), 4.48 (br. s., 1H), 3.81 (d, J=11.8 Hz, 2H), 3.65 (t, J=6.7 Hz, 2H), 3.59 (d, J=11.0 Hz, 2H), 3.53-3.32 (m, 4H), 3.22 (br. s., 2H), 2.16 (s, 3H), 2.14-2.04 (m, 2H)

Preparation of compound 101: 4-({3-[4-(7-fluoroisoquinolin-1-yl)piperazin-1-yl]propyl}amino)-3-methyl-2H-chromen-2-one hydrochloride Compound 101 was prepared as described hereinbelow.

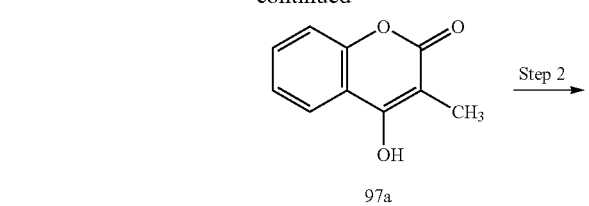
97a

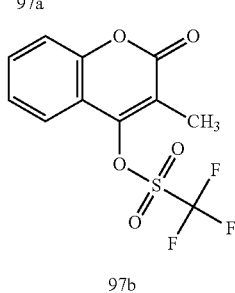
97b

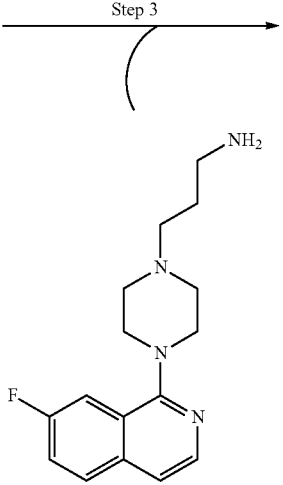
97b

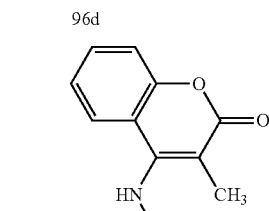
96d

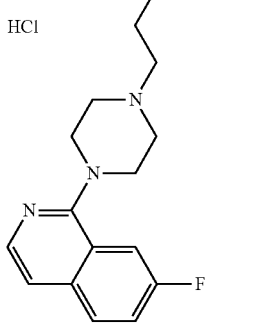
97

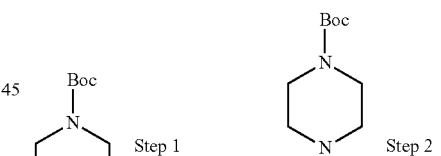
101a

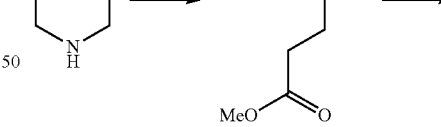
101b

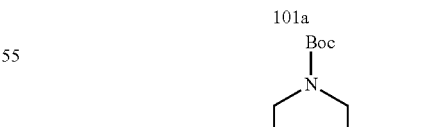
101c

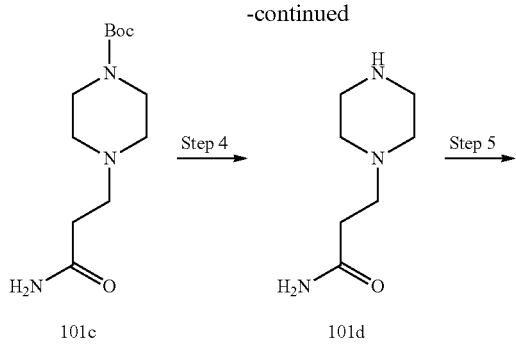

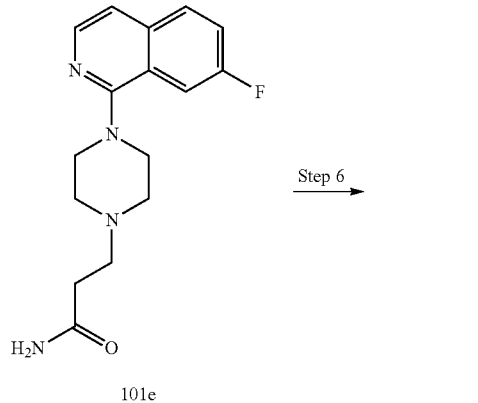

101e

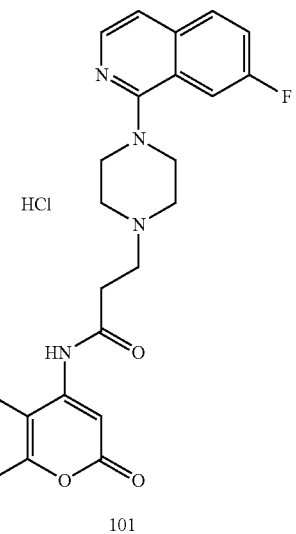

101

Step 1: tert-butyl 4-(3-methoxy-3-oxopropyl)piperazine-1-carboxylate (101a)

Methyl 3-bromopropanoate (0.607 mL, 5.56 mmoles, 1.05 eq.) was added to a solution of N-Boc-piperazine (1 g, 5.3 mmoles, 1 eq.) and TEA (0.870 mL, 6.36 mmoles, 1.2 eq.) in anhydrous THF (8 mL), and the reaction was stirred overnight at room temperature. The mixture was diluted with EtOAc, the organic phase was washed with sodium bicarbonate solution and brine, dried over sodium sulphate and evaporated under reduced pressure. The residue was chromatographed on silica gel (SNAP 25) eluting with a gradient of 20-100% of EtOAc in ciclohexane to give 1.3 g of tert-butyl 4-(3-methoxy-3-oxopropyl)piperazine-1-carboxylate 101a (Y=90%). LC-MS (M-H+)=273.2.

Step 2: 3-[4-(tert-butoxycarbonyl)piperazin-1-yl]propanoic acid (101b)

To a solution of intermediate 101a (1.3 g, 4.7 mmoles, 1 eq.) in THF/water (9:1) LiOH (123 mg, 5.17 mmoles, 1.1 eq.) was added. The mixture was stirred at 60° C. for 1 h then was concentrated under reduced pressure. The crude 3-[4-(tert-butoxycarbonyl)piperazin-1-yl]propanoic acid 101b (607 mg) was progressed without any further purification. LC-MS (M-H$^+$)=259.2.

Step 3: tert-butyl 4-(3-amino-3-oxopropyl)piperazine-1-carboxylate (101c)

Hexamethyldisilazane (0.488 mL, 2.35 mmoles, 1 eq.) was added to a stirred solution of N-(3-Dimethylaminopropyl)-N'-ethylcarbodiimide hydrochloride (540 mg, 2.82 mmoles, 1.2 eq.), 1-hydroxybenzotriazole hydrate (381 mg, 2.82 mmoles, 1.2 eq.), intermediate 101b (607 mg, 2.35 mmoles, 1 eq.) and TEA (977 µl, 7.05 mmoles, 3 eq.) in DCM (8 mL). The resulting mixture was stirred overnight at room temperature. The organic phase was washed with sodium bicarbonate solution, filtered through a hydrophobic frit (Phase Separator) and evaporated under reduce pressure. The residue was chromatographed on modified NH silica gel (SNAP 26) eluting with a gradient of 10-100% A in EtOAc, where A is MeOH/AcOEt (5:95), to give 454 mg of tert-butyl 4-(3-amino-3-oxopropyl)piperazine-1-carboxylate 101c as a white solid (Y=75%). LC-MS (M-H+)=258.2.

Step 4: 3-(piperazin-1-yl)propanamide (101d)

Intermediate 101d was prepared according to the procedure described in step 4 of the synthesis of compound 68 (Y=quant.). LC-MS (M-H$^+$)=158.1.

Step 5: 3-[4-(7-fluoroisoquinolin-1-yl)piperazin-1-yl]propanamide (101e)

Intermediate 101e was prepared as described in step 1 of the synthesis of compound 73, using 1-chloro-7-fluoroisoquinoline (Y=84%). LC-MS (M-H$^+$)=303.2.

Step 6: 4-({3-[4-(7-fluoroisoquinolin-1-yl)piperazin-1-yl]propyl}amino)-3-methyl-2H-chromen-2-one hydrochloride (101)

4-(trifluoromethane)sulfonylchromen-2-one 28a (149 mg, 0.51 mmoles, 1.3 eq.), 3-[4-(7-fluoroisoquinolin-1-yl)piperazin-1-yl]propanamide 101e (117 mg, 0.39 mmoles, 1 eq.), K$_3$PO$_4$ (165 mg, 0.78 mmoles, 2 eq.), Pd(dba)$_2$ (11 mg, 0.019 mmoles, 0.05 eq.) and Xantphos (11 mg, 0.019 mmoles, 0.05 eq.) were loaded into a Schlenk tube, which was filled with N$_2$. Dry dioxane (4 mL) was added and the resulting mixture was stirred at 100° C. for 30 min. The organic phase was washed with H$_2$O, filtered through a hydrophobic frit (Phase Separator) and evaporated under reduced pressure. The residue was chromatographed on silica gel (SNAP 10) eluting with a gradient of 50-100% of EtOAc in ciclohexane. The resultant solid was dissolved in DCM and cooled to 0° C. 3 eq. of 1M HCl in diethyl ether was added, after 1 h the mixture was evaporated in vacuo and the residue was triturated with diethyl ether to obtain 58 mg of 4-({3-[4-(7-fluoroisoquinolin-1-yl)piperazin-1-yl]propyl}amino)-3-methyl-2H-chromen-2-one hydrochloride 101 (Y=29%). LC-MS (M-H+)=447.3.

¹H NMR (400 MHz, DMSO-d₆) δ=10.81 (br. s., 1H), 10.44 (s, 1H), 8.34 (dd, J=1.4, 8.4 Hz, 1H), 8.16 (d, J=5.8 Hz, 1H), 8.08 (dd, J=5.8, 9.0 Hz, 1H), 7.86 (dd, J=2.5, 10.3 Hz, 1H), 7.76-7.66 (m, 2H), 7.58 (d, J=5.8 Hz, 1H), 7.48-7.41 (m, 2H), 7.24 (s, 1H), 4.99 (br. s., 1H), 3.85 (d, J=10.5 Hz, 2H), 3.66-3.59 (m, 2H), 3.59-3.52 (m, 2H), 3.50-3.41 (m, 4H), 3.31 (t, J=7.0 Hz, 2H)

Preparation of compound 107: 4-({3-[4-(7-fluor-oisoquinolin-1-yl)piperazin-1-yl]propyl}amino)-7-hydroxy-2H-chromen-2-one hydrochloride Compound 107 was prepared as described hereinbelow.

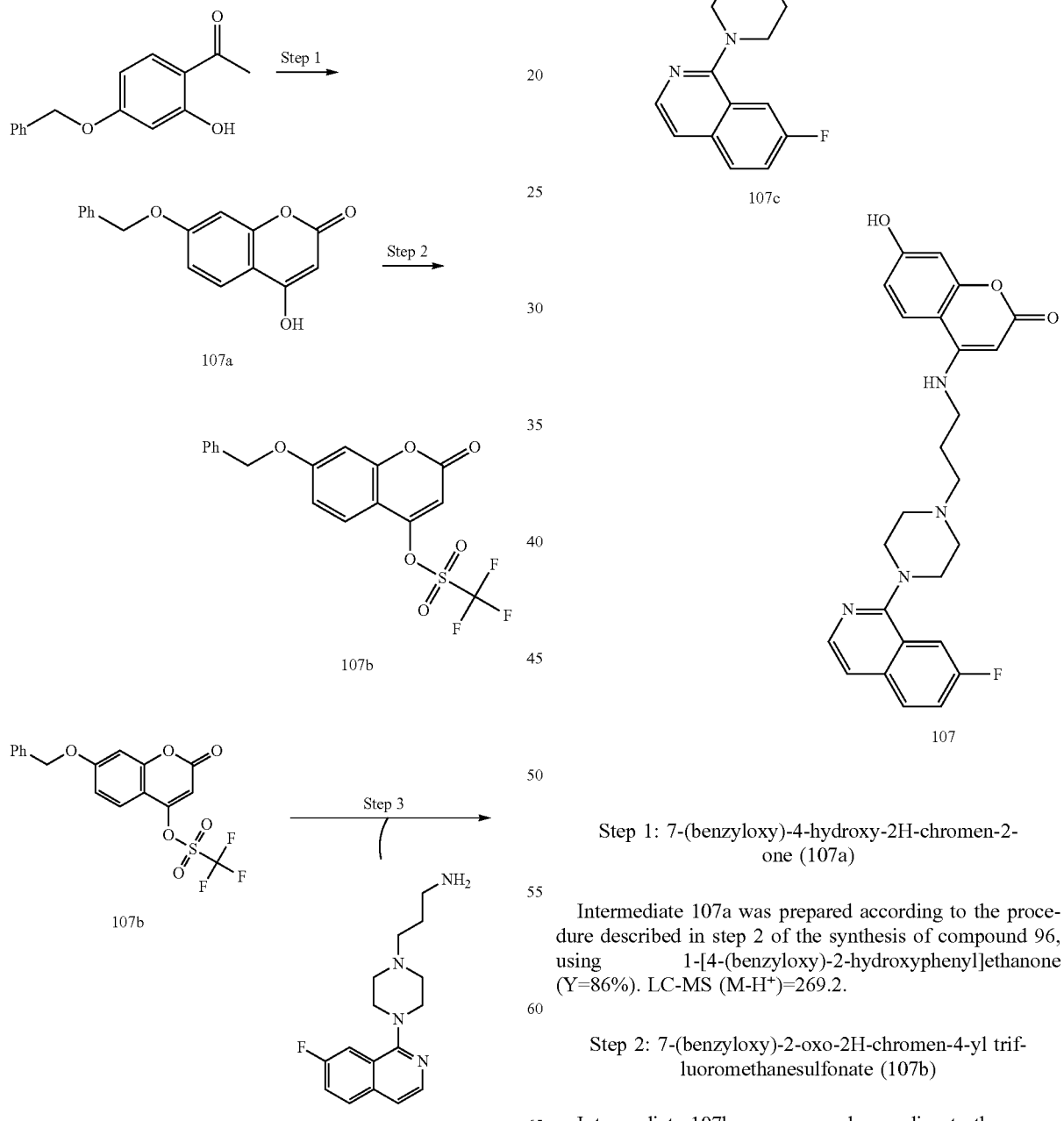

Step 1: 7-(benzyloxy)-4-hydroxy-2H-chromen-2-one (107a)

Intermediate 107a was prepared according to the procedure described in step 2 of the synthesis of compound 96, using 1-[4-(benzyloxy)-2-hydroxyphenyl]ethanone (Y=86%). LC-MS (M-H⁺)=269.2.

Step 2: 7-(benzyloxy)-2-oxo-2H-chromen-4-yl trifluoromethanesulfonate (107b)

Intermediate 107b was prepared according to the procedure described in step 1 of the synthesis of compound 28 (Y=quant.). LC-MS (M-H⁺)=401.1.

Step 3: 7-(benzyloxy)-4-({3-[4-(7-fluoroisoquinolin-1-yl)piperazin-1-yl]propyl}amino)-2H-chromen-2-one (107c)

Intermediate 107c was prepared as described in step 4 of the synthesis of compound 71, using intermediate 96d. Intermediate 96d was prepared according to the procedure described in step 2 of the synthesis of compound 31, starting from 1-chloro-7-fluoroisoquinoline (Y=37%). LC-MS (M-H$^+$)=539.4.

Step 4: 4-({3-[4-(7-fluoroisoquinolin-1-yl)piperazin-1-yl]propyl}amino)-7-hydroxy-2H-chromen-2-one hydrochloride (107)

To a suspension of intermediate 107c (49 mg, 0.09 mmoles, 1 eq.) in EtOH (4 mL) Pd/C 10% (0.05 eq.) was added and the mixture was stirred at room temperature under hydrogen (1 atm). After 30 h the mixture was filtered and concentrated in vacuum. The residue was loaded onto a SCX cartridge (1 g), which was eluted with MeOH and with a 1M NH$_3$ solution in MeOH. The basic solution was concentrated in vacuum to give a colorless oil (34 mg). This was purified by flash chromatography (Biotage KP-Sil 10 g SNAP cartridge, eluent A: EtOAc, B: EtOAc/MeOH 80/20, gradient A/B from 90:10 to 0:100) to give 18.2 mg of a white solid. The product was dissolved in MeOH and a 1 M HCl solution in diethyl ether (0.1 mL) was added. The mixture was concentrated under nitrogen and the residue was triturated with diethyl ether (2×) to give 4-({3-[4-(7-fluoroisoquinolin-1-yl)piperazin-1-yl]propyl}amino)-7-hydroxy-2H-chromen-2-one hydrochloride 107 as a white solid (18.7 mg, Y=40%). LC-MS (M-H+)=449.3.

$^1$H NMR (400 MHz, DMSO-d$_6$) δ=10.51 (br. s., 1H), 10.42 (br. s., 1H), 8.16 (d, J=5.8 Hz, 1H), 8.07 (dd, J=5.5, 9.0 Hz, 1H), 7.90 (d, J=8.8 Hz, 1H), 7.85 (dd, J=2.3, 10.3 Hz, 1H), 7.75-7.66 (m, 2H), 7.57 (d, J=5.8 Hz, 1H), 6.75 (dd, J=2.3, 8.8 Hz, 1H), 6.63 (d, J=2.3 Hz, 1H), 5.09 (s, 1H), 3.82 (d, J=8.8 Hz, 2H), 3.73 (br. s., 1H), 3.61 (d, J=6.3 Hz, 2H), 3.47-3.33 (m, 6H), 3.28 (td, J=5.0, 10.0 Hz, 2H), 2.10 (quin, J=7.2 Hz, 2H)

Preparation of compound 111: 4-({1-[(isoquinolin-1-yloxy)acetyl] piperidin-4-yl}amino)-2H-chromen-2-one Compound 111 was prepared as described hereinbelow.

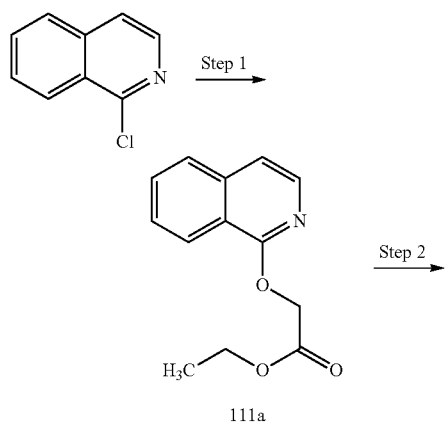

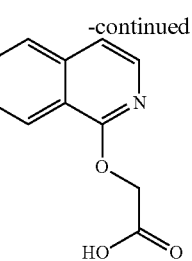

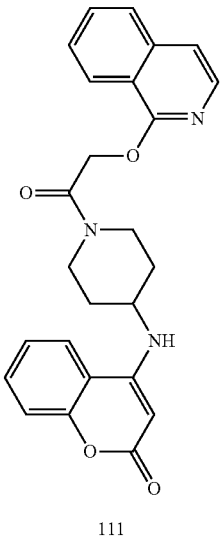

Step 1: Ethyl (isoquinolin-1-yloxy)acetate (111a)

To a suspension of ethyl hydroxyacetate (3.45 mL, 36.4 mmoles, 3 eq.) in THF (15 mL) NaH (60% dispersion in mineral oil, 1.47 g, 36.6 mmoles, 3 eq.) was added portionwise. The mixture was heated to 70° C. and stirred for 1 h then a solution of 1-chloroisoquinoline (2 g, 12.3 mmoles, 1 eq.) in THF (15 mL) was added. The reaction mixture was stirred at 70° C. overnight then was cooled to room temperature, poured into a saturated solution of NaCl (15 mL) and extracted with EtOAc (3×10 mL). The collected organic phases were dried over Na$_2$SO$_4$ and concentrated under vacuum. The residue was purified via flash chromatography on silica gel eluting with hexane/EtOAc 9:1 to give 1.85 g of ethyl (isoquinolin-1-yloxy)acetate 111a (Y=65%). GC/MS: 231.

Step 2: (isoquinolin-1-yloxy)acetic acid (111b)

To a solution of intermediate 111a (1.2 g, 5.2 mmoles) in a mixture of THF/EtOH 1:1 (10 mL) NaOH (1 M solution, 20.4 mL, 4 eq.) was added. The solution was stirred for 3 h at room temperature then the solvents were removed under vacuum, water (10 mL) was added to the residue followed by 1 M HCl (neutralization). The mixture was stirred for 15 min. then the resulting solid was filtered, washed with water and dried to give 0.83 g of (isoquinolin-1-yloxy)acetic acid 111b (Y=78%). LC-MS (M-H$^+$)=204.1.

Step 3: 4-({1-[(isoquinolin-1-yloxy)acetyl]piperidin-4-yl}amino)-2H-chromen-2-one (111)

To a solution of intermediate 111b (0.3 g, 1.48 mmoles, 1 eq.) in DMF (10 mL) TEA (0.46 mL, 3.25 mmoles, 2.2 eq.), intermediate 28c (0.5 g, 1.63 mmoles, 1.1 eq.) and HBTU (616 mg, 1.63 mmoles, 1.1 eq.) were added. The mixture was stirred at room temperature overnight then was diluted with EtOAc and filtered. The solution was washed with water and concentrated. The residue was diluted with EtOAc, a white solid separated that was filtered and dried to give 182 mg of 4-({1-[(isoquinolin-1-yloxy)acetyl]piperidin-4-yl}amino)-2H-chromen-2-one 111 (Y=29%). LC-MS (M-H$^+$)=430.2.

$^1$H NMR (300 MHz, DMSO-d$_6$) δ=8.25 (dd, J=0.7, 7.7 Hz, 1H), 8.15 (d, J=7.9 Hz, 1H), 7.97 (d, J=5.8 Hz, 1H), 7.92 (d, J=8.2 Hz, 1H), 7.79 (ddd, J=1.5, 7.0, 8.3 Hz, 1H), 7.71-7.55 (m, 2H), 7.41 (d, J=5.3 Hz, 1H), 7.38-7.25 (m, 3H), 5.40 (s, 1H), 5.34 (s, 2H), 4.35 (d, J=12.9 Hz, 1H), 4.07-3.94 (m, 1H), 3.92-3.70 (m, 1H), 3.27 (d, J=11.8 Hz, 1H), 2.81 (tdd, J=11.9, 12.1, 12.3 Hz, 1H), 2.19-1.81 (m, 2H), 1.66 (dq, J=3.0, 11.8 Hz, 1H), 1.49 (dq, J=3.0, 11.8 Hz, 1H).

Preparation of compound 117: N-(isoquinolin-1-yl)-2-{4-[(2-oxo-2H-chromen-4-yl)amino]piperidin-1-yl}acetamide Compound 117 was prepared as described hereinbelow.

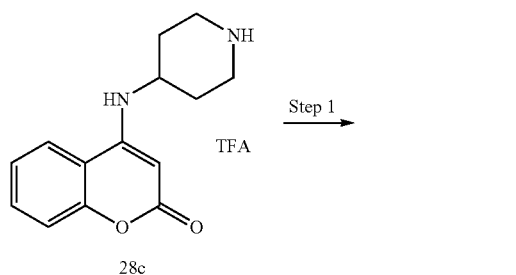

28c

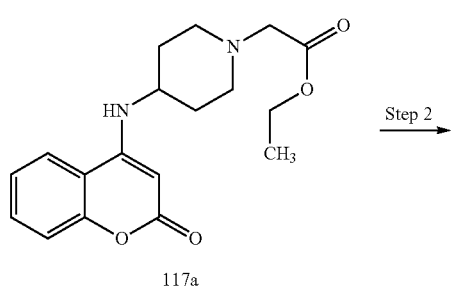

117a

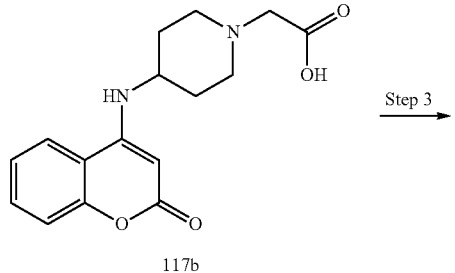

117b

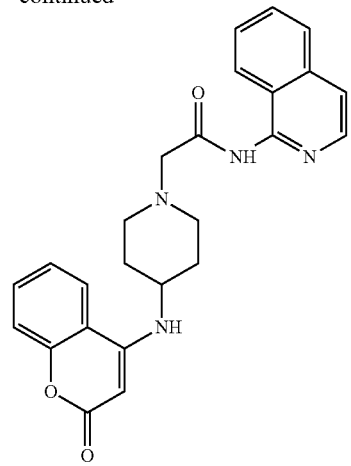

117

Step 1: Ethyl {4-[(2-oxo-2H-chromen-4-yl)amino]piperidin-1-yl}acetate (117a)

To a solution of intermediate 28c (0.64 g, 1.79 mmoles, 1 eq.) in MeCN (10 mL) K$_2$CO$_3$ (0.74 g, 5.34 mmoles, 3 eq.) was added. The mixture was stirred under reflux for 1 h then a solution of ethyl bromoacetate (0.2 mL, 1.78 mmoles, 1 eq.) in MeCN (5 mL) was added dropwise. After stirring 2 h under reflux the mixture was cooled to room temperature, diluted with EtOAc, filtered and concentrated under vacuum. The residue was purified via flash chromatography on silica gel eluting with CHCl$_3$/MeOH 9:1 to give 0.45 g of ethyl {4-[(2-oxo-2H-chromen-4-yl)amino]piperidin-1-yl}acetate 117a (Y=76%). LC-MS (M-H$^+$)=331.2.

Step 2: {4-[(2-oxo-2H-chromen-4-yl)amino]piperidin-1-yl}acetic acid (117b)

Intermediate 117b was prepared according to the procedure described in step 2 of the synthesis of compound 111, starting from intermediate 117a (Y=quant.). LC-MS (M-H$^+$)=303.1.

Step 3: N-(isoquinolin-1-yl)-2-{4-[(2-oxo-2H-chromen-4-yl)amino]piperidin-1-yl}acetamide (117)

Compound 117 was prepared according to the procedure described in step 3 of the synthesis of compound 111, using isoquinolin-1-amine (Y=43%). LC-MS (M-H$^+$)=429.2. $^1$H NMR (300 MHz, DMSO-d$_6$) δ=11.47-10.96 (m, 1H), 10.12-9.65 (m, 1H), 8.34 (br. s., 1H), 8.17 (d, J=7.7 Hz, 2H), 8.08-7.76 (m, 3H), 7.72 (t, J=7.8 Hz, 1H), 7.66-7.54 (m, 1H), 7.48-7.23 (m, 3H), 5.38 (s, 1H), 4.81-4.09 (m, 2H), 4.05-3.41 (m, 4H), 2.33-1.83 (m, 4H).

Preparation of compound 118: N-(isoquinolin-1-ylmethyl)-2-{4-[(2-oxo-2H-chromen-4-yl)amino]piperidin-1-yl}acetamide Compound 118 was prepared according to the procedure described in step 3 of the synthesis of compound 111, using intermediate 117b and 1-(isoquinolin-1-yl)methanamine (Y=26%). LC-MS (M-H$^+$)=443.2.

¹H NMR (300 MHz, DMSO-d₆) δ=8.53 (t, J=5.1 Hz, 1H), 8.47 (d, J=5.8 Hz, 1H), 8.26 (qd, J=1.0, 8.3 Hz, 1H), 8.18 (dd, J=1.3, 8.0 Hz, 1H), 8.01 (d, J=7.9 Hz, 1H), 7.86-7.76 (m, 2H), 7.72 (ddd, J=1.5, 7.0, 8.0 Hz, 1H), 7.59 (dt, J=1.5, 7.7 Hz, 1H), 7.39-7.15 (m, 3H), 5.25 (s, 1H), 5.01 (d, J=5.3 Hz, 2H), 3.63-3.39 (m, 1H), 3.07 (s, 2H), 2.95 (d, J=11.7 Hz, 2H), 2.38-2.22 (m, 2H), 2.02-1.88 (m, 2H), 1.76 (dq, J=3.6, 11.7 Hz, 2H).

Preparation of compound 119: N-(1-benzothiophen-2-ylmethyl)-3-[4-(isoquinolin-1-yl)piperazin-1-yl]propan-1-amine Compound 119 was prepared according to the procedure described in step 4 of the synthesis of compound 2 using intermediate 31b and 1-benzothiophene-2-carbaldehyde (Y=20%). LC-MS (M-H⁺)=417.2.

¹H NMR (300 MHz, CHLOROFORM-d) δ=8.13 (d, J=5.8 Hz, 1H), 8.07 (d, J=8.6 Hz, 1H), 7.83-7.66 (m, 3H), 7.60 (ddd, J=1.3, 7.0, 8.3 Hz, 1H), 7.49 (ddd, J=1.5, 7.0, 8.3 Hz, 1H), 7.36-7.27 (m, 2H), 7.24 (d, J=5.8 Hz, 1H), 7.20 (d, J=0.7 Hz, 1H), 4.14 (d, J=0.9 Hz, 2H), 3.47 (t, J=5.0 Hz, 4H), 2.85 (t, J=6.5 Hz, 3H), 2.77 (t, J=5.0 Hz, 4H), 2.59 (t, J=6.9 Hz, 2H), 1.84 (quin, J=6.7 Hz, 2H).

Preparation of compound 120: N-(1,3-benzodioxol-5-ylmethyl)-3-[4-(isoquinolin-1-yl)piperazin-1-yl]propan-1-amine Compound 120 was prepared according to the procedure described in step 4 of the synthesis of compound 2 using intermediate 31b and 1,3-benzodioxole-5-carbaldehyde (Y=10%). LC-MS (M-H⁺)=405.2.

¹H NMR (300 MHz, CHLOROFORM-d) δ=8.13 (d, J=5.8 Hz, 1H), 8.02 (d, J=8.5 Hz, 1H), 7.75 (d, J=8.0 Hz, 1H), 7.61 (ddd, J=1.1, 7.0, 8.3 Hz, 1H), 7.50 (ddd, J=1.7, 7.0, 8.3 Hz, 1H), 7.26 (dd, J=0.6, 5.8 Hz, 1H), 6.93-6.85 (m, 2H), 6.81 (d, J=7.8 Hz, 1H), 5.94 (s, 2H), 3.99 (s, 2H), 3.47-3.23 (m, 4H), 3.11 (t, J=5.9 Hz, 2H), 2.87-2.72 (m, 4H), 2.65 (t, J=5.8 Hz, 2H), 1.96 (quin, J=5.8 Hz, 2H).

Preparation of compound 122: 4-({3-[4-(7-fluoroisoquinolin-1-yl)piperazin-1-yl]propyl}amino)-5,6,7,8-tetrahydro-2H-pyrano[3,2-c]pyridin-2-one hydrochloride Compound 122 was prepared as described hereinbelow.

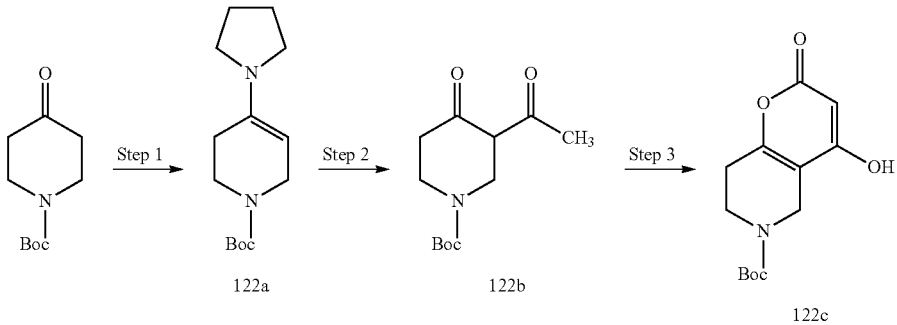

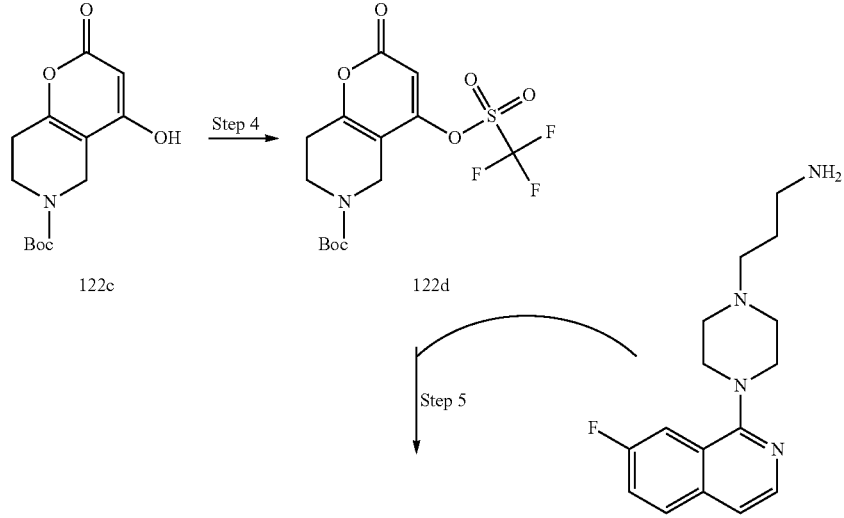

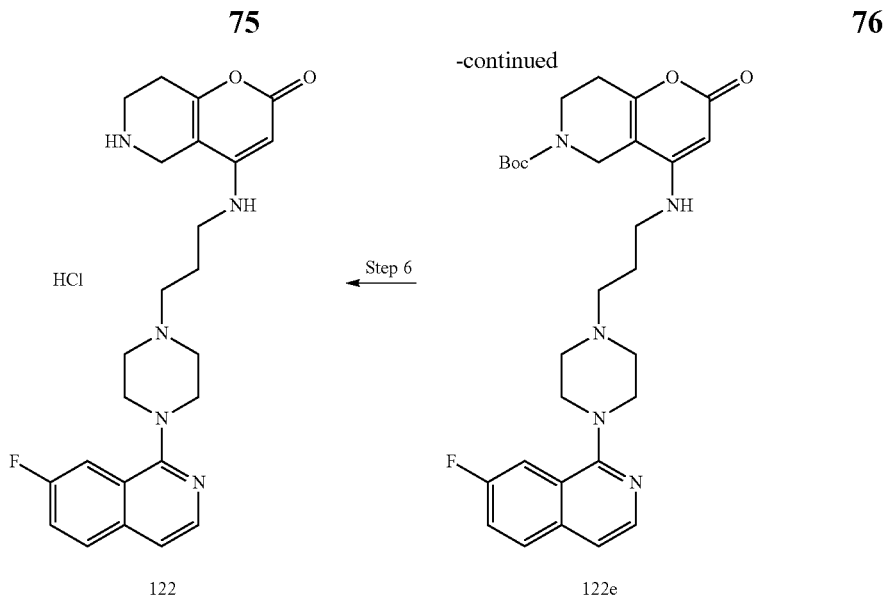

Step 1: tert-butyl 4-(pyrrolidin-1-yl)-3,6-dihydro-pyridine-1(2H)-carboxylate (122a)

Pyrrolidine (3.5 g, 50.2 mmoles, 2 eq.) was added to a solution of 1-Boc-4-piperidone (5 g, 25 mmoles, 1 eq.) in dry toluene (30 mL). The mixture was heated at 90° C. with a Dean-Stark apparatus. After 3 h the mixture was concentrated in vacuum to give tert-butyl 4-(pyrrolidin-1-yl)-3,6-dihydropyridine-1(2H)-carboxylate 122a as yellow oil (6.3 g, Y=quant.). The compound was used without any further purification and characterization.

Step 2: tert-butyl 3-acetyl-4-oxopiperidine-1-carboxylate (122b)

Intermediate 122a (6.3 g, 25 mmoles, 1 eq.) was dissolved in 1,4-dioxane (25 mL). Acetic anhydride (5.21 mL, 55.2 mmol, 2.2 eq.) was added and the resulting mixture was allowed to stand at room temperature under nitrogen for 2 days. Water (6 mL) was added and the resulting mixture was refluxed for 1 hour then cooled to room temperature and concentrated in vacuum. Water (20 mL) was added and the aqueous phase was extracted twice with EtOAc (20 mL). The combined organics extracts were washed with a 5% w/w HCl aqueous solution (20 mL), dried over MgSO$_4$ and concentrated in vacuum. The resultant orange oil was purified by Si-column eluting with cyclohexane to cyclohexane/ethyl acetate 9:1 to afford 2.98 g of tert-butyl 3-acetyl-4-oxopiperidine-1-carboxylate 122b (Y=49%). LC-MS (M-H+)=242.2.

Step 3: tert-butyl 4-hydroxy-2-oxo-7,8-dihydro-2H-pyrano[3,2-c]pyridine-6(5H)-carboxylate (122c)

A solution of intermediate 122b (1 g, 4.14 mmoles, 1 eq.) in THF (20 mL) was cooled to −78° C. Lithium bis(trimethylsilyl)amide (1 M solution in THF, 12.4 mL, 3 eq.) was added dropwise. After stirring for 1 h at −78° C., dimethylcarbonate (0.4 mL, 4.6 mmoles, 1.1 eq.) was added. The resulting mixture was allowed to warm slowly to −10° C. After 1 h the reaction was cooled to 0° C. and quenched with 1 M HCl until pH=6. Ethyl acetate was added, the organic phase was separated, washed with brine and evaporated in vacuum to obtain crude tert-butyl 3-(3-methoxy-3-oxopropanoyl)-4-oxopiperidine-1-carboxylate, that was used without any further purification.

The crude material was dissolved in toluene (8 mL), 1,8-diazabicyclo[5.4.0]undec-7-ene (0.62 mL, 4.14 mmoles, 1 eq.) was added and the mixture was stirred under reflux. After 3 hours the reaction was cooled to 0° C. and quenched with 1 M HCl. Ethyl acetate was added, the organic phase was separated, washed with brine and evaporated in vacuum. The crude material was purified by Si-column eluting with EtOAc to EtOAc/MeOH 7:3 to obtain 600 mg of tert-butyl 4-hydroxy-2-oxo-7,8-dihydro-2H-pyrano[3,2-c]pyridine-6(5H)-carboxylate 122c (Y=54%). LC-MS (M-H+)=268.2.

Step 4: tert-butyl 2-oxo-4-{[(trifluoromethyl)sulfonyl]oxy}-7,8-dihydro-2H-pyrano[3,2-c]pyridine-6(5H)-carboxylate (122d)

Intermediate 122d was prepared according to the procedure described in step 1 of the synthesis of compound 28 (Y=quant.). LC-MS (M-H+)=400.1.

Step 5: tert-butyl 4-({3-[4-(7-fluoroisoquinolin-1-yl)piperazin-1-yl]propyl}amino)-2-oxo-7,8-dihydro-2H-pyrano[3,2-c]pyridine-6(5H)-carboxylate (122e)

Intermediate 122e (Y=17%) was prepared as described in step 4 of the synthesis of compound 71, using intermediate 96d. Intermediate 96d was prepared according to the procedure described in step 2 of the synthesis of compound 31, starting from 1-chloro-7-fluoroisoquinoline. LC-MS (M-H+)=538.4.

Step 6: 4-({3-[4-(7-fluoroisoquinolin-1-yl)piperazin-1-yl]propyl}amino)-5,6,7,8-tetrahydro-2H-pyrano[3,2-c]pyridin-2-one hydrochloride (122)

Compound 122 was prepared as described in step 4 of the synthesis of compound 68 (Y=72%). LC-MS (M-H+)=438.2.

$^1$H NMR (400 MHz, DMSO-d$_6$) δ=10.74 (br. s., 1H), 9.61 (br. s., 2H), 8.16 (d, J=5.8 Hz, 1H), 8.07 (dd, J=5.8, 9.0 Hz,

1H), 7.84 (dd, J=2.5, 10.3 Hz, 1H), 7.71 (dt, J=2.5, 8.8 Hz, 1H), 7.57 (d, J=5.8 Hz, 1H), 7.16 (t, J=5.3 Hz, 1H), 5.06 (s, 1H), 4.16-3.86 (m, 3H), 3.81 (d, J=10.8 Hz, 2H), 3.59 (d, J=9.0 Hz, 2H), 3.50-3.32 (m, 6H), 3.31-3.16 (m, 4H), 2.73 (t, J=5.8 Hz, 2H), 2.14-1.93 (m, J=7.0, 7.0, 7.0, 7.0 Hz, 2H).

Preparation of Compound 123

Compound 123 was prepared as described herein below.

Step 2: tert-butyl 4-[(2-oxo-2H-chromen-4-yl)amino]piperidine-1-carboxylate (123b)

Triethylamine (1 mL, 7.2 mmoles, 1.2 eq.) in acetonitrile (2 mL) was added dropwise to a stirred solution of intermediate 123a (1.76 g, 5.99 mmoles, 1 eq.) and 1-Boc-4-aminopiperidine (1.2 g, 5.99 mmoles, 1 eq.) in dry acetonitrile (20 mL). The mixture was heated at reflux for 2 h then was cooled to room temperature, diluted with DCM (100

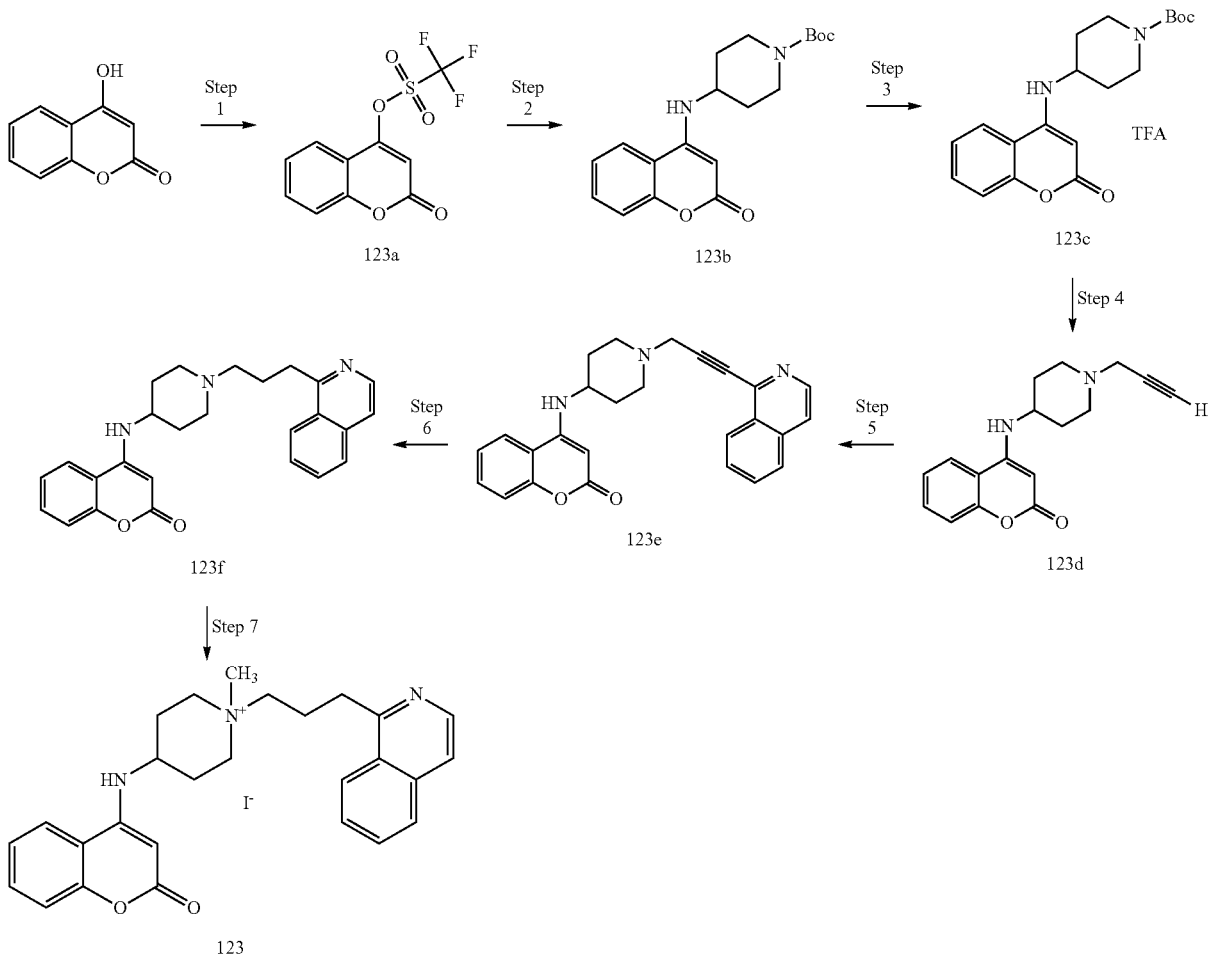

mL) and washed with saturated NaHCO3 (50 mL) and water (50 mL). The organic phase was separated, dried over sodium sulfate and evaporated in vacuum. The crude material was purified by trituration with methanol to obtain tert-butyl 4-[(2-oxo-2H-chromen-4-yl)amino]piperidine-1-carboxylate 123b (1.51 g, Y=73%). LC-MS (M-H+): 345.2.

Step 3: 4-(piperidin-4-ylamino)-2H-chromen-2-one trifluoroacetic acid salt (123c)

Intermediate 123b (1 g, 2.90 mmoles, 1 eq.) was dissolved in DCM (10 ml) and TFA (3 mL) was added dropwise at 0° C. The solution was left stirring for 2 h then was concentrated in vacuum and washed with toluene (25 ml) and diethyl ether (25 ml) to obtain 4-(piperidin-4-ylamino)-2H-chromen-2-one trifluoroacetic acid salt 123c, which was used without any further purification (1.22 g, Y=quant.). LC-MS (M-H+): 245.1.

Step 1: 2-oxo-2H-chromen-4-yl trifluoromethanesulfonate (123a)

4-Hydroxycoumarine (1 g, 6.17 mmoles, 1 eq.) was dissolved in DCM (30 mL), triethylamine (1.72 mL, 12.34 mmoles, 2 eq.) was added and the resulting mixture was cooled to −10° C. Trifluoromethanesulfonic anhydride (1.25 mL, 7.4 mmoles, 1.2 eq.) in DCM (5 mL) was added dropwise and the solution was left stirring at −10° C. for 2 h. The resulting reddish brown solution was warmed to room temperature, diluted with cHex/Et2O 1/1 (50 mL) and filtered through a pad of silica gel using cHex/Et2O 1/1 as eluent. The solvent was removed in vacuum to obtain 2-oxo-2H-chromen-4-yl trifluoromethanesulfonate 123a (1.76 g, Y=97%). LC-MS (M-H+): 295.0.

Step 4: 4-{[1-(prop-2-yn-1-yl)piperidin-4-yl]amino}-2H-chromen-2-one (123d)

To a solution of intermediate 123c (50 mg, 0.14 mmoles, 1 eq.) and potassium carbonate (38.7 mg, 0.28 mmoles, 2 eq.) in DMF (2 mL) 3-bromo-1-propyne (20.8 mg, 0.14 mmoles, 1 eq.) was added at room temperature. The reaction was left stirring overnight then was filtered and the filtrate concentrated. The residue was purified by Si-column eluting with eluting with EtOAc to EtOAc/Methanol 8:2 to give 4-{[1-(prop-2-yn-1-yl)piperidin-4-yl]amino}-2H-chromen-2-one 123d (25.6 mg, Y=64%). LC-MS (M-H+): 283.1.

Step 5: 4-({1-[3-(isoquinolin-1-yl)prop-2-yn-1-yl]piperidin-4-yl}amino)-2H-chromen-2-one (123e)

Intermediate 123d (186 mg, 0.66 mmoles, 1 eq.), 1-chloroisoquinoline (120 mg, 0.72 mmoles, 1.1 eq.) and CuI (12 mg, 0.066 mmoles, 0.1 eq.) were dissolved in dry DMF (3.6 ml). DIPEA (0.473 ml, 2.64 mmoles, 4 eq.) was added. The mixture was degassed by alternatively applying vacuum and nitrogen, then bis(triphenylphosphine)palladium(II) dichloride (45 mg, 0.066 mmoles, 0.1 eq.) was added and the mixture was heated at 60° C. After 3 h water (10 mL) was added and the mixture was extracted with ethyl acetate (3×10 mL). The organic phase was washed with brine, dried over Na2SO4, filtered and concentrated in vacuum to give 283 mg of crude material. After purification by Si-column eluting with EtOAc to EtOAc/MeOH 8:2 compound 4-({1-[3-(isoquinolin-1-yl)prop-2-yn-1-yl]piperidin-4-yl}amino)-2H-chromen-2-one 123e (87 mg, Y=32%) was obtained. LC-MS (M-H+): 410.2.

Step 6—Synthesis of 4-({1-[3-(isoquinolin-1-yl)propyl]piperidin-4-yl}amino)-2H-chromen-2-one (123f)

To a solution of intermediate 123e 4-({1-[3-(isoquinolin-1-yl)prop-2-yn-1-yl]piperidin-4-yl}amino)-2H-chromen-2-one (82 mg, 0.2 mmoles, 1 eq.) in EtOAc (5 ml) Pd/C 10% (0.05 eq.) was added and the mixture was stirred under hydrogen (3.5 atm) at room temperature. After 3 hours DCM was added, the mixture was then filtered and concentrated in vacuum to give crude material, which was purified by Si-column eluting with DCM to DCM/Methanol 8:2 to give 30 mg (0.072 mmol, 36% yield) of intermediate 123f. LC-MS (M-H$^+$): 414.1

Step 7—Synthesis of 3-cyclohexyl-3-[(2-{[1-(7-fluoroisoquinolin-1-yl)piperidin-4-yl]amino}ethyl)amino]propan-1-ol (compound 123)

To a solution of 4-({1-[3-(isoquinolin-1-yl)propyl]piperidin-4-yl}amino)-2H-chromen-2-one (123f, 25 mg, 0.06 mmol) in acetone (5 mL) K2CO3 (43 mg, 0.31 mmol) was added. After stirring 1 h the mixture was cooled to 0° C. then methyl iodide (3.7 μL, 0.06 mmol) was added. The mixture was left to return to room temperature then was stirred overnight, filtered and concentrated in vacuo. The residue was purified via preparative HPLC (C18, acetonitrile from 10% to 30% in water) to give 13.3 mg (0.024 mmol, 40% yield) of the title compound. LC-MS (M-H$^+$): 428.2
$^1$H NMR (300 MHz, DMSO-d$_6$) δ=8.44 (d, J=5.6 Hz, 1H), 8.32 (d, J=8.5 Hz, 1H), 8.16-8.09 (m, 1H), 7.99 (d, J=7.6 Hz, 1H), 7.83-7.76 (m, 1H), 7.76-7.68 (m, 2H), 7.67-7.58 (m, 1H), 7.54 (d, J=7.3 Hz, 1H), 7.40-7.30 (m, 2H), 5.36 (s, 1H), 3.96-3.79 (m, 1H), 3.75-3.59 (m, 4H), 3.57-3.36 (m, 4H), 3.13 (s, 3H), 2.39-2.05 (m, 6H).

Preparation of compound 128: (2S,3S) and (2R,3R) 4-({3-[1-(7-fluoroisoquinolin-1-yl)piperidin-4-yl]-2,3-dihydroxypropyl}amino)-2H-chromen-2-one hydrochloride Compound 128 was prepared as described hereinbelow.

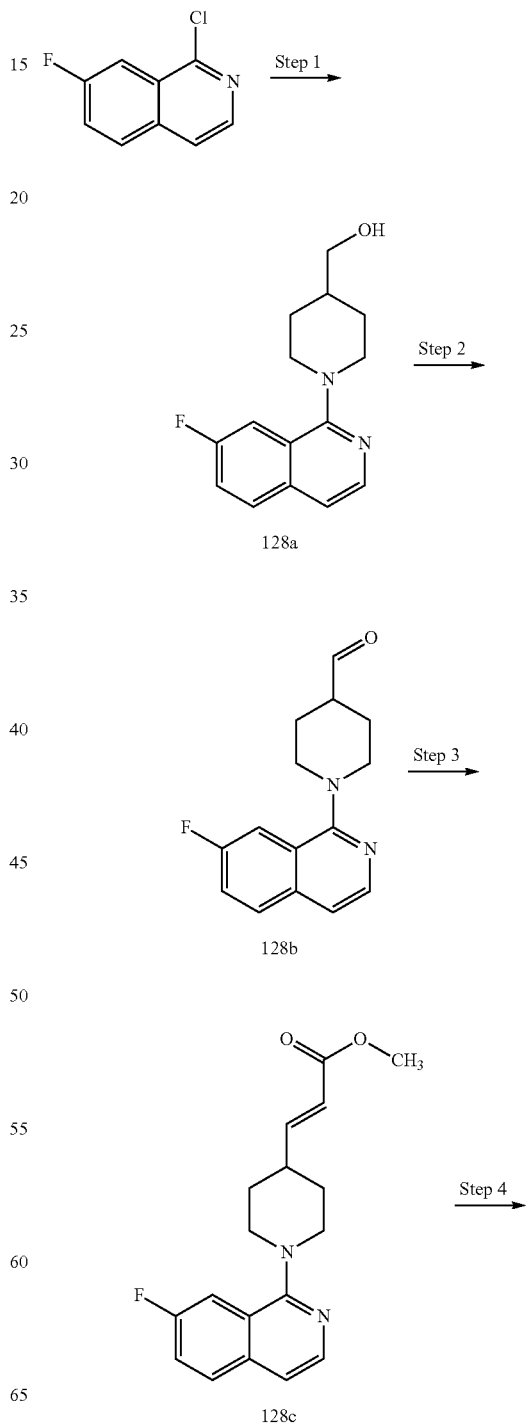

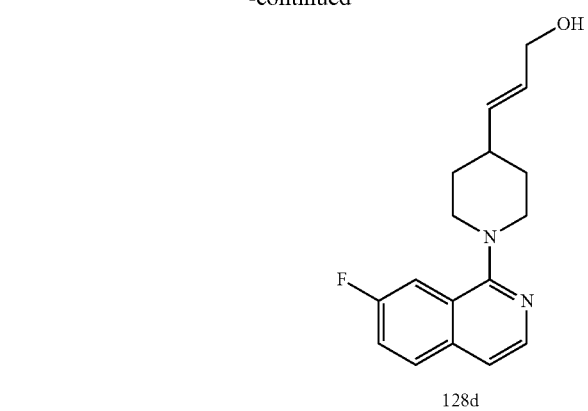

128d

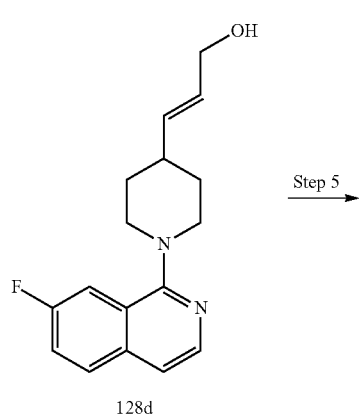

128d

Step 5 →

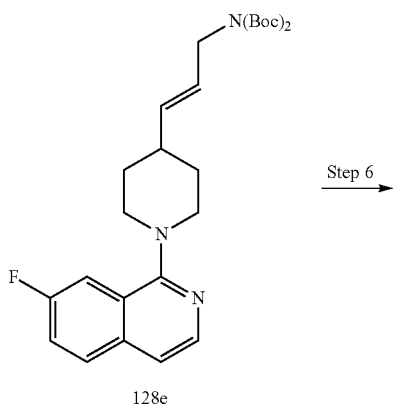

128e

Step 6 →

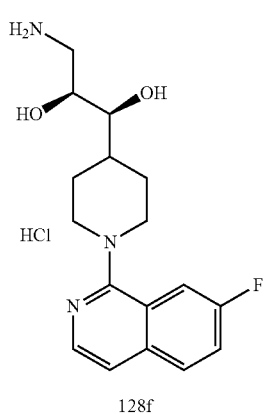

128f

Step 7 →

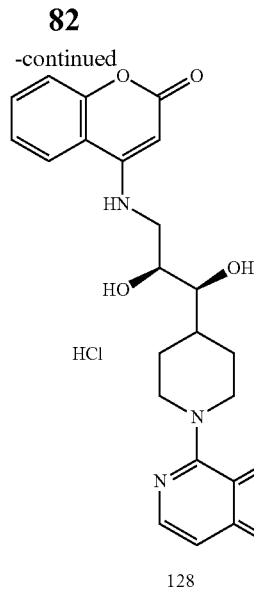

128

Step 1: [1-(7-fluoroisoquinolin-1-yl)piperidin-4-yl]methanol (128a)

Intermediate 128a was prepared according to the procedure described in step 1 of the synthesis of compound 70, using piperidin-4-ylmethanol (Y=82%). LC-MS (M-H+)=261.2.

Step 2: 1-(7-fluoroisoquinolin-1-yl)piperidine-4-carbaldehyde (128b)

Intermediate 128a (675 mg, 2.6 mmoles, 1 eq.), sodium bicarbonate (1.09 g, 13 mmoles, 5 eq.) and Dess-Martin periodinane (1.65 g, 3.9 mmoles, 1.5 eq.) were suspended in DCM (4 mL). The reaction mixture was stirred at r.t. for 3 hours then was quenched with sat. NaHCO$_3$/2N Na$_2$S$_2$O$_3$ in a 1:1 ratio. After 15 minutes water and DCM were added, the organic phase was separated, washed with brine, treated with Na$_2$SO$_4$ and concentrated under reduced pressure to give 1-(7-fluoroisoquinolin-1-yl)piperidine-4-carbaldehyde 128b, which was progressed without any further purification (671 mg, Y=quant.). LC-MS (M-H+)=259.1.

Step 3: methyl (2E)-3-[1-(7-fluoroisoquinolin-1-yl)piperidin-4-yl]prop-2-enoate (128c)

Methyl 2-(dimethoxyphosphoryl)acetate (224 mg, 1.23 mmoles, 1.6 eq.) was added to a solution of potassium tert-butoxide (138 mg, 1.23 mmoles, 1.6 eq.) in THF (3 mL) at 0° C. The mixture was stirred at room temperature for 30 min. then a solution of intermediate 128b (199 mg, 0.77 mmoles, 1 eq.) in THF (2 mL) was added dropwise at 0° C. The reaction was stirred at room temperature overnight. The reaction was quenched with water and extracted with EtOAc (2×). The organic phase was dried over sodium sulphate and evaporated under reduced pressure. The residue was chromatographed on silica gel (SNAP 10) eluting with a gradient of 0-30% EtOAc in cyclohexane to give 125 mg of methyl (2E)-3-[1-(7-fluoroisoquinolin-1-yl)piperidin-4-yl]prop-2-enoate 128c (Y=52%). LC-MS (M-H+)=315.1.

Step 4: (2E)-3-[1-(7-fluoroisoquinolin-1-yl)piperidin-4-yl]prop-2-en-1-ol (128d)

Diisobutylaluminum hydride (1 M solution in cyclohexane, 13 mL, 3.7 eq.) was added dropwise to a stirred solution of 128d (1.1 g, 3.5 mmoles, 1 eq.) in THF (25 mL) at −78° C. The mixture was stirred for 1 hour at the same temperature then was quenched with MeOH (4 mL) and was allowed to warm to room temperature. EtOAc (100 mL) and Rochelle saturated solution (150 mL) were added, the resulting mixture was stirred vigorously for 15 minutes, the organic phase was separated and dried over sodium sulphate. The volatiles were removed under reduced pressure to give 0.9 g of (2E)-3-[1-(7-fluoroisoquinolin-1-yl)piperidin-4-yl]prop-2-en-1-ol 128d (Y=90%). LC-MS (M-H+)=287.4.

Step 5: di-tert-butyl {(2E)-3-[1-(7-fluoroisoquinolin-1-yl)piperidin-4-yl]prop-2-en-1-yl}imidodicarbonate (128e)

To a solution of intermediate 128d (800 mg, 2.8 mmoles, 1 eq.) in DCM (4.5 mL) TEA (0.97 mL, 7 mmoles, 2.5 eq.) was added. The mixture was cooled to 0° C. then methanesulfanonyl chloride (0.26 mL, 3.35 mmoles, 1.2 eq.) was added under $N_2$ atmosphere. The mixture was allowed to warm to room temperature and stirred for 1 h. DCM was added and the solution was washed with sat. $NaHCO_3$. The organic phase was separated and evaporated in vacuum to give (2E)-3-[1-(7-fluoroisoquinolin-1-yl)piperidin-4-yl]prop-2-en-1-yl methanesulfonate (Y=quant.), that was used without any further purification.

The intermediate (2E)-3-[1-(7-fluoroisoquinolin-1-yl)piperidin-4-yl]prop-2-en-1-yl methanesulfonate (2.8 mmoles, 1 eq.) was added dropwise to a stirred mixture of di-tert-butyl-iminodicarboxylate (1 g, 4.75 mmoles, 1.7 eq.), $K_2CO_3$ (0.7 g, 5 mmoles, 1.8 eq.) and LII (12 mg, 0.092 mmoles, 0.03 eq.) in acetonitrile (20 mL). The reaction was refluxed overnight then sat. $NaHCO_3$ and EtOAc were added. The organic phase was washed with brine and dried over sodium sulphate. The residue was chromatographed on silica gel (SNAP 50) eluting with a gradient of 0-15% solution A in cHex, where A is 20% MeOH in EtOAc, to give 580 mg of di-tert-butyl {(2E)-3-[1-(7-fluoroisoquinolin-1-yl)piperidin-4-yl]prop-2-en-1-yl}imidodicarbonate 128e (Y=48%). LC-MS (M-H+)=486.4.

Step 6: (2S,3S) and (2R,3R) 3-amino-1-[1-(7-fluoroisoquinolin-1-yl)piperidin-4-yl]propane-1,2-diol hydrochloride (128f)

To a stirred solution of intermediate 128e (580 mg, 1.2 mmoles, 1 eq.) in t-butanol/water 1:1 (8 mL) 4-methylmorpholine-N-oxide (167 mg, 1.4 mmoles, 1.2 eq.) and one drop of osmium tetroxide (4% water solution) were added. After stirring 18 hours at room temperature, EtOAc was added and the organic phase was washed with water and brine, separated and evaporated in vacuum. 300 mg of the residue was dissolved in DCM/MeOH (5 mL) and cooled to 0° C. 3 eq. of 1 M HCl in diethyl ether were added and the mixture was stirred at room temperature overnight and then at 60° C. for 5 h. The solvent was evaporated in vacuum to obtain 199 mg of (1S,2S)-3-amino-1-[1-(7-fluoroisoquinolin-1-yl)piperidin-4-yl]propane-1,2-diol hydrochloride 128f as a racemic mixture (Y=95%). LC-MS (M-H+)=320.1.

Step 7: (2S,3S) and (2R,3R) 4-({3-[1-(7-fluoroisoquinolin-1-yl)piperidin-4-yl]-2,3-dihydroxypropyl}amino)-2H-chromen-2-one hydrochloride (128)

Compound 128, as a racemic mixture, was prepared as described in step 4 of the synthesis of compound 71, using intermediates 128f and 28a (Y=86%). LC-MS (M-H+)=464.3.

$^1$H NMR (500 MHz, DMSO-$d_6$) δ ppm 1.46-1.61 (m, 2H), 1.73-1.84 (m, 2H), 2.06-2.13 (m, 1H), 2.77-2.88 (m, 1H), 3.25 (t, J=7.83 Hz, 1H), 3.29-3.36 (m, 1H), 3.40-3.48 (m, 1H), 3.64-3.77 (m, 2H), 3.84-3.98 (m, 1H), 4.45 (d, J=7.83 Hz, 1H), 4.83 (d, J=6.36 Hz, 1H), 5.24 (s, 1H), 7.29-7.36 (m, 2H), 7.40 (d, J=5.87 Hz, 1H), 7.56-7.71 (m, 4H), 7.98 (dd, J=8.80, 5.87 Hz, 1H), 8.07 (d, J=7.83 Hz, 1H), 8.09 (d, J=5.87 Hz, 1H).

Preparation of compound 129: (2R,3S) and (2S,3R) 4-({3-[1-(7-fluoroisoquinolin-1-yl)piperidin-4-yl]-2,3-dihydroxypropyl}amino)-2H-chromen-2-one hydrochloride Compound 129 was prepared as described hereinbelow.

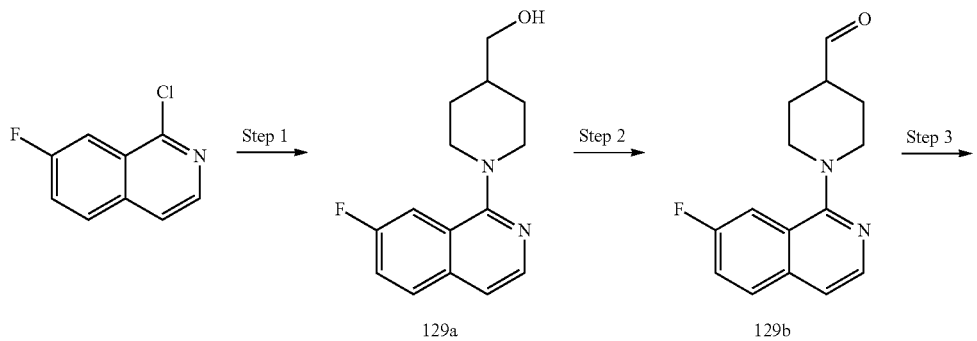

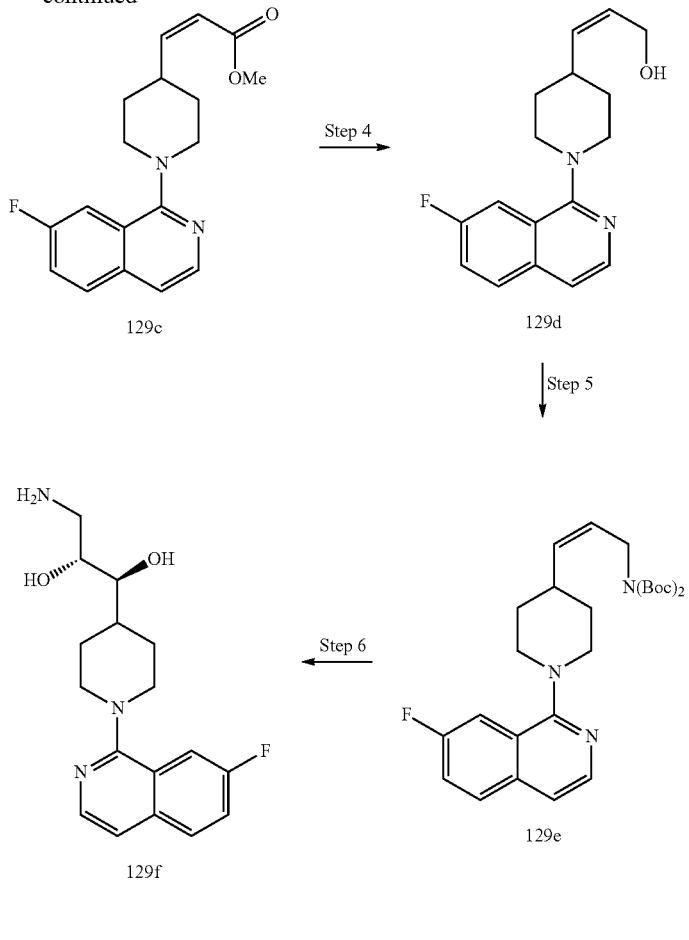

Compound 129, as a racemic mixture, was prepared as described for the synthesis of compound 128, using methyl (2Z)-3-[1-(7-fluoroisoquinolin-1-yl)piperidin-4-yl]prop-2-enoate as key intermediate. LC-MS (M-H+)=464.3.

$^1$H NMR (500 MHz, DMSO-$d_6$) δ ppm 1.58-1.96 (m, 4H), 2.05 (br. s., 1H), 3.11-3.27 (m, 3H), 3.33 (dd, J=7.83, 2.93 Hz, 1H), 3.61-3.69 (m, 1H), 3.71-3.79 (m, 1H), 4.00 (br. s., 2H), 5.23 (s, 1H), 7.25-7.38 (m, 2H), 7.53 (d, J=5.87 Hz, 1H), 7.59 (t, J=7.58 Hz, 1H), 7.72-7.77 (m, 1H), 7.82 (d, J=9.78 Hz, 2H), 7.93 (d, J=4.40 Hz, 1H), 8.13 (d, J=7.83 Hz, 2H)

Preparation of compound 130: N-(1,3-benzodioxol-5-ylmethyl)-2-[4-(isoquinolin-1-yl)piperazin-1-yl]ethanamine Compound 130 was prepared according to the procedure described in step 4 of the synthesis of compound 2, using intermediate 75b and 1,3-benzodioxole-5-carbaldehyde (Y=25%). LC-MS (M-H+)=391.2.

$^1$H NMR (300 MHz, DMSO-$d_6$) δ=8.09 (d, J=5.7 Hz, 2H), 8.08 (d, J=8.5 Hz, 1H), 7.89 (dd, J=0.9, 8.3 Hz, 1H), 7.71 (ddd, J=1.2, 6.8, 8.0 Hz, 1H), 7.61 (ddd, J=1.2, 6.8, 8.4 Hz, 1H), 7.40 (d, J=5.4 Hz, 1H), 7.05 (t, J=1.0 Hz, 1H), 6.95 (d, J=1.0 Hz, 2H), 6.02 (s, 2H), 3.97 (s, 2H), 3.34 (br. s., 4H), 2.94 (t, J=6.2 Hz, 2H), 2.76-2.58 (m, 6H).

Preparation of Compound 136

Compound 136 was prepared as described herein below.

Step 1—Synthesis of 3-cyclohexyl-3-({(2R)-3-[4-(7-fluoroisoquinolin-1-yl)piperazin-1-yl]-2-hydroxypropyl}amino)propanoic acid (formate salt, compound 136)

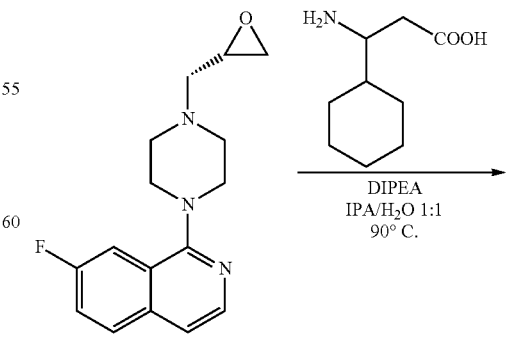

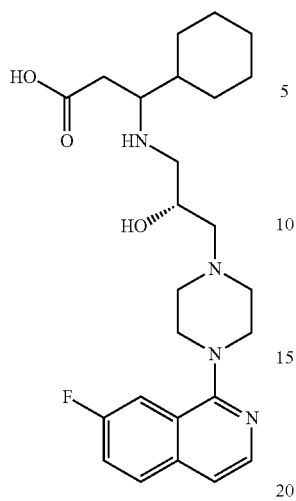

Compound 3-cyclohexyl-3-({(2R)-3-[4-(7-fluoroisoquinolin-1-yl) piperazin-1-yl]-2-hydroxypropyl}amino)propanoic acid (formate salt) as a mixture of diastereoisomers was prepared according to the synthesis described for compound 139 using racemic 3-amino-3-cyclohexylpropanoic acid (Y=44%).

LC-MS (M-H⁺)=459.5. ¹H NMR (500 MHz, DMSO-d6) δ ppm 0.86-1.29 (m, 5H), 1.49-1.79 (m, 6H), 2.05-2.17 (m, 1H), 2.25 (dt, J=16.14, 4.16 Hz, 1H), 2.48 (d, J=7.34 Hz, 2H), 2.62-2.79 (m, 5H), 2.80-2.95 (m, 2H), 3.28 (br. s., 4H), 3.84-3.94 (m, 1H), 7.45 (d, J=5.38 Hz, 1H), 7.65 (td, J=8.68, 2.69 Hz, 1H), 7.69 (d, J=9.78 Hz, 1H), 8.01 (dd, J=9.05, 5.62 Hz, 1H), 8.12 (d, J=5.87 Hz, 1H), 8.15 (s, 1H).

Preparation of Compound 137

Compound 137 was prepared as described herein below.

Step 1—Synthesis of 3-cyclohexyl-3-({(2S)-3-[4-(7-fluoroisoquinolin-1-yl)piperazin-1-yl]-2-hydroxypropyl}amino)propanoic acid (formate salt, compound 137)

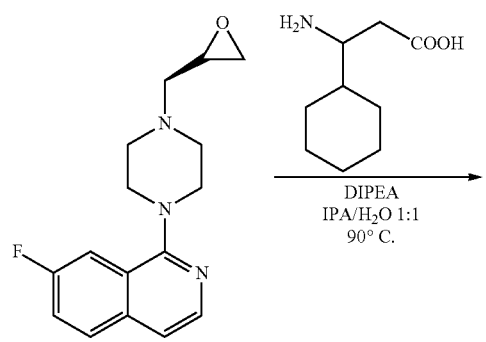

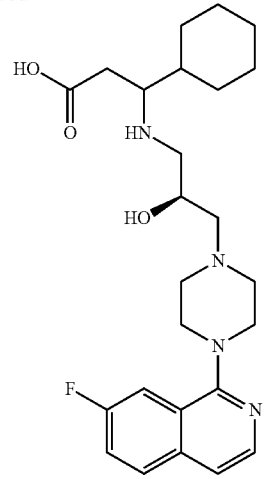

Compound 3-cyclohexyl-3-({(2S)-3-[4-(7-fluoroisoquinolin-1-yl) piperazin-1-yl]-2-hydroxypropyl}amino)propanoic acid (formate salt) as a mixture of diastereoisomers was prepared according to the synthesis described for compound 138 using racemic 3-amino-3-cyclohexylpropanoic acid. LC-MS (M-H⁺)=459.5. ¹H NMR (500 MHz, DMSO-d6) δ 1H NMR (500 MHz, DMSO-d6) d ppm 0.82-1.32 (m, 5H), 1.47-1.80 (m, 6H), 2.04-2.16 (m, 1H), 2.20-2.28 (m, 1H), 2.48 (d, J=6.85 Hz, 2H), 2.72 (br. s., 5H), 2.80-2.94 (m, 2H), 3.29 (br. s., 4H), 3.88 (d, J=5.87 Hz, 1H), 5.02 (br. s., 1H), 7.45 (d, J=5.38 Hz, 1H), 7.65 (td, J=8.56, 2.45 Hz, 1H), 7.69 (d, J=9.78 Hz, 1H), 8.01 (dd, J=9.05, 5.62 Hz, 1H), 8.12 (d, J=5.87 Hz, 1H), 8.15 (s, 1H).

Preparation of Compound 138

Compound 138 was prepared as described herein below.

Step 1—Synthesis of 7-fluoro-1-(4-{[(2R)-oxiran-2-yl]methyl}piperazin-1-yl)isoquinoline

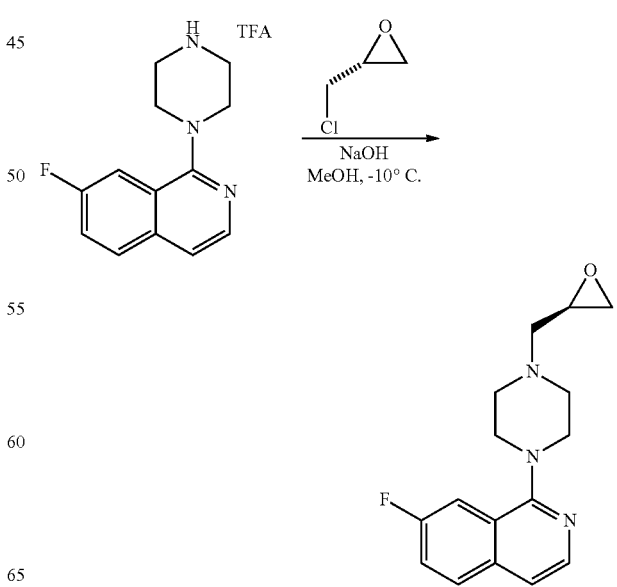

The title intermediate was prepared according to the procedure described for the synthesis of 7-fluoro-1-(4-{[(2R)-oxiran-2-yl]methyl}piperazin-1-yl)isoquinoline (see compound 139) using (R)-(+)-epichlorohydrin (Y=92%). LC-MS (M-H+)=288.3

Step 2—Synthesis of (2S)-cyclohexyl({(2S)-3-[4-(7-fluoroisoquinolin-1-yl)piperazin-1-yl]-2-hydroxypropyl}amino)acetic acid (formate salt, compound 138)

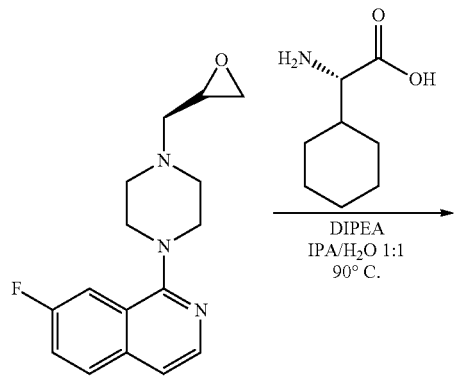

Compound 138 was prepared according to the procedure described for compound 139 using 7-fluoro-1-(4-{[(2R)-oxiran-2-yl]methyl}piperazin-1-yl)isoquinoline and (2S)-amino(cyclohexyl)acetic acid (Y=27%). LC-MS (M-H+)=445.2. $^1$H NMR (500 MHz, DMSO-d6) δ ppm 1.09-1.37 (m, 5H), 1.62-1.85 (m, 6H), 2.57-2.60 (m, 4H), 2.73-2.89 (m, 5H), 2.94 (dd, J=11.98, 4.16 Hz, 1H), 3.11 (d, J=4.40 Hz, 1H), 3.34 (d, J=7.34 Hz, 4H), 3.96-4.09 (m, 1H), 7.52 (d, J=5.38 Hz, 1H), 7.71 (td, J=8.68, 2.69 Hz, 1H), 7.76 (dd, J=10.03, 2.20 Hz, 1H), 8.07 (dd, J=9.29, 5.87 Hz, 1H), 8.18 (d, J=5.87 Hz, 1H), 8.21 (s, 1H).

Preparation of Compound 139

Compound 139 was prepared as described herein below.

Step 1—Synthesis of tert-butyl 4-(7-fluoroisoquinolin-1-yl)piperazine-1-carboxylate

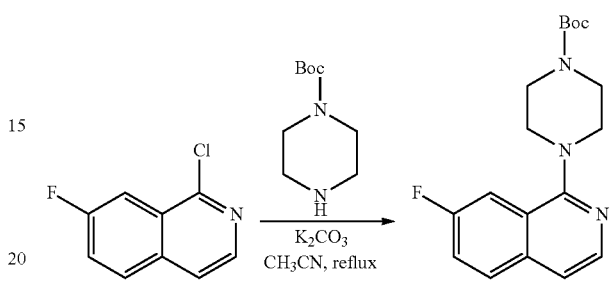

The title intermediate was prepared as described for the synthesis of intermediate 2c using 1-chloro-7-fluoroisoquinoline and N-Boc-piperazine (Y=94%). LC-MS (M-H+)=332.3

Step 2—Synthesis of 7-fluoro-1-(piperazin-1-yl)isoquinoline (trifluoroacetic acid salt)

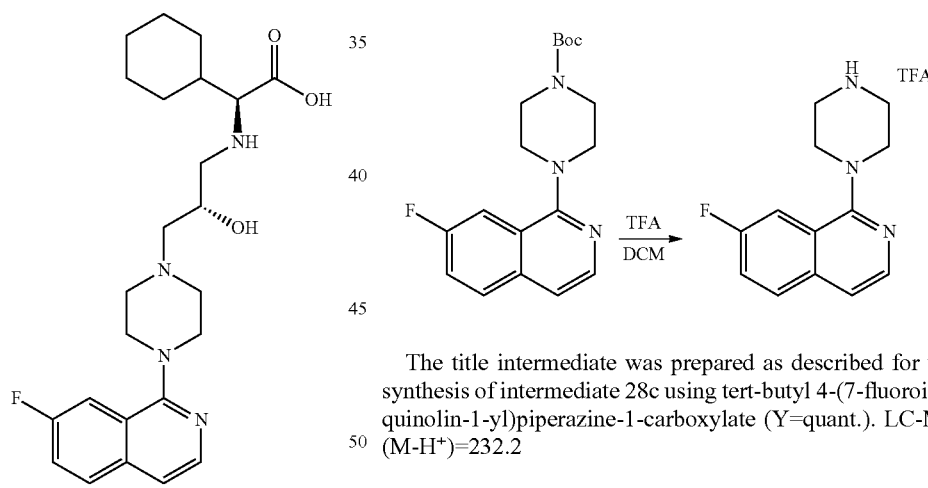

The title intermediate was prepared as described for the synthesis of intermediate 28c using tert-butyl 4-(7-fluoroisoquinolin-1-yl)piperazine-1-carboxylate (Y=quant.). LC-MS (M-H+)=232.2

Step 3—Synthesis of 7-fluoro-1-(4-{[(2S)-oxiran-2-yl]methyl} piperazin-1-yl)isoquinoline

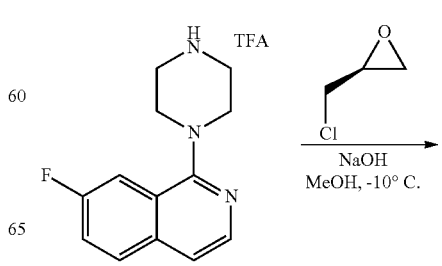

-continued

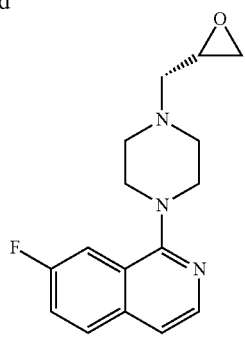

7-fluoro-1-(piperazin-1-yl)isoquinoline (trifluoroacetic acid salt, 448 mg, 1.3 mmol) was dissolved in MeOH (12 mL), NaOH (156 mg, 3.9 mmol) was added followed by (S)-(+)-epichlorohydrin (0.92 mL, 11.7 mmol) at −10° C. The reaction mixture was stirred at the same temperature for 30 h then was placed at 4° C. overnight. The mixture was filtered, the solid was washed with acetone and the organic phase was evaporated in vacuum. The residue was chromatographed on silica gel (SNAP 50, Cy:EtOAc:MeOH 6:3:1) to give 370 mg (98% yield) of 7-fluoro-1-(4-{[(2S)-oxiran-2-yl]methyl}piperazin-1-yl)isoquinoline as a yellow oil. LC-MS (M-H$^+$)=288.3

Step 4—Synthesis of (2R)-cyclohexyl({(2R)-3-[4-(7-fluoroisoquinolin-1-yl)piperazin-1-yl]-2-hydroxypropyl}amino)acetic acid (formate salt, compound 139)

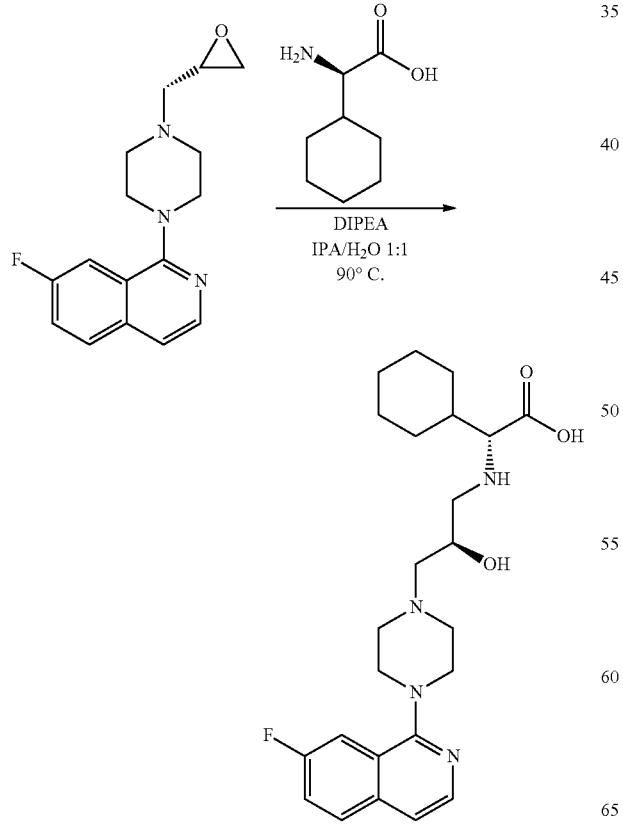

7-fluoro-1-(4-{[(2S)-oxiran-2-yl]methyl}piperazin-1-yl)isoquinoline (60 mg, 0.21 mmol), (2R)-amino(cyclohexyl)acetic acid (98 mg, 0.63 mmol) and DIPEA (150 μL, 0.84 mmol) were dissolved in a mixture of isopropanol/water 1:1 and stirred at 90° C. for 3 h. The solvent was evaporated in vacuo, the residue was treated with EtOAc and chromatographed on C18 (SNAP 30, gradient: acetonitrile+0.1% formic acid 0-23% in water+0.1% formic acid) to give 35 mg (0.07 mmol, 33% yield) of (2R)-cyclohexyl({(2R)-3-[4-(7-fluoroisoquinolin-1-yl)piperazin-1-yl]-2-hydroxypropyl}amino)acetic acid (formate salt). LC-MS (M-H$^+$)=445.2.

$^1$H NMR (500 MHz, DMSO-d6) δ ppm 0.99-1.36 (m, 5H), 1.53-1.78 (m, 6H), 2.47 (d, J=6.36 Hz, 2H), 2.65-2.81 (m, 5H), 2.86 (dd, J=11.98, 4.16 Hz, 1H), 3.02 (d, J=4.40 Hz, 1H), 3.28 (br. s., 6H), 3.88-4.00 (m, 1H), 7.45 (d, J=5.87 Hz, 1H), 7.65 (td, J=8.68, 2.69 Hz, 1H), 7.70 (dd, J=10.27, 1.96 Hz, 1H), 8.01 (dd, J=9.05, 5.62 Hz, 1H), 8.12 (d, J=5.87 Hz, 1H), 8.17 (s, 1H).

Preparation of Compound 140

Compound 140 was prepared as described herein below.

Step 1—Synthesis of (2S)-cyclohexyl({(2R)-3-[4-(7-fluoroisoquinolin-1-yl)piperazin-1-yl]-2-hydroxypropyl}amino)acetic acid (formate salt, compound 140)

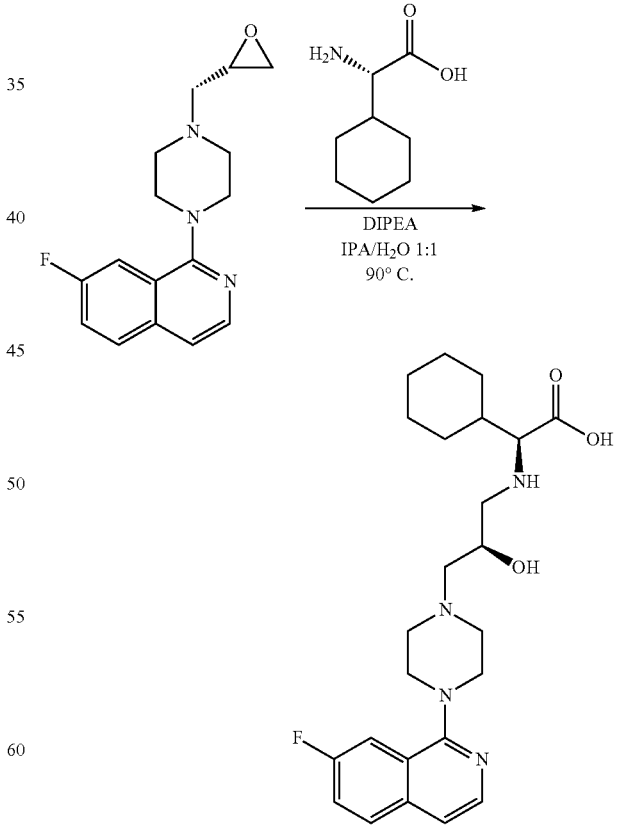

Compound (2S)-cyclohexyl({(2R)-3-[4-(7-fluoroisoquinolin-1-yl)piperazin-1-yl]-2-hydroxypropyl}amino)acetic acid (formate salt) was prepared according to the synthesis described for compound 139 using (2S)-amino(cyclohexyl) acetic acid (Y=15%). LC-MS (M-H⁺)=445.3.

¹H NMR (500 MHz, DMSO-d6) δ ppm 0.99-1.39 (m, 5H), 1.54-1.78 (m, 6H), 2.52-2.54 (m, 2H), 2.67-2.90 (m, 6H), 3.06 (d, J=4.40 Hz, 1H), 3.27 (br. s., 4H), 3.88-3.99 (m, 1H), 7.45 (d, J=5.38 Hz, 1H), 7.65 (td, J=8.80, 2.45 Hz, 1H), 7.70 (dd, J=10.03, 2.20 Hz, 1H), 8.01 (dd, J=9.05, 5.62 Hz, 1H), 8.11 (d, J=5.38 Hz, 1H), 8.16 (s, 1H).

Preparation of Compound 141

Compound 141 was prepared as described herein below.

Step 1—Synthesis of (3R)-3-({(2R)-3-[4-(7-fluoroisoquinolin-1-yl) piperazin-1-yl]-2-hydroxypropyl}amino)-3-phenylpropanoic acid (formate salt, compound 141)

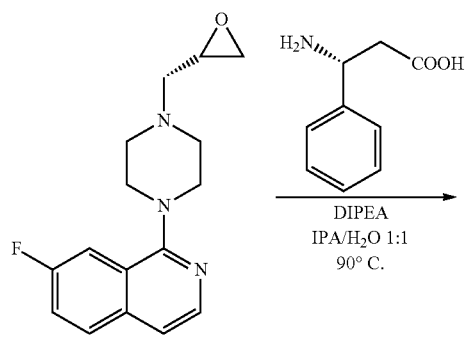

Compound (3R)-3-({(2R)-3-[4-(7-fluoroisoquinolin-1-yl)piperazin-1-yl]-2-hydroxypropyl}amino)-3-phenylpropanoic acid (formate salt) was prepared according to the synthesis described for compound 139 using (3R)-3-amino-3-phenylpropanoic acid (Y=19%). LC-MS (M-H+)=453.4.

¹H NMR (500 MHz, DMSO-d6) δ ppm 2.33-2.46 (m, 4H), 2.55-2.73 (m, 6H), 3.23 (br. s., 4H), 3.78-3.85 (m, 1H), 4.11 (dd, J=9.78, 4.89 Hz, 1H), 7.25-7.31 (m, 1H), 7.36 (t, J=7.58 Hz, 2H), 7.39-7.47 (m, 3H), 7.61-7.70 (m, 2H), 8.00 (dd, J=8.80, 5.87 Hz, 1H), 8.11 (d, J=5.87 Hz, 1H).

Preparation of Compound 142

Compound 142 was prepared as described herein below.

Step 1—Synthesis of (3R)-3-({(2S)-3-[4-(7-fluoroisoquinolin-1-yl) piperazin-1-yl]-2-hydroxypropyl}amino)-3-phenylpropanoic acid (formate salt, compound 142)

Compound (3R)-3-({(2S)-3-[4-(7-fluoroisoquinolin-1-yl) piperazin-1-yl]-2-hydroxypropyl}amino)-3-phenylpropanoic acid (formate salt) was prepared according to the synthesis described for compound 138 using (3R)-3-amino-3-phenylpropanoic acid (Y=19%). LC-MS (M-H+)=453.4.

¹H NMR (500 MHz, DMSO-d6) δ ppm 2.33-2.56 (m, 5H), 2.57-2.72 (m, 5H), 3.23 (br. s., 4H), 3.74-3.81 (m, 1H), 4.08 (dd, J=10.03, 4.65 Hz, 1H), 7.26-7.31 (m, 1H), 7.36 (t, J=7.58 Hz, 2H), 7.40-7.46 (m, 3H), 7.61-7.70 (m, 2H), 8.00 (dd, J=9.05, 5.62 Hz, 1H), 8.11 (d, J=5.87 Hz, 1H).

Preparation of Compound 167

Compound 167 was prepared as described herein below.

Step 1—Synthesis of 3-cyclohexyl-3-[(2-{[1-(7-fluoroisoquinolin-1-yl) piperidin-4-yl]amino}ethyl)amino]propan-1-ol (compound 167)

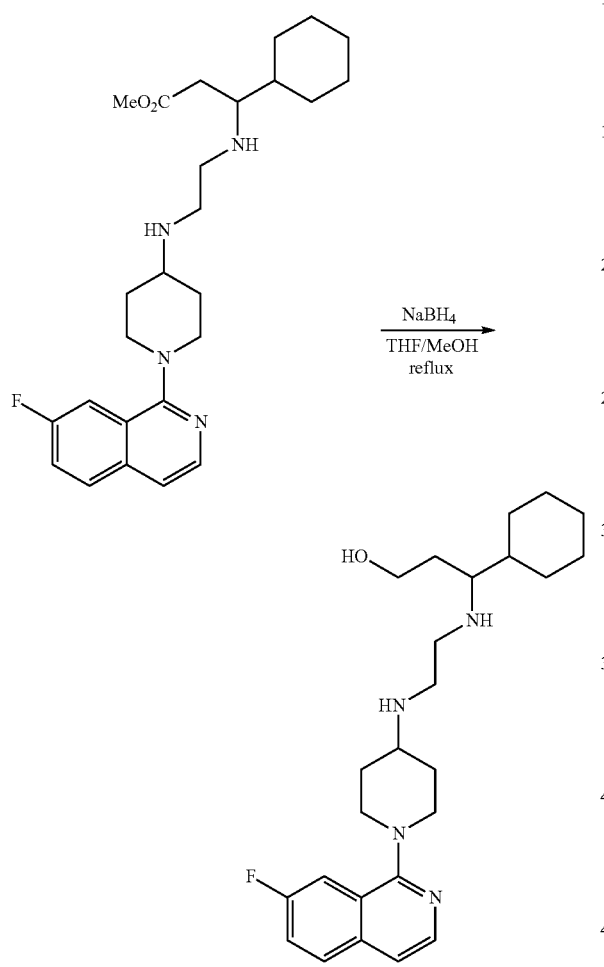

To a solution of methyl 3-cyclohexyl-3-[(2-{[1-(7-fluoroisoquinolin-1-yl)piperidin-4-yl]amino}ethyl)amino]propanoate (compound 189, 45 mg, 0.1 mmol) in THF (10 mL) NaBH$_4$ (19 mg, 0.5 mmol) was added. The mixture refluxed for 1 h then MeOH (0.13 mL, 3.3 mmol) was added. After stirring 18 h at reflux the mixture was cooled to rt, concentrated under vacuum and partitioned between water and DCM. The organic phase was dried over Na$_2$SO$_4$ and concentrated under vacuum. The residue was purified by preparative HPLC (C18, CH$_3$CN from 30% to 65% in H$_2$O) to afford 3-cyclohexyl-3-[(2-{[1-(7-fluoroisoquinolin-1-yl)piperidin-4-yl]amino}ethyl)amino]propan-1-ol (14 mg, 0.03 mmol, 30% yield over two steps). LC-MS (M-H$^+$)=429.3.

$^1$H NMR (300 MHz, CHLOROFORM-d) δ=8.12 (d, J=5.9 Hz, 1H), 7.76 (dd, J=5.6, 8.9 Hz, 1H), 7.67 (dd, J=2.6, 10.2 Hz, 1H), 7.40 (dt, J=2.6, 8.6 Hz, 1H), 7.27 (d, J=5.5 Hz, 1H), 4.01 (ddd, J=3.8, 5.8, 11.6 Hz, 1H), 3.86-3.63 (m, 2H), 3.49-2.72 (m, 13H), 2.20 (d, J=11.2 Hz, 2H), 2.09-1.54 (m, 8H), 1.45-0.87 (m, 4H).

Preparation of Compound 189

Compound 189 was prepared as described herein below.

Step 1—Synthesis of tert-butyl [1-(7-fluoroisoquinolin-1-yl)piperidin-4-yl]carbamate

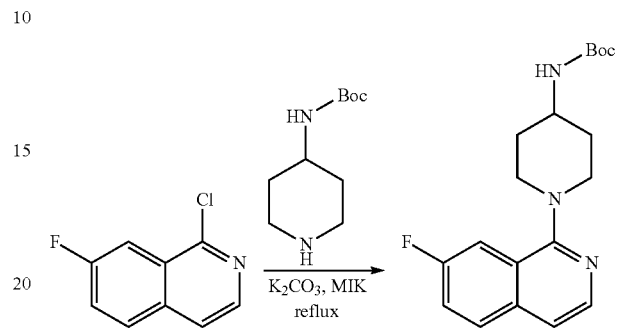

Potassium carbonate (4.6 g, 33 mmol) was added to a stirred solution of 1-chloro-7-fluoroisoquinoline (5 g, 27.5 mmol) and tert-butyl piperidin-4-ylcarbamate (13.8 g, 68.8 mmol) in methyl isopropyl ketone (50 mL) at room temperature. The resulting mixture was heated to reflux overnight. UPLC check showed the reaction was complete. The mixture was then allowed to cool to room temperature then water was added. The mixture was extracted with EtOAc, the combined organic phases were washed with brine and dried over sodium sulfate. The solvents were evaporated under reduced pressure and the resulting residue was purified by flash chromatography on silica gel (from 100% hexane to hexane/Ethyl acetate 8:2) to obtain tert-butyl [1-(7-fluoroisoquinolin-1-yl)piperidin-4-yl]carbamate (7.1 g, 20.6 mmol, 75% yield). LC-MS (M-H$^+$)=346.2

Step 2—Synthesis of 1-(7-fluoroisoquinolin-1-yl)-N-[(4-methoxyphenyl)methyl]piperidin-4-amine hydrochloride

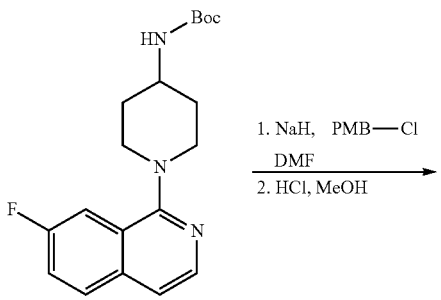

-continued

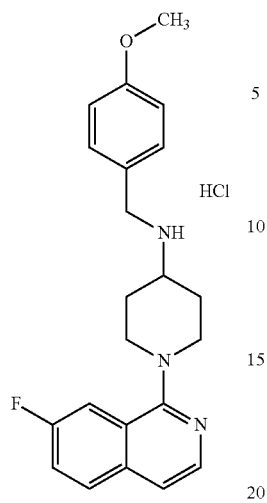

-continued

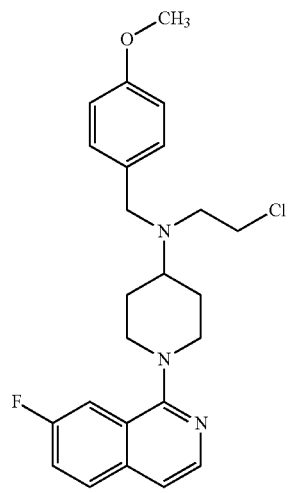

To a solution of tert-butyl [1-(7-fluoroisoquinolin-1-yl)piperidin-4-yl]carbamate (5.5 g, 15.9 mmol) in dry DMF (50 mL) NaH (60% mineral oil, 1.5 g, 31.8 mmol) was added. After stirring 1 h at room temperature p-methoxybenzyl chloride (5 mL, 31.8 mmol) was added. The reaction mixture was stirred at room temperature overnight then was poured into cold water (300 mL). The solution was extracted with EtOAc, the combined organic layers were washed with brine, dried over sodium sulfate and concentrated to dryness. The dried residue was dissolved in a solution of HCl in MeOH (1.25 M, 200 mL) and the mixture was refluxed for 2 h. The solvent was removed under vacuum and the resulting residue was treated with isopropanol and dried to give 1-(7-fluoroisoquinolin-1-yl)-N-[(4-methoxyphenyl)methyl]piperidin-4-amine hydrochloride (5.6 g, 15.3 mmol, 96% yield). LC-MS (M-H$^+$)=366.2

Step 3—Synthesis of N-(2-chloroethyl)-1-(7-fluoroisoquinolin-1-yl)-N-[(4-methoxyphenyl)methyl]piperidin-4-amine

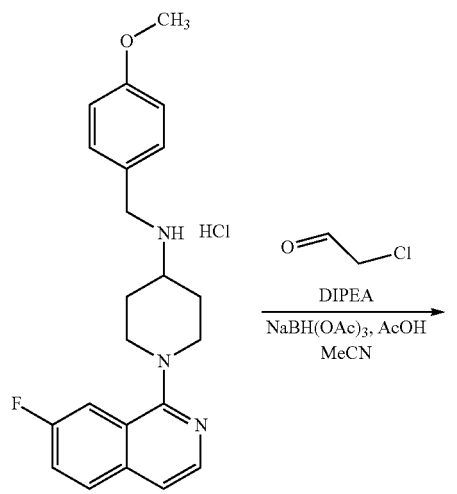

To a solution of 1-(7-fluoroisoquinolin-1-yl)-N-[(4-methoxyphenyl)methyl]piperidin-4-amine hydrochloride (2 g, 5 mmol) and DIPEA (0.9 mL, 5 mmol) in acetonitrile (10 mL) chloroacetaldehyde (50 wt % solution in H$_2$O, 2.5 mL, 19.9 mmol) was added. After stirring 15' at rt, acetic acid (0.57 ml) and NaBH(OAc)$_3$ (2.1 g, 10 mmol) were added. The mixture was stirred 3 h at rt adjusting pH to 5-6 by addition of 0.1 M HCl. After addition of NaHCO$_3$ the solution was extracted with DCM, the organic phase was washed with water, treated with Na$_2$SO$_4$ and concentrated under vacuum. EtOAc was added to the residue, the resulting solid was filtered off and the solvent was evaporated under reduced pressure. A purification by flash chromatography (silica gel, CHCl$_3$/MeOH 9:1) afforded N-(2-chloroethyl)-1-(7-fluoroisoquinolin-1-yl)-N-[(4-methoxyphenyl)methyl]piperidin-4-amine (650 mg, 1.5 mmol, 30% yield). LC-MS (M-H$^+$)=428.1

Step 4—Synthesis of methyl 3-cyclohexyl-3-[(2-{[1-(7-fluoroisoquinolin-1-yl)piperidin-4-yl][(4-methoxyphenyl)methyl] amino}ethyl) amino]propanoate

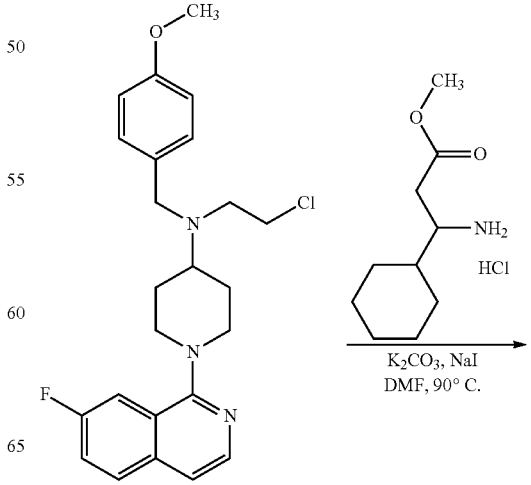

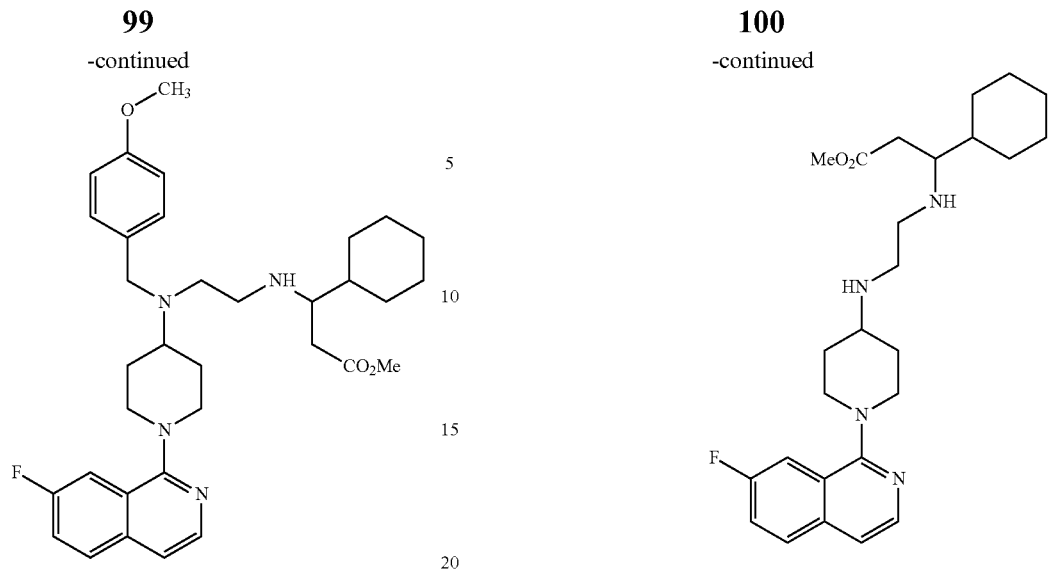

A solution of sodium iodide (39 mg, 0.26 mmol) and N-(2-chloroethyl)-1-(7-fluoroisoquinolin-1-yl)-N-[(4-methoxyphenyl)methyl] piperidin-4-amine (110 mg, 0.26 mmol) in DMF (5 mL) was stirred 15' then was cooled to 0° C. Potassium carbonate (107 mg, 0.77 mmol) was added followed by one-pot addition of methyl 3-amino-3-cyclohexylpropanoate hydrochloride (114 mg, 0.51 mmol) in DMF (5 mL). The mixture was stirred at 90° C. overnight then was cooled and poured into cold water. The solution was extracted with DCM, the organic phase was dried over $Na_2SO_4$ and concentrated under vacuum to give methyl 3-cyclohexyl-3-[(2-{[1-(7-fluoroisoquinolin-1-yl)piperidin-4-yl][(4-methoxyphenyl)methyl]amino}ethyl)amino]propanoate (110 mg, 0.20 mmol, 77% yield), that was progressed without further purification. LC-MS (M-H$^+$)=577.3

Step 5—Synthesis of methyl 3-cyclohexyl-3-[(2-{[1-(7-fluoroisoquinolin-1-yl)piperidin-4-yl]amino}ethyl)amino]propanoate (compound 189)

A mixture of methyl 3-cyclohexyl-3-[(2-{[1-(7-fluoroisoquinolin-1-yl)piperidin-4-yl][(4-methoxyphenyl)methyl]amino}ethyl)amino]propanoate (110 mg, 0.20 mmol) and TFA (1 mL) in DCM (10 mL) was refluxed overnight. After cooling to rt sat. $NaHCO_3$ was added, the resulting solution was extracted with EtOAc, the organic phase was dried over $Na_2SO_4$ and concentrated under vacuum. Purification by preparative HPLC (C-18, $CH_3CN$ from 10% to 45% in $H_2O$) provided 58 mg (0.13 mmol, 65% yield) of methyl 3-cyclohexyl-3-[(2-{[1-(7-fluoroisoquinolin-1-yl)piperidin-4-yl]amino}ethyl)amino]propanoate. LC-MS (M-H$^+$)=457.3.

$^1$H NMR (500 MHz, DMSO-d6/$D_2O$) δ ppm 0.94-1.33 (m, 5H), 1.53-2.03 (m, 8H), 2.22 (d, J=11.11 Hz, 2H), 2.77-2.90 (m, 2H), 3.04-3.18 (m, 2H), 3.32-3.52 (m, 6H), 3.64-3.71 (m, 3H), 3.72-4.22 (m, 2H), 7.53 (d, J=5.90 Hz, 1H), 7.66-7.80 (m, 2H), 7.98-8.12 (m, 2H).

Preparation of Compound 190

Compound 190 was prepared as described herein below.

Step 1—Synthesis of lithium 3-cyclohexyl-3-[(2-{[1-(7-fluoroisoquinolin-1-yl)piperidin-4-yl]amino}ethyl)amino]propanoate (compound 190)

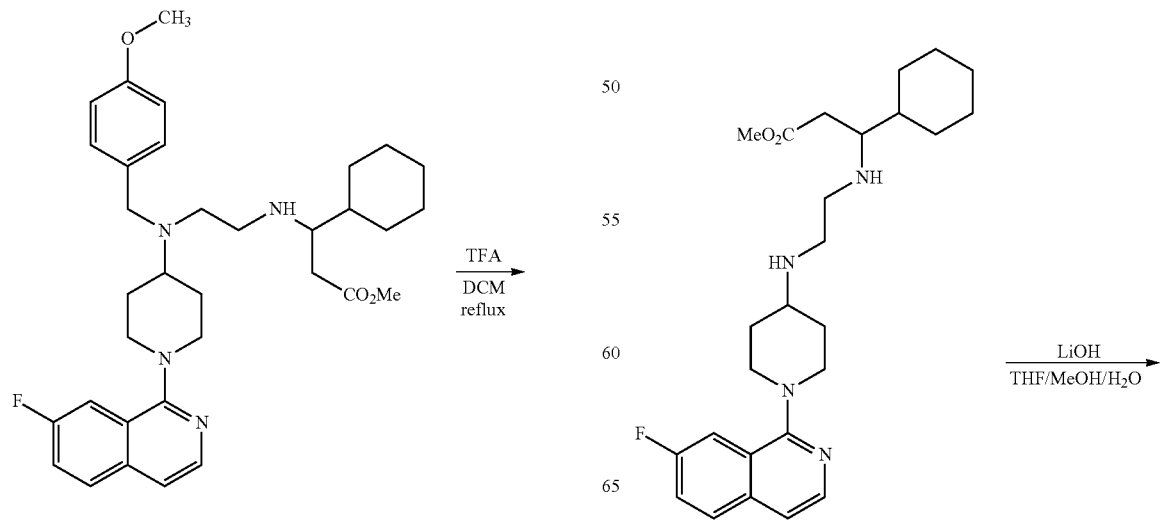

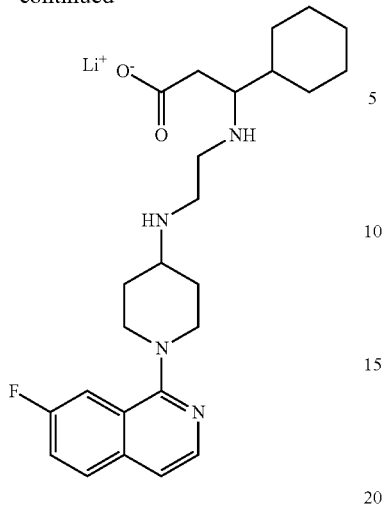

To a solution of methyl 3-cyclohexyl-3-[(2-{[1-(7-fluoroisoquinolin-1-yl)piperidin-4-yl]amino}ethyl)amino]propanoate (compound 189, 60 mg, 0.13 mmol) in a mixture of THF (0.4 mL), MeOH (0.2 mL) and water (0.2 mL) LiOH× H2O (11 mg, 0.26 mmol) was added. The reaction mixture was stirred at 55° C. for 20 minutes then the solvent was evaporated and the crude was purified by reverse chromatography (C-18, from 100% water to 7/3 water/acetonitrile) to obtain lithium 3-cyclohexyl-3-[(2-{[1-(7-fluoroisoquinolin-1-yl)piperidin-4-yl]amino}ethyl)amino]propanoate (32 mg, 0.07 mmol, 56% yield). LC-MS (M-H$^+$)=443.3.

$^1$H NMR (500 MHz, DMSO-d6) δ ppm 0.82-1.29 (m, 5H), 1.41-1.80 (m, 8H), 1.86-2.04 (m, 3H), 2.09 (dd, J=15.30, 3.91 Hz, 1H), 2.58-2.79 (m, 6H), 2.93 (t, J=12.50 Hz, 2H), 3.64 (d, J=12.49 Hz, 2H), 7.41 (d, J=5.76 Hz, 1H), 7.59-7.69 (m, 2H), 7.99 (dd, J=8.71, 5.69 Hz, 1H), 8.09 (d, J=5.80 Hz, 1H).

Preparation of Compound 191

Compound 191 was prepared as described herein below.

Step 1—Synthesis of 3-cyclohexyl-3-[(2-{[1-(7-fluoroisoquinolin-1-yl)piperidin-4-yl]amino}ethyl)amino]-N-hydroxypropanamide (compound 191)

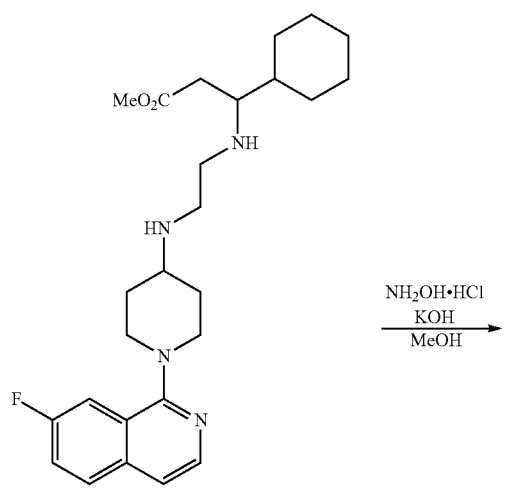

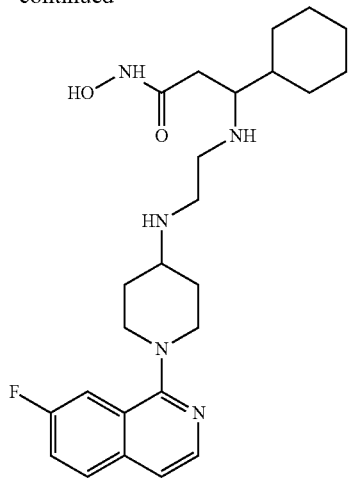

To a stirred solution of hydroxylamine hydrochloride (2.6 g, 40 mmol) in MeOH (12 mL) a solution of potassium hydroxide (3.3 g, 59 mmol) in MeOH (7 mL) was added slowly at 0° C. After addition, the mixture was stirred for 30 minutes at 0° C. then was allowed to reach room temperature. The resulting precipitate was filtered and the solution of free hydroxylamine was placed in 100 mL flask. Methyl 3-cyclohexyl-3-[(2-{[1-(7-fluoroisoquinolin-1-yl)piperidin-4-yl]amino}ethyl)amino]propanoate (compound 189, 87 mg, 0.19 mmol) in MeOH (5 mL) was added to this solution. The resulting solution was degassed at 0° C. for 30 minutes then was concentrated to dryness. The residue was dissolved in water, the aqueous phase was acidified to pH 5 by adding 1M HCl and extracted with EtOAc. The organic layer was washed with brine, dried over sodium sulfate and concentrated. The residue was purified by reverse chromatography (C-18, from 100% water to 8:2 water/acetonitrile) to give 3-cyclohexyl-3-[(2-{[1-(7-fluoroisoquinolin-1-yl)piperidin-4-yl]amino}ethyl)amino]-N-hydroxypropanamide (13 mg, 0.028 mmol, 15% yield). LC-MS (M-H$^+$)=458.3.

$^1$H NMR (400 MHz, DMSO-d6) δ ppm 0.92-1.81 (m, 12H), 1.31-1.47 (m, 1H), 1.90-2.16 (m, 4H), 2.65-2.72 (m, 3H), 2.74-2.81 (m, 2H), 2.81-2.89 (m, 1H), 2.88-2.99 (m, 2H), 3.69 (d, J=12.72 Hz, 2H), 7.43 (d, J=5.26 Hz, 1H), 7.60-7.70 (m, 2H), 8.00 (dd, J=9.87, 5.92 Hz, 1H), 8.07-8.12 (m, 1H).

EXAMPLES

Example 1

Inhibition of DNA Gyrase or Topo IV in *E. coli* and *S. aureus*

The above compounds were tested for the inhibition of the enzyme DNA gyrase in a gyrase supercoiling assay and for the inhibition of the enzyme topoisomerase IV in a decatenation assay, in both Gram positive and Gram negative bacteria, according to the following methods.

Both the assays were carried out according to a set-up method modified from the article to Blanche F, et al. "Differential Behaviors of *Staphylococcus aureus* and *Escherichia coli* Type II DNA Topoisomerases", Antimicrob. Agents Chemother., 1996, Vol. 40, No. 12 p. 2714-2720.

The compounds were screened at single concentration (200, 100 or 50 μM), in duplicate.

Ciprofloxacin and novobiocin were used as reference compounds, at single concentration of 200 and 50 μM, respectively.

DNA Gyrase Supercoiling Assay.

Reagents from S. aureus and E. coli Gyrase Supercoiling Assay kits (Inspiralis, UK) were used. A master mix with a total volume sufficient for the number of reactions to perform was prepared with the following reagents: 5× assay buffer, relaxed pBR322 substrate (0.5 μg/reaction), RNase-DNase free water. Aliquotes of this mix were dispensed in each tube, then 10× compound stock solutions or vehicle control (DMSO), were added to each reaction tube.

Reaction was started with E. Coli (2 U/reaction) or S. aureus (1 U/reaction) gyrase enzyme addition.

A sample added with an equal volume of dilution buffer was used as negative control (without enzyme).

The reaction tubes were gentle vortexed and incubated 30 minutes at 37° C. Each reaction was stopped by adding 30 μl of Stop Buffer and 30 μl chloroform/isoamyl alcohol (24/1), briefly vortexed for 5-10 seconds and centrifuged at 20000×g for 2 minutes. Samples were loaded onto 1% agarose gel and subjected to electrophoresis for 1 hour at 80V constant voltage in TAE (40 mM Tris-acetate, 2 mM EDTA).

Data acquisition and analysis. Treatment of relaxed pBR322 with DNA gyrase converted the relaxed topoisomers (DNAs of different linking number) to the supercoiled form of the plasmid, which migrates faster on an agarose gel. An upper band might also be visible, which consists of open-circular (nicked) DNA which is present in the relaxed substrate but co-migrates with some of the relaxed topoisomers.

Bands were visualized by ethidium bromide staining (dil 1:20000) for 30 minutes followed by destaining in distilled water for 10 minutes.

In order to evaluate the compounds activity on the enzyme, the bands of supercoiled DNAs in the gel were photographed by a digital imaging system ImageQuant LAS 4000 (GE Healthcare) according to manufacturer's instructions.

The fluorescent intensity of each band was analysed by ImageQuant TL software and it was expressed as volume (volume of the uncalibrated quantity of material in the image feature after subtraction of the background intensity by using rolling ball method).

Each band intensity was compared, as percentage, to vehicle sample band intensity, which served as positive control, on the same gel.

Inhibitory activity was expressed as percent of inhibition versus the positive control.

The results are summarized in the following Table 2.

Topoisomerase IV Decatenation Assay

S. aureus and E. coli Topoisomerase IV decatenation kits (Inspiralis, UK) were used. A master mix with a total volume sufficient for the number of reactions to perform was prepared with the following reagents: 5× assay buffer (50 mM HEPES-KOH (pH 7.6), 100 mM potassium glutamate, 10 mM magnesium acetate, 10 mM DTT, 1 mM ATP, 50 μg/ml albumin), kDNA substrate (200 ng/reaction), RNase-DNase free water. Aliquots of this mix were dispensed in each tube, then 10× compound stock solutions or vehicle control (DMSO), were added in each reaction tube.

Reaction was started with Topoisomerase IV enzyme (0.5 U/reaction) addition.

A sample added with an equal volume of dilution buffer was used as negative control (without enzyme).

The reaction tubes were gentle vortexed and incubated 30 minutes at 37° C. Each reaction was stopped by adding 30 μl of Stop Buffer and 30 μl of chloroform/isoamyl alcohol (24/1), briefly vortexed for 5-10 seconds and centrifuged at 20000×g for 2 minutes. Samples taken from the upper phase were loaded into 1% agarose gel and subjected to electrophoresis for 1 hour at 80V constant voltage in TAE (40 mM Tris-acetate, 2 mM EDTA).

Data acquisition and analysis. Due to the high molecular mass, kDNA could not enter an agarose gel under normal electrophoresis conditions, but remained in the wells. In the presence of Topo IV topoisomerase mini-circles (2.5 Kb) were released from kDNA by decatenation and were quickly and easily resolved in the gel at relatively high voltages.

Bands were visualized by ethidium bromide staining (dil 1:20000) for 30 minutes followed by destaining in distilled water for 10 minutes.

For single concentration screening assay, in order to evaluate the compounds activity on the enzymes, the bands of decatenated DNAs in the gel were photographed by a digital imaging system ImageQuant LAS 4000 (GE Healthcare) according to manufacturer's instructions.

The fluorescent intensity of each band was analyzed by ImageQuant TL software and it was expressed as volume (volume of the uncalibrated quantity of material in the image feature after subtraction of the background intensity by using rolling ball method).

Each band intensity was compared, as percentage, to vehicle sample band intensity, which served as positive control, on the same gel.

Inhibitory activity was expressed as percent of inhibition versus the positive control.

The results are summarized in the following Table 2.

TABLE 2

| Compound No | E. coli | | S. aureus | |
| --- | --- | --- | --- | --- |
| | % inhibition DNA gyrase | % inhibition Topo IV | % inhibition DNA gyrase | % inhibition Topo IV |
| 2 | n/a | 65 | n/a | n/a |
| 3 | 59 | n/a | n/a | n/a |
| 4 | n/a | 53 | 84 | n/a |
| 21 | n/a | n/a | 67 | n/a |
| 31 | n/a | n/a | 65 | n/a |
| 35 | n/a | n/a | 78 | n/a |
| 36 | n/a | n/a | 90 | n/a |
| 38 | n/a | n/a | 63 | n/a |
| 39 | 50 | n/a | 74 | n/a |
| 42 | n/a | n/a | 84 | n/a |
| 43 | n/a | n/a | 100 | n/a |
| 45 | n/a | n/a | 81 | n/a |
| 50 | 92 | n/a | n/a | n/a |
| 53 | 64 | n/a | 57 | n/a |
| 58 | 100 | n/a | n/a | n/a |
| 60 | 100 | n/a | 89 | n/a |
| 68 | 100 | n/a | n/a | n/a |
| 70 | 86 | n/a | 75 | n/a |
| 71 | 56 | n/a | n/a | n/a |
| 74 | 65 | n/a | 61 | n/a |
| 75 | 69 | n/a | 61 | n/a |
| 81 | 80 | n/a | n/a | n/a |
| 82 | 85 | n/a | 82 | n/a |
| 83 | 69 | n/a | n/a | n/a |
| 85 | 78 | n/a | 86 | n/a |
| 87 | 79 | n/a | 96 | n/a |
| 96 | 88 | n/a | 91 | n/a |
| 97 | 85 | n/a | 86 | n/a |
| 101 | 100 | n/a | 100 | n/a |
| 107 | 92 | n/a | 74 | n/a |

TABLE 2-continued

| Compound No | E. coli | | S. aureus | |
| --- | --- | --- | --- | --- |
| | % inhibition DNA gyrase | % inhibition Topo IV | % inhibition DNA gyrase | % inhibition Topo IV |
| 117 | 75 | n/a | n/a | n/a |
| 118 | 78 | n/a | n/a | n/a |
| 119 | n/a | n/a | 60 | n/a |
| 120 | n/a | n/a | 76 | n/a |
| 122 | 58 | n/a | n/a | n/a |
| 123 | 52 | n/a | n/a | n/a |
| 128 | n/a | n/a | 66 | n/a |
| 129 | 69 | n/a | n/a | n/a |
| 130 | n/a | n/a | 74 | n/a |
| 132 | n/a | n/a | 53 | n/a |
| 133 | 53 | n/a | 58 | n/a |
| 136 | 57 | n/a | 75 | n/a |
| 137 | 57 | n/a | 75 | n/a |
| 138 | n/a | n/a | 89 | n/a |
| 139 | n/a | n/a | 54 | n/a |
| 140 | 68 | n/a | 92 | n/a |
| 141 | n/a | n/a | 65 | n/a |
| 142 | n/a | n/a | 52 | n/a |
| 167 | n/a | n/a | 70 | n/a |
| 189 | n/a | n/a | 84 | n/a |
| 190 | 61 | n/a | 73 | n/a |
| 191 | n/a | n/a | 81 | n/a | n/a = not active

The above results showed that the exemplified compounds effectively inhibited DNA gyrase or topoisomerase IV in *E. coli*, which is a Gram positive bacterium, and/or *S. aureus*, which is a Gram negative bacterium.

The invention claimed is:

1. A compound of formula (I)

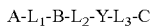

A-L$_1$-B-L$_2$-Y-L$_3$-C     (I)

wherein

A is a group of the following formula:

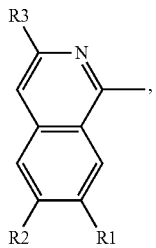

wherein

R1 is H or halogen atom,

R2 is H, halogen atom, OH, (C1-3)alkyl or (C1-3)alkoxy, and

R3 is H, (C1-3)alkyl or (C1-3)alkoxy;

L$_1$ is σ bond, —O— or —N(R')—, wherein R' is H or (C$_{1-3}$)alkyl;

B is a divalent residue of a piperazine or piperidine ring;

L$_2$ is σ bond, —CH$_2$—, —O—, or —N(R')—, wherein R' is H or (C$_{1-3}$)alkyl;

Y is a (C$_{1-6}$)alkylenyl, (C$_{2-6}$)alkenylenyl, (C$_{2-6}$)alkynylenyl, or (C$_{3-6}$)cycloalkylenyl group, said group being optionally substituted with one or more groups selected from —OH, (C$_{1-3}$)alkyl, (C$_{3-6}$)cycloalkyl, 3- to 5-membered oxacycloalkyl, —COOR', —NR'R" wherein R' and R", identical or different each other, are hydrogen atom or (C$_{1-3}$)alkyl;

L$_3$ is —O—, —(CH$_2$)$_2$—, —N(R')—, —N(R')—C(=O)—, —N(R')—C(=S)—, —N(R')—(C$_{1-6}$)alkylenyl-, —C(=O)—N(R')—, —C(=O)—N(R')—(C$_{1-6}$)alkylenyl-, —SO$_2$—N(R')—, —N(R')—SO$_2$—, wherein R' is hydrogen atom or (C$_{1-3}$)alkyl;

C is a group of formula (V), (VI), or (VIII):

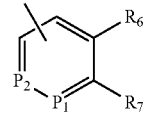     (V)

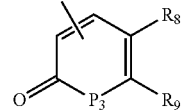     (VI)

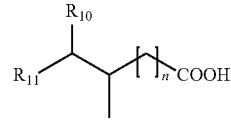     (VIII)

wherein n is an integer from 0 to 3

P$_1$ and P$_2$, equal or different each other, are CH or N

P$_3$ is O, S or NH;

R$_6$ and R$_7$ together form a 5- or 6-membered aliphatic or aromatic ring, optionally comprising at least one heteroatom selected from N and O, R$_8$ and R$_9$, equal or different each other, are a hydrogen atom or an aryl group, or together form a 5- or 6-membered aliphatic or aromatic ring, optionally comprising at least one heteroatom selected from N and O, R$_{10}$ and R$_{11}$ together form a 5- or 6-membered aliphatic or aromatic ring, and wherein each hydrogen atom linked to a carbon or nitrogen atom forming the ring of formulae (V), (VI), or (VIII) is optionally substituted with at least one substituent selected from the group consisting of halogen atom, (C$_{1-3}$)alkyl or (C$_{1-3}$)alkoxy;

or an addition salt with a pharmaceutically acceptable organic or inorganic acid or base, an enantiomer, N-oxide, or quaternary ammonium salt of said compound of formula (I).

2. The compound according to claim 1, wherein B is a group having the following formula (III)

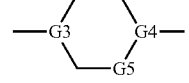     (III)

wherein

G3 and G4, identical or different each other, are C(R$_4$) or N, provided that that at least one of G3 and G4 is N, R$_4$ is hydrogen atom, —OH, —CN, —COOH, —NR'R" wherein R' and R", identical or different each other, are hydrogen atom or (C$_{1-3}$)alkyl;

G5 is C(=O) or C(H)(R$_5$);

wherein R$_5$ is hydrogen atom, CF$_3$, —(C$_{1-3}$)alkyl-CF$_3$, —COOR' and —CONR'R", wherein R' and R", identical or different each other, are hydrogen atom or (C$_{1-3}$)alkyl.

3. The compound according to claim 1, wherein $R_6$ and $R_7$ together form a ring selected from the group consisting of benzene, furan, tetrahydrofuran, dioxolane, piperidine and piperazine.

4. The compound according to claim 1, wherein $R_8$ and $R_9$, equal or different each other, are a hydrogen atom or an aryl group, or together form a ring selected from the group consisting of benzene, pyridine, and piperidine.

5. The compound according to claim 1, wherein C is a group having one of the following formulas:

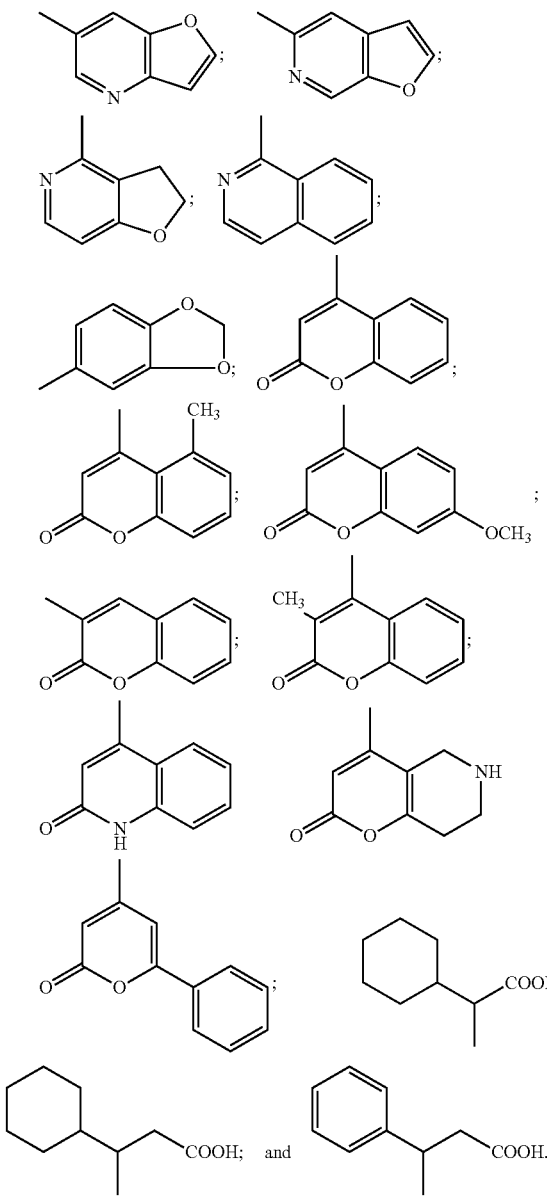

6. The compound according to claim 1, wherein said Y is a $(C_{1-4})$alkylenyl, $(C_{2-4})$alkynylenyl, or $(C_{5-6})$cycloalkylenyl group, said group being optionally substituted with one or more groups selected from —OH, methyl, $(C_{3-4})$cycloalkyl, 3- or 4-membered oxacycloalkyl, —COOH, —NR'R" wherein R' and R", identical or different each other, are hydrogen atom or methyl.

7. The compound according to claim 6, wherein said Y is a $(C_{1-4})$alkylenyl, $(C_{2-4})$alkynylenyl, or cyclohexylenyl group, said group being optionally substituted with one or more hydroxy groups.

8. The compound according to claim 1, wherein said $L_3$ is —O—, —(CH$_2$)$_2$—, —N(R')— wherein R' is H or $(C_{1-3})$alkyl, —NH—C(=O)—, —NH—$(C_{1-3})$alkylenyl-, —C(=O)—NH— or —C(=O)—NH—$(C_{1-3})$alkylenyl-.

9. The compound according to claim 8, wherein said $L_3$ is —O—, —(CH$_2$)$_2$—, or —N(R')— wherein R' is H or methyl, —NH—C(=O)—, —NH—CH$_2$—, —C(=O)—NH—, or —C(=O)—NH—CH$_2$—.

10. A pharmaceutical composition comprising at least one compound of formula (I) according to claim 1, a salt thereof with a pharmaceutically acceptable organic or inorganic acid or base, or an enantiomer thereof, or a quaternary ammonium salt thereof, or a N-oxide thereof, and at least one inert pharmaceutically acceptable excipient.

11. A method for treating a bacterial infection, comprising the administration of a compound of formula (I) according to claim 1 to a patient in need thereof.

12. A method for treating a bacterial infection, comprising administering, to a subject in need thereof, an effective amount of compound of formula (I)

$$A-L_1-B-L_2-Y-L_3-C \qquad (I)$$

wherein
A is a group of the following formula:

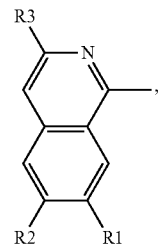

wherein
R1 is H or halogen atom,
R2 is H, halogen atom, OH, (C1-3)alkyl or (C1-3) alkoxy, and
R3 is H, (C1-3)alkyl or (C1-3)alkoxy;
$L_1$ is σ bond, —O— or —N(R')—, wherein R' is H or $(C_{1-3})$alkyl;
B is a divalent residue of a piperazine or piperidine ring;
$L_2$ is σ bond, —CH$_2$—, —O—, or —N(R')—, wherein R' is H or $(C_{1-3})$alkyl;
Y is a $(C_{1-6})$alkylenyl, $(C_{2-6})$alkenylenyl, $(C_{2-6})$alkynylenyl, or $(C_{3-6})$cycloalkylenyl group, said group being optionally substituted with one or more groups selected from —OH, $(C_{1-3})$alkyl, $(C_{3-6})$cycloalkyl, 3- to 5-membered oxacycloalkyl, —COOR', —NR'R" wherein R' and R", identical or different each other, are hydrogen atom or $(C_{1-3})$alkyl;
$L_3$ is —O—, —(CH$_2$)$_2$—, —N(R')—, —N(R')—C(=O)—, —N(R')—C(=S)—, —N(R')—$(C_{1-6})$alkylenyl-, —C(=O)—N(R')—$(C_{1-6})$alkylenyl-, —SO$_2$—N(R')—, —N(R')—SO$_2$—, wherein R' is hydrogen atom or $(C_{1-3})$alkyl;
C is a group having a 5- or 6-membered saturated or unsaturated ring, or a 9- or 10-membered fused bicyclic ring;

or an addition salt with a pharmaceutically acceptable organic or inorganic acid or base, an enantiomer, N-oxide, or quaternary ammonium salt of said compound of formula (I).

13. The method according to claim 12, wherein said bacterial infection is selected from the group consisting of a skin infection, a mucosal infection, a gynaecological infection, a respiratory tract infection (RTI), a CNS infection, a gastro-intestinal infection, a bone infection, a cardiovascular infection, a sexually transmitted infection, and a urinary tract infection.

* * * * *

UNITED STATES PATENT AND TRADEMARK OFFICE
CERTIFICATE OF CORRECTION

PATENT NO. : 10,369,130 B2  
APPLICATION NO. : 15/534874  
DATED : August 6, 2019  
INVENTOR(S) : Rosella Ombrato et al.

Page 1 of 1

It is certified that error appears in the above-identified patent and that said Letters Patent is hereby corrected as shown below:

On the Title Page

Item (73), the Assignee is incorrect. Item (73) should read:  
-- (73) Assignee: AZIENDE CHIMICHE RIUNITE ANGELINI FRANCESCO A.C.R.A.F. S.p.A., Rome (IT) --

Signed and Sealed this  
Twenty-ninth Day of October, 2019

Andrei Iancu  
*Director of the United States Patent and Trademark Office*